US008067180B2

(12) United States Patent
Kadyk et al.

(10) Patent No.: US 8,067,180 B2
(45) Date of Patent: Nov. 29, 2011

(54) MAPKS AS MODIFIERS OF THE RAC, AXIN, AND BETA-CATENIN PATHWAYS AND METHODS OF USE

(75) Inventors: Lisa C. Kadyk, San Francisco, CA (US); George Ross Francis, Pacifica, CA (US); Steven Brian Gendreau, San Francisco, CA (US); Emery G. Dora, III, San Francisco, CA (US); Michael R. Costa, San Francisco, CA (US); Kim Lickteig, San Francisco, CA (US)

(73) Assignee: Exelixis, Inc., South San Francisco, CA (US)

( * ) Notice: Subject to any disclaimer, the term of this patent is extended or adjusted under 35 U.S.C. 154(b) by 1174 days.

(21) Appl. No.: 10/535,571

(22) PCT Filed: Nov. 24, 2003

(86) PCT No.: PCT/US03/37730

§ 371 (c)(1),
(2), (4) Date: Jun. 5, 2008

(87) PCT Pub. No.: WO2004/048542

PCT Pub. Date: Jun. 10, 2004

(65) Prior Publication Data

US 2008/0229435 A1 Sep. 18, 2008

Related U.S. Application Data

(60) Provisional application No. 60/429,061, filed on Nov. 25, 2002, provisional application No. 60/437,163, filed on Dec. 30, 2002.

(51) Int. Cl.
*G01N 33/53* (2006.01)

(52) U.S. Cl. .............................. 435/7.1; 435/6; 436/518

(58) Field of Classification Search ........................ None
See application file for complete search history.

(56) References Cited

U.S. PATENT DOCUMENTS 6,183,962 B1 2/2001 Acton

OTHER PUBLICATIONS

International Human Genome Sequencing Consortium. *Homo sapiens* KIAA0551 protein (KIAA0551), mRNA. GI:22041067 Jan. 3, 2003.

Nagase,T., et al. *Homo sapiens* mRNA for KIAA0551 protein, partial cds. GI:20521082 May 10, 2002.

Kawakami,T., et al. *Homo sapiens* cDNA: FLJ22817 fis, clone KAIA3476, highly similar to AF172271 Homo sapiens Traf2 and NCK interacting kinase splice variant 8 (TNIK) mRNA. GI:10439341 Sep. 13, 2003.

Fu,C.A., et al. *Homo sapiens* Traf2 and NCK interacting kinase, splice variant 3 (TNIK) mRNA, complete cds. GI:6110351 Oct. 25, 1999.

Fu,C.A., et at. *Homo sapiens* Traf2 and NCK interacting kinase, splice variant 5 (TNIK) mRNA, complete cds. GI:6110356 Oct. 25, 1999.

Fu,C.A., et at. *Homo sapiens* Traf2 and NCK interacting kinase, splice variant 6 (TNIK) mRNA, complete cds. GI:6110359 Oct. 25, 1999.

Fu,C.A., et al. *Homo sapiens* Traf2 and NCK interacting kinase, splice variant 7 (TNIK) mRNA, complete cds. GI:6110361 Oct. 25, 1999.

Fu,C.A., et al. *Homo sapiens* Traf2 and NCK interacting kinase, splice variant 8 (TNIK) mRNA, complete cds. GI:6110364 Oct. 25, 1999.

Strausberg,R. *Homo sapiens*, clone IMAGE:4651684, mRNA, partial cds. GI:17512195 Dec. 11, 2001.

Fu,C.A., et al. *Homo sapiens* Traf2 and NCK interacting kinase, splice variant 2 (TNIK) mRNA, complete cds. GI:6110349 Oct. 25, 1999.

Strausberg,R.L., et al. *Homo sapiens* TRAF2 and NCK interacting kinase, mRNA (cDNA clone IMAGE:4838784), complete cds. GI:33416309 Jul. 28, 2005.

Wright,J.H., et al *Homo sapiens* mitogen-activated protein kinase kinase kinase kinase 4 (MAP4K4), transcript variant 1, mRNA. GI:22035601 Dec. 20, 2003.

Yao,Z., et al. *Homo sapiens* mitogen-activated protein kinase kinase kinase kinase 4 (MAP4K4), mRNA. GI:4758523 Nov. 1, 2000.

NCBI Annotation Project. *Homo sapiens* mitogen-activated protein kinase kinase kinase kinase 4 (MAP4K4), mRNA. GI: 18553055 Feb. 6, 2002.

Ishikawa,K., et al. *Homo sapiens* mRNA for KIAA0687 protein, partial cds. GI:3327187 Feb. 6, 1999.

Bahr,A., et al. *Homo sapiens* mRNA; cDNA DKFZp434A025 (from clone DKFZp434A025). GI:6808458 Apr. 16, 2005.

Kawabata,A., et al. *Homo sapiens* cDNA: FLJ21957 fis, clone HEP05344. GI:10438179 Sep. 13, 2003.

Ota,T., et al. *Homo sapiens* cDNA FLJ10410 fis, clone NT2RP1000018, highly similar to Homo sapiens mRNA for KIAA0687 protein. GI:7022424 Jan. 30, 2004.

Wright,J.H., et al. *Homo sapiens* mitogen-activated protein kinase kinase kinase kinase 4 (MAP4K4), transcript variant 2, mRNA. GI:22035603 Dec. 21, 2003.

Wright,J.H., et al. *Homo sapiens* mitogen-activated protein kinase kinase kinase kinase 4 (MAP4K4), transcript variant 3, mRNA. GI:22035605 Dec. 21, 2003.

Dan,I., et al. *Homo sapiens* Misshapen/NIK-related kinase (MINK), mRNA. GI:7657334 Dec. 10, 2001.

Strausberg,R.L., et al. *Homo sapiens* misshapen-like kinase 1 (zebrafish), transcript variant 3, mRNA (cDNA clone MGC:21111 IMAGE:4384442), complete cds. GI:21961594 Jul. 9, 2005.

Dan,I., et al. *Homo sapiens* CHRNE, MINK genes for AchR epsilon subunit, GCK family kinase, partial cds. GI:21321027 Jul. 3, 2002.

Ota,T., et al. *Homo sapiens* cDNA FLJ39291 fis, clone OCBBF2012436, highly similar to Homo sapiens mRNA for Misshapen/NIK-related kinase MINK-1. GI:21756143 Jan. 30, 2004.

(Continued)

*Primary Examiner* — Jacob Cheu

(74) *Attorney, Agent, or Firm* — McDonnell Boehnen Hulbert & Berghoff LLP

(57) ABSTRACT

Human MAPK genes are identified as modulators of the Rac, axin, and beta-catenin pathways, and thus are therapeutic targets for disorders associated with defective Rac, axin, and beta-catenin function. Methods for identifying modulators of Rac, axin, and beta-catenin, comprising screening for agents that modulate the activity of MAPK are provided.

12 Claims, No Drawings

OTHER PUBLICATIONS

Hu,Y., et al. *Homo sapiens* misshapen-like kinase 1 (zebrafish) (MINK1), transcript variant 1, mRNA. GI:27436915 Aug. 25, 2005.
Hu,Y., et al. *Homo sapiens* misshapen-like kinase 1 (zebrafish) (MINK1), transcript variant 3, mRNA. GI:27436916 Aug. 25, 2005.
Hu,Y., et al. *Homo sapiens* misshapen-like kinase 1 (zebrafish) (MINK1), transcript variant 2, mRNA. GI:27436918 Aug. 25, 2005.
International Human Genome Sequencing Consortium. *Homo sapiens* similar to NIK-related kinase (LOC203447), mRNA. GI:20549227 Apr. 28, 2003.
NCI-CGAP. on05g09.y5 NCI_CGAP_Kid3 *Homo sapiens* cDNA clone IMAGE:1555840 5' similar to TR:O60298 O60298 KIAA0551 PROTEIN ;, mRNA sequence. GI:5340679 Dec. 13, 1999.
Lauber,J., et al. *Homo sapiens* mRNA; cDNA DKFZp686A17109 (from clone DKFZp686A17109); complete cds. GI:31874847 Apr. 17, 2005.
Fu,C.A., et al. Traf2 and NCK interacting kinase, splice variant 2 [*Homo sapiens*]. GI:6110350 Oct. 25, 1999.
Beausoleil,S.A., et al. mitogen-activated protein kinase kinase kinase kinase 4 isoform 1 [*Homo sapiens*]. GI:22035602 Apr. 23, 2005.
Hu,Y., et al. misshapen/NIK-related kinase isoform 1 [*Homo sapiens*]. GI:7657335 Aug. 25, 2005.
International Human Genome Sequencing Consortium. similar to NIK-related kinase [*Homo sapiens*]. GI:20549228 Apr. 28, 2003.
MacDonald T et al. Expression profiling of medulloblastoma: PDGFRA and the RAS/MAPK pathway as therapeutic targets for metastatic disease. Nature Genetics 29:143-152. 2001.
Li Chaohong et al.: "Cyclic strain stress-induced mitogen-activated protein kinase (MAPK) phosphatase 1 expression in vascular smooth muscle cells is regulated by Ras/Rac-MAPK pathways," Journal of biological Chemistry, vol. 274, No. 36; Sep. 1999, pp. 25273-25850.
Zhang Yi et al.: "Axin forms a complex with MEKK1 and activates c-Jun Nh2-terminal kinase/stress-activated protein kinase through domains distinct from Wnt signaling," Journal of Biological Chemistry, vol. 274, No. 49; Dec. 3, 1999, pp. 35247-35254.
Sun T-Q et al.: "PAR-1 is a Dishevelled-Assoicated kinase and a positive regulator of WNT signalling," Nature Cell Biology, vol. 3, No. 7, Jul. 2001, pp. 628-636.
Macdonald et al.: "Expression profiling of medulloblastoma: PDGFRA and the RAS/MAPK pathway as therapeutic targets for metastatic disease," Nat Genet. 2001, vol. 29. No. 2 pp. 143-152.
Anad_Apte et al.: "Platelet-derived growth factor and fibronectin-stimulated migration are differentially regulated by the Rac and extracellular signal-regulated kinase pathways," Journal Biol. Chem., Oct. 5, 1997, vol. 272, No. 49, pp. 30688-30692.
Liou et al.: "MAP kinase and beta-catenin signaling in HGF induced RPE migration," Mol. Vis., Dec. 20, 2002, vol. 8, pp. 486-493.

SEQUENCE LISTING

```
<160> NUMBER OF SEQ ID NOS: 40

<210> SEQ ID NO 1
<211> LENGTH: 3855
<212> TYPE: DNA
<213> ORGANISM: Homo sapiens

<400> SEQUENCE: 1

aggtagaaga acggtcaagg ctcaaccggc aaagttcccc tgccatgcct cacaaggttg      60

ccaacaggat atctgacccc aacctgcccc caaggtcgga gtccttcagc attagtggag     120

ttcagcctgc tcgaacaccc cccatgctca gaccagtcga tccccagatc ccacatctgg     180

tagctgtaaa atcccaggga cctgccttga ccgcctccca gtcagtgcac gagcagccca     240
```

-continued

```
caaagggcct ctctgggttt caggaggctc tgaacgtgac ctcccaccgc gtggagatgc    300
cacgccagaa ctcagatccc acctcggaaa atcctcctct ccccactcgc attgaaaagt    360
ttgaccgaag ctcttggtta cgacaggaag aagacattcc accaaaggtg cctcaaagaa    420
caacttctat atccccagca ttagccagaa agaattctcc tgggaatggt agtgctctgg    480
gacccagact aggatctcaa cccatcagag caagcaaccc tgatctccgg agaactgagc    540
ccatcttgga gagccccttg cagaggacca gcagtggcag ttcctccagc tccagcaccc    600
ctagctccca gcccagctcc caaggaggct cccagcctgg atcacaagca ggatccagtg    660
aacgcaccag agttcgagcc aacagtaagt cagaaggatc acctgtgctc ccccatgagc    720
ctgcgaaggt gaaaccagaa gaatccaggg acattacccg gcccagtcga ccagctagct    780
acaaaaaagc tatagatgag gatctgacgg cattagccaa agaactaaga gaactccgga    840
ttgaagaaac aaaccgccca atgaagaagg tgactgatta ctcctcctcc agtgaggagt    900
cagaaagtag cgaggaagag gaggaagatg gagagagcga gacccatgat gggacagtgg    960
ctgtcagcga catacccaga ctgataccaa caggagctcc aggcagcaac gagcagtaca   1020
atgtgggaat ggtggggacg catgggctgg agacctctca tgcggacagt ttcagcggca   1080
gtatttcaag agaaggaacc ttgatgatta gagagacgtc tggagagaag aagcgatctg   1140
gccacagtga cagcaatggc tttgctggcc acatcaacct ccctgacctg gtgcagcaga   1200
gccattctcc agctggaacc ccgactgagg gactggggcg cgtctcaacc cattcccagg   1260
agatggactc tgggactgaa tatggcatgg ggagcagcac caaagcctcc ttcacccccct   1320
ttgtggaccc cagagtatac cagacgtctc ccactgatga agatgaagag gatgaggaat   1380
catcagccgc agctctgttt actagcgaac ttcttaggca agaacaggcc aaactcaatg   1440
aagcaagaaa gatttcggtg gtaaatgtaa acccaaccaa cattcggcct catagcgaca   1500
caccagaaat cagaaaatac aagaaacgat tcaactcaga aatactttgt gcagctctgt   1560
ggggtgtaaa ccttctggtg gggactgaaa atggcctgat gcttttggac cgaagtgggc   1620
aaggcaaagt ctataatctg atcaaccgga ggcgatttca gcagatggat gtgctagagg   1680
gactgaatgt ccttgtgaca atttcaggaa agaagaataa gctacgagtt tactatcttt   1740
catggttaag aaacagaata ctacataatg acccagaagt agaaaagaaa caaggctgga   1800
tcactgttgg ggacttggaa ggctgtatac attataaagt tgttaaatat gaaaggatca   1860
aatttttggt gattgcctta aagaatgctg tggaaatata tgcttgggct cctaaaccgt   1920
atcataaatt catggcattt aagtcttttg cagatctcca gcacaagcct ctgctagttg   1980
atctcacggt agaagaaggt caaagattaa aggttatttt tggttcacac actggtttcc   2040
atgtaattga tgttgattca ggaaactctt atgatatcta cataccatct catattcagg   2100
gcaatatcac tcctcatgct attgtcatct tgcctaaaac agatggaatg gaaatgcttg   2160
tttgctatga ggatgagggg gtgtatgtaa acacctatgg ccggataact aaggatgtgg   2220
tgctccaatg gggagaaatg cccacgtctg tggcctacat tcattccaat cagataatgg   2280
gctggggcga gaaagctatt gagatccggt cagtggaaac aggacatttg gatggagtat   2340
ttatgcataa gcgagctcaa aggttaaagt ttctatgtga aagaaatgat aaggtatttt   2400
ttgcatccgt gcgatctgga ggaagtagcc aagtgttttt catgaccctc aacagaaatt   2460
ccatgatgaa ctggtaacag aagagcactt ggcacttatc ttcatggcgt tatttctaat   2520
ttaaaagaac ataactcatg tggacttatg ccagtctaga ggcagaatca gaaggcttgg   2580
ttgaacatat cgctttccct ttttcctctc cctccgcccc tcccagtaca gtccatcttt   2640
```

-continued caatgttgca gcctggttga gaaggagaga aaaaggtggc aggaatttcc aggagatccc 2700
caagaatgct gccttgtctg tggacaaaga tggaccatgt gcccttcgga attagggata 2760
gaaacaaata ttgtgtgctc ttaacgatta agctgtgtta tggtgggttt tcaggttttt 2820
accttttttc tttacccctt tactctgcaa gaatggggaa agaatgcata ctgcgaaaat 2880
gagtctttta aattctgtct gcctactagt tttaagtata tggtatgttg taaaatttcc 2940
aatgatgaga gacagcacaa taaatgtacc ttatctcctt aggctgaagg ccataactac 3000
atagtggagt aatttaagaa ctctcttgcc ttcaccaacc caaaaggttg ctttttgata 3060
gcaactggct aatgaatttt taaaaagaga agaaaaatac tagttttccc ctcttttggg 3120
aaatagattt taaatggcta aactactagc cttaaaacta ctagtctaat aaaatcaact 3180
accacttttg tgaatctgac aggccacatt tttatatggc cctttacaga atggagtgtg 3240
ttgaacagga tactaacgcc attgagttga gctggcctag cgatggaggg acactctaac 3300
acaactttcc ctcagctatt atgcaacaga tcagggaaaa agatgggatg acagatgggg 3360
tcagacagaa agagcttctg ggaaacaagc ttacatagtc tttttaaaa tgcacaaagc 3420 ctcccagcta agaggtcact tggtttgggc ttcattagga ctgagacttt gttgagttct 3480
ttctgggact tggagagtgg atgatattca ggctctgaac attcccagcg ctctcccgag 3540
ggtgccactt tctcaagatg aaaactgtga ctgaaaaaat taataataaa tgtttctgag 3600
ctgcctgtgt tctccctgtg tgggtgagag aagggactag actcctaagc ctgcctcaga 3660
tacaagaggc atcattggct ccaattttag agaacttgaa agcaaggctt tggacaaaat 3720
tttgagaccc taatcacttt accttcctcc aaattaccca acatacggta aacaacattt 3780
gtgcagaagt atgtatgtat ttagttcagg ttgacttgtg tccttataaa ctcttactca 3840
aatgatttga acttt 3855

<210> SEQ ID NO 2
<211> LENGTH: 5727
<212> TYPE: DNA
<213> ORGANISM: Homo sapiens

<400> SEQUENCE: 2
cgcccttagc cgatcggggc gctcagccca cacgcaccgc tgctcggggc ttggagatcc 60
gcgcaggctg ggctcccgga cgcggcggac cgacgcgcgg aggatcggga tccggcgctg 120
tggggctggg gtgggcgggg gaggctgggc ccggggcctc tggcgcgaca cccgcatgag 180
gacgcgagtg aaatagacca aggtggaatt tccaagggaa aagcttcggg gtggttttgg 240
tccatttctc cagcgaagaa gtagacatgg cgagcgactc cccggctcga agcctggatg 300
aaatagatct ctcggctctg agggaccctg cagggatctt tgaattggtg gaacttgttg 360
gaaatggaac atacgggcaa gtttataagg gtcgtcatgt caaaacgggc cagcttgcag 420
ccatcaaggt tatggatgtc acaggggatg aagaggaaga aatcaaacaa gaaattaaca 480
tgttgaagaa atattctcat caccggaata ttgctacata ctatggtgct tttatcaaaa 540
agaacccacc aggcatggat gaccaacttt ggttggtgat ggagttttgt ggtgctggct 600
ctgtcaccga cctgatcaag aacacaaaag gtaacacgtt gaaagaggag tggattgcat 660
acatctgcag ggaaatctta cgggggctga gtcacctgca ccagcataaa gtgattcatc 720
gagatattaa agggcaaaat gtcttgctga ctgaaaatgc agaagttaaa ctagtggact 780
ttggagtcag tgctcagctt gatcgaacag tgggcaggag gaatactttc attggaactc 840
cctactggat ggcaccagaa gttattgcct gtgatgaaaa cccagatgcc acatatgatt 900
tcaagagtga cttgtggtct ttgggtatca ccgccattga aatggcagaa ggtgctcccc 960
ctctctgtga catgcacccc atgagagctc tcttcctcat cccccggaat ccagcgcctc 1020
ggctgaagtc taagaagtgg tcaaaaaaat tccagtcatt tattgagagc tgcttggtaa 1080
agaatcacag ccagcgacca gcaacagaac aattgatgaa gcatccattt atacgagacc 1140
aacctaatga gcgacaggtc cgcattcaac tcaaggacca tattgataga acaaagaaga 1200
agcgaggaga aaaagatgag acagagtatg agtacagtgg aagtgaggaa gaagaggagg 1260
agaatgactc aggagagccc agctccatcc tgaatctgcc aggggagtcg acgctgcgga 1320
gggactttct gaggctgcag ctggccaaca aggagcgttc tgaggcccta cggaggcagc 1380
agctggagca gcagcagcgg gagaatgagg agcacaagcg gcagctgctg gccgagcgtc 1440
agaagcgcat cgaggagcag aaagagcaga ggcggcggct ggaggagcaa caaaggcgag 1500
agaaggagct gcggaagcag caggagaggg agcagcgccg gcactatgag gagcagatgc 1560
gccgggagga ggagaggagg cgtgcggagc atgaacagga atacatcagg cgacagttag 1620
aggaggagca gagacagtta gagatcttgc agcagcagct actgcatgaa caagctctac 1680
ttctggaata taagcgcaaa caattggaag aacagagaca agcagaaaga ctgcagaggc 1740
agctaaagca agaaagagac tacttagttt cccttcagca tcagcggcag gagcagaggc 1800
ctgtggagaa gaagccactg taccattaca aagaaggaat gagtcctagt gagaagccag 1860
catgggccaa ggaggtagaa gaacggtcaa ggctcaaccg gcaaagttcc cctgccatgc 1920
ctcacaaggt tgccaacagg atatctgacc ccaacctgcc cccaaggtcg gagtccttca 1980
gcattagtgg agttcagcct gctcgaacac cccccatgct cagaccagtc gatccccaga 2040
tcccacatct ggtagctgta aaatcccagg gacctgcctt gaccgcctcc cagtcagtgc 2100
acgagcagcc cacaaagggc ctctctgggt ttcaggaggc tctgaacgtg acctcccacc 2160
gcgtggagat gccacgccag aactcagatc ccacctcgga aaatcctcct ctccccactc 2220
gcattgaaaa gtttgaccga agctcttggt tacgacagga agaagacatt ccaccaaagg 2280
tgcctcaaag aacaacttct atatccccag cattagccag aaagaattct cctgggaatg 2340
gtagtgctct gggacccaga ctaggatctc aacccatcag agcaagcaac cctgatctcc 2400
ggagaactga gcccatcttg gagagcccct tgcagaggac cagcagtggc agttcctcca 2460
gctccagcac ccctagctcc cagcccagct cccaaggagg ctcccagcct ggatcacaag 2520
caggatccag tgaacgcacc agagttcgag ccaacagtaa gtcagaagga tcacctgtgc 2580
ttccccatga gcctgccaag gtgaaaccag aagaatccag ggacattacc cggcccagtc 2640
gaccagctag ctacaaaaaa gctatagatg aggatctgac ggcattagcc aaagaactaa 2700
gagaactccg gattgaagaa acaaaccgcc caatgaagaa ggtgactgat tactcctcct 2760
ccagtgagga gtcagaaagt agcgaggaag aggaggaaga tggagagagc gagacccatg 2820
atgggacagt ggctgtcagc gacataccca gactgatacc aacaggagct ccaggcagca 2880
acgagcagta caatgtggga atggtgggga cgcatgggct ggagacctct catgcggaca 2940
gtttcagcgg cagtatttca agagaaggaa ccttgatgat tagagagacg tctggagaga 3000
agaagcgatc tggccacagt gacagcaatg gctttgctgg ccacatcaac ctccctgacc 3060
tggtgcagca gagccattct ccagctggaa ccccgactga gggactgggg cgcgtctcaa 3120
cccattccca ggagatggac tctgggactg aatatggcat ggggagcagc accaaagcct 3180
ccttcacccc ctttgtggac cccagagtat accagacgtc tcccactgat gaagatgaag 3240
aggatgagga atcatcagcc gcagctctgt ttactagcga acttcttagg caagaacagg 3300

-continued

```
ccaaactcaa tgaagcaaga aagatttcgg tggtaaatgt aaacccaacc aacattcggc   3360
ctcatagcga cacaccagaa atcagaaaat acaagaaacg attcaactca gaaatacttt   3420
gtgcagctct gtggggtgta aaccttctgg tggggactga aaatggcctg atgcttttgg   3480
accgaagtgg gcaaggcaaa gtctataatc tgatcaaccg gaggcgattt cagcagatgg   3540
atgtgctaga gggactgaat gtccttgtga caatttcagg aaagaagaat aagctacgag   3600
tttactatct ttcatggtta agaaacagaa tactacataa tgacccagaa gtagaaaaga   3660
aacaaggctg gatcactgtt ggggacttgg aaggctgtat acattataaa gttgttaaat   3720
atgaaaggat caaatttttg gtgattgcct taaagaatgc tgtggaaata tatgcttggg   3780
ctcctaaacc gtatcataaa ttcatggcat ttaagtcttt tgcagatctc cagcacaagc   3840
ctctgctagt tgatctcacg gtagaagaag gtcaaagatt aaaggttatt tttggttcac   3900
acactggttt ccatgtaatt gatgttgatt caggaaactc ttatgatatc tacataccat   3960
ctcatattca gggcaatatc actcctcatg ctattgtcat cttgcctaaa acagatggaa   4020
tggaaatgct tgtttgctat gaggatgagg gggtgtatgt aaacacctat ggccggataa   4080
ctaaggatgt ggtgctccaa tggggagaaa tgcccacgtc tgtggcctac attcattcca   4140
atcagataat gggctggggc gagaaagcta ttgagatccg gtcagtggaa acaggacatt   4200
tggatggagt atttatgcat aagcgagctc aaaggttaaa gtttctatgt gaaagaaatg   4260
ataaggtatt ttttgcatcc gtgcgatctg gaggaagtag ccaagtgttt ttcatgaccc   4320
tcaacagaaa ttccatgatg aactggtaac agaagagcac ttggcactta tcttcatggc   4380
gttatttcta atttaaaaga acataactca tgtggactta tgccagtcta gaggcagaat   4440
cagaaggctt ggttgaacat atcgctttcc ctttttcctc tccctccgcc cctcccagta   4500
cagtccatct ttcaatgttg cagcctggtt gagaaggaga gaaaaaggtg gcaggaattt   4560
ccaggagatc cccaagaatg ctgccttgtc tgtggacaaa gatggaccat gtgcccttcg   4620
gaattaggga tagaaacaaa tattgtgtgc tcttaacgat taagctgtgt tatggtgggt   4680
tttcaggttt ttaccttttt tctttacccc tttactctgc aagaatgggg aaagaatgca   4740
tactgcgaaa atgagtcttt taaattctgt ctgcctacta gttttaagta tatggtatgt   4800
tgtaaaattt ccaatgatga gagacagcac aataaatgta ccttatctcc ttaggctgaa   4860
ggccataact acatagtgga gtaatttaag aactctcttg ccttcaccaa cccaaaaggt   4920
tgctttttga tagcaactgg ctaatgaatt tttaaaaaga gaagaaaaat actagttttc   4980
ccctcttttg ggaaatagat tttaaatggc taaactacta gccttaaaac tactagtcta   5040
ataaaatcaa ctaccacttt tgtgaatctg acaggccaca tttttatatg gccctttaca   5100
gaatggagtg tgttgaacag gatactaacg ccattgagtt gagctggcct agcgatggag   5160
ggacactcta acacaacttt ccctcagcta ttatgcaaca gatcagggaa aaagatggga   5220
tgacagatgg ggtcagacag aaagagcttc tgggaaacaa gcttacatag tcttttttaa   5280
aatgcacaaa gcctcccagc taagaggtca cttggtttgg gcttcattag gactgagact   5340
ttgttgagtt ctttctggga cttggagagt ggatgatatt caggctctga acattcccag   5400
cgctctcccg agggtgccac tttctcaaga tgaaaactgt gactgaaaaa attaataata   5460
aatgtttctg agctgcctgt gttctccctg tgtgggtgag agaagggact agactcctaa   5520
gcctgcctca gatacaagag gcatcattgg ctccaatttt agagaacttg aaagcaaggc   5580
tttggacaaa attttgagac cctaatcact ttaccttcct ccaaattacc caacatacgg   5640
taaacaacat ttgtgcagaa gtatgtatgt atttagttca ggttgacttg tgtccttata   5700
```

-continued aactcttact caaatgattt gaacttt 5727

<210> SEQ ID NO 3
<211> LENGTH: 1084
<212> TYPE: DNA
<213> ORGANISM: Homo sapiens

<400> SEQUENCE: 3
tcacatctgt gcctaaggct cctattgaca aggactctct gcattaggta gtaaataact 60
agatgtatga atgctgctaa ctttataaaa gaaaactgta atttcattac cagaagtaca 120
atgatttaat tattatgtca gagcttctac attcattagt ttatatttac ctacttgccc 180
attagtgtat atttacaagt cacagtttct taaattttat agggactctc gatgcagaag 240
attaaagttc atgaaaagtc agtcttaggg tgcttcttaa atttacaggt gtaaaccttc 300
tggtggggac tgaaaatggc ctgatgcttt tggaccgaag tgggcaaggc aaagtctata 360
atctgatcaa ccggaggcga tttcagcaga tggatgtgct agagggactg aatgtccttg 420
tgacaatttc aggaaagaag aataagctac gagtttacta tctttcatgg ttaagaaaca 480
gaatactaca taatgaccca gaagtagaaa agaaacaagg ctggatcact gttggggact 540
tggaaggctg tatacattat aaagttgtta aatatgaaag gatcaaattt ttggtgattg 600
ccttaaagaa tgctgtggaa atatatgctt gggctcctaa accgtatcat aaattcatgg 660
catttaagtc ttttgcagat ctccagcaca agcctctgct agttgatctc acggtagaag 720
aaggtcaaag attaaaggtt atttttggtt cacacactgg tttccatgta attgatgttg 780
attcaggaaa ctcttatgat atctacatac catctcatat tcagggcaat atcactcctc 840
atgctattgt catcttgcct aaaacagatg gaatggaaat gcttgtttgc tatgaggatg 900
agggggtgta tgtaaacacc tatggccgga taactaagga tgtggtgctc caatggggag 960
aaatgcccac gtctgtgggt aggttaacca ttccttatct ccttcagcag ttacaccccc 1020
caaatgaaac gaaaatcaag aaatgtgaaa caaccatttg attccacaaa aaaaaaaaaa 1080
aaaa 1084

<210> SEQ ID NO 4
<211> LENGTH: 3918
<212> TYPE: DNA
<213> ORGANISM: Homo sapiens

<400> SEQUENCE: 4
atggcgagcg actccccggc tcgaagcctg gatgaaatag atctctcggc tctgagggac 60
cctgcaggga tctttgaatt ggtggaactt gttggaaatg gaacatacgg gcaagtttat 120
aagggtcgtc atgtcaaaac gggccagctt gcagccatca aggttatgga tgtcacaggg 180
gatgaagagg aagaaatcaa acaagaaatt aacatgttga agaaatattc tcatcaccgg 240
aatattgcta catactatgg tgcttttatc aaaaagaacc caccaggcat ggatgaccaa 300
ctttggttgg tgatggagtt ttgtggtgct ggctctgtca ccgacctgat caagaacaca 360
aaaggtaaca cgttgaaaga ggagtggatt gcatacatct gcagggaaat cttacggggg 420
ctgagtcacc tgcaccagca taaagtgatt catcgagata ttaaagggca aaatgtcttg 480
ctgactgaaa atgcagaagt taaactagtg gactttggag tcagtgctca gcttgatcga 540
acagtgggca ggaggaatac tttcattgga actccctact ggatggcacc agaagttatt 600
gcctgtgatg aaaacccaga tgccacatat gatttcaaga gtgacttgtg gtctttgggt 660
atcaccgcca ttgaaatggc agaaggtgct ccccctctct gtgacatgca ccccatgaga 720

-continued

```
gctctcttcc tcatcccccg gaatccagcg cctcggctga agtctaagaa gtggtcaaaa    780
aaattccagt catttattga gagctgcttg gtaaagaatc acagccagcg accagcaaca    840
gaacaattga tgaagcatcc atttatacga gaccaaccta atgagcgaca ggtccgcatt    900
caactcaagg accatattga tagaacaaag aagaagcgag gagaaaaaga tgagacagag    960
tatgagtaca gtggaagtga ggaagaagag gaggagaatg actcaggaga gcccagctcc   1020
atcctgaatc tgccagggga gtcgacgctg cggagggact ttctgaggct gcagctggcc   1080
aacaaggagc gttctgaggc cctacggagg cagcagctgg agcagcagca gcgggagaat   1140
gaggagcaca agcggcagct gctggccgag cgtcagaagc gcatcgagga gcagaaagag   1200
cagaggcggc ggctggagga gcaacaaagg cgagagaagg agctgcggaa gcagcaggag   1260
agggagcagc gccggcacta tgaggagcag atgcgccggg aggaggagag gaggcgtgcg   1320
gagcatgaac aggaatacat caggcgacag ttagaggagg agcagagaca gttagagatc   1380
ttgcagcagc agctactgca tgaacaagct ctacttctgg aatataagcg caaacaattg   1440
gaagaacaga gacaagcaga aagactgcag aggcagctaa agcaagaaag agactactta   1500
gtttcccttc agcatcagcg gcaggagcag aggcctgtgg agaagaagcc actgtaccat   1560
tacaaagaag gaatgagtcc tagtgagaag ccagcatggg ccaaggagat cccacatctg   1620
gtagctgtaa aatcccaggg acctgccttg accgcctccc agtcagtgca cgagcagccc   1680
acaaagggcc tctctgggtt tcaggaggct ctgaacgtga cctcccaccg cgtggagatg   1740
ccacgccaga actcagatcc cacctcggaa aatcctcctc tccccactcg cattgaaaag   1800
tttgaccgaa gctcttggtt acgacaggaa gaagacattc caccaaaggt gcctcaaaga   1860
acaacttcta tatccccagc attagccaga aagaattctc ctgggaatgg tagtgctctg   1920
ggacccagac taggatctca acccatcaga gcaagcaacc ctgatctccg gagaactgag   1980
cccatcttgg agagcccctt gcagaggacc agcagtggca gttcctccag ctccagcacc   2040
cctagctccc agcccagctc ccaaggaggc tcccagcctg gatcacaagc aggatccagt   2100
gaacgcacca gagttcgagc caacagtaag tcagaaggat cacctgtgct tccccatgag   2160
cctgccaagg tgaaaccaga agaatccagg gacattaccc ggcccagtcg accagctagc   2220
tacaaaaaag ctatagatga ggatctgacg gcattagcca aagaactaag agaactccgg   2280
attgaagaaa caaaccgccc aatgaagaag gtgactgatt actcctcctc cagtgaggag   2340
tcagaaagta gcgaggaaga ggaggaagat ggagagagcg agacccatga tgggacagtg   2400
gctgtcagcg acatacccag actgatacca acaggagctc caggcagcaa cgagcagtac   2460
aatgtgggaa tggtggggac gcatgggctg gagacctctc atgcggacag tttcagcggc   2520
agtatttcaa gagaaggaac cttgatgatt agagagacgt ctggagagaa gaagcgatct   2580
ggccacagtg acagcaatgg ctttgctggc cacatcaacc tccctgacct ggtgcagcag   2640
agccattctc cagctggaac ccgactgag ggactggggc gcgtctcaac ccattcccag   2700
gagatggact ctgggactga atatggcatg gggagcagca ccaaagcctc cttcaccccc   2760
tttgtggacc ccagagtata ccagacgtct cccactgatg aagatgaaga ggatgaggaa   2820
tcatcagccg cagctctgtt tactagcgaa cttcttaggc aagaacaggc caaactcaat   2880
gaagcaagaa agatttcggt ggtaaatgta aacccaacca acattcggcc tcatagcgac   2940
acaccagaaa tcagaaaata caagaaacga ttcaactcag aaatactttg tgcagctctg   3000
tggggtgtaa accttctggt ggggactgaa aatggcctga tgcttttgga ccgaagtggg   3060
caaggcaaag tctataatct gatcaaccgg aggcgatttc agcagatgga tgtgctagag   3120
```

-continued

```
ggactgaatg tccttgtgac aatttcagga aagaagaata agctacgagt ttactatctt   3180
tcatggttaa gaaacagaat actacataat gacccagaag tagaaaagaa acaaggctgg   3240
atcactgttg gggacttgga aggctgtata cattataaag ttgttaaata tgaaaggatc   3300
aaatttttgg tgattgcctt aaagaatgct gtggaaatat atgcttgggc tcctaaaccg   3360
tatcataaat tcatggcatt taagtctttt gcagatctcc agcacaagcc tctgctagtt   3420
gatctcacgg tagaagaagg tcaaagatta aaggttattt ttggttcaca cactggtttc   3480
catgtaattg atgttgattc aggaaactct tatgatatct acataccatc tcatattcag   3540
ggcaatatca ctcctcatgc tattgtcatc ttgcctaaaa cagatggaat ggaaatgctt   3600
gtttgctatg aggatgaggg ggtgtatgta aacacctatg gccggataac taaggatgtg   3660
gtgctccaat ggggagaaat gcccacgtct gtggcctaca ttcattccaa tcagataatg   3720
ggctggggcg agaaagctat tgagatccgg tcagtggaaa caggacattt ggatggagta   3780
tttatgcata agcgagctca aaggttaaag tttctatgtg aaagaaatga taaggtattt   3840
tttgcatccg tgcgatctgg aggaagtagc caagtgtttt tcatgaccct caacagaaat   3900
tccatgatga actggtaa                                                 3918
```

<210> SEQ ID NO 5
<211> LENGTH: 3831
<212> TYPE: DNA
<213> ORGANISM: Homo sapiens

<400> SEQUENCE: 5

```
atggcgagcg actccccggc tcgaagcctg gatgaaatag atctctcggc tctgagggac     60
cctgcaggga tctttgaatt ggtggaactt gttggaaatg gaacatacgg gcaagtttat    120
aagggtcgtc atgtcaaaac gggccagctt gcagccatca aggttatgga tgtcacaggg    180
gatgaagagg aagaaatcaa acaagaaatt aacatgttga agaaatattc tcatcaccgg    240
aatattgcta catactatgg tgcttttatc aaaaagaacc caccaggcat ggatgaccaa    300
ctttggttgg tgatggagtt ttgtggtgct ggctctgtca ccgacctgat caagaacaca    360
aaaggtaaca cgttgaaaga ggagtggatt gcatacatct gcagggaaat cttacggggg    420
ctgagtcacc tgcaccagca taaagtgatt catcgagata ttaaagggca aaatgtcttg    480
ctgactgaaa atgcagaagt taaactagtg gactttggag tcagtgctca gcttgatcga    540
acagtgggca ggaggaatac tttcattgga actccctact ggatggcacc agaagttatt    600
gcctgtgatg aaaacccaga tgccacatat gatttcaaga gtgacttgtg gtctttgggt    660
atcaccgcca ttgaaatggc agaaggtgct cccccctctct gtgacatgca ccccatgaga    720
gctctcttcc tcatccccccg gaatccagcg cctcggctga agtctaagaa gtggtcaaaa    780
aaattccagt catttattga gagctgcttg gtaaagaatc acagccagcg accagcaaca    840
gaacaattga tgaagcatcc atttatacga gaccaaccta atgagcgaca ggtccgcatt    900
caactcaagg accatattga tagaacaaag aagaagcgag gagaaaaaga tgagacagag    960
tatgagtaca gtggaagtga ggaagaagag gaggagaatg actcaggaga gcccagctcc   1020
atcctgaatc tgccagggga gtcgacgctg cggagggact ttctgaggct gcagctggcc   1080
aacaaggagc gttctgaggc cctacggagg cagcagctgg agcagcagca gcgggagaat   1140
gaggagcaca agcggcagct gctggccgag cgtcagaagc gcatcgagga gcagaaagag   1200
cagaggcggc ggctggagga gcaacaaagg cgagagaagg agctgcggaa gcagcaggag   1260
agggagcagc gccggcacta tgaggagcag atgcgccggg aggaggagag gaggcgtgcg   1320
```

-continued

```
gagcatgaac aggaatataa gcgcaaacaa ttggaagaac agagacaagc agaaagactg   1380
cagaggcagc taaagcaaga aagagactac ttagtttccc ttcagcatca gcggcaggag   1440
cagaggcctg tggagaagaa gccactgtac cattacaaag aaggaatgag tcctagtgag   1500
aagccagcat gggccaagga gatcccacat ctggtagctg taaaatccca gggacctgcc   1560
ttgaccgcct cccagtcagt gcacgagcag cccacaaagg gcctctctgg gtttcaggag   1620
gctctgaacg tgacctccca ccgcgtggag atgccacgcc agaactcaga tcccacctcg   1680
gaaaatcctc ctctccccac tcgcattgaa aagtttgacc gaagctcttg gttacgacag   1740
gaagaagaca ttccaccaaa ggtgcctcaa agaacaactt ctatatcccc agcattagcc   1800
agaaagaatt ctcctgggaa tggtagtgct ctgggaccca gactaggatc tcaacccatc   1860
agagcaagca accctgatct ccggagaact gagcccatct tggagagccc cttgcagagg   1920
accagcagtg gcagttcctc cagctccagc acccctagct cccagcccag ctcccaagga   1980
ggctcccagc ctggatcaca agcaggatcc agtgaacgca ccagagttcg agccaacagt   2040
aagtcagaag gatcacctgt gcttccccat gagcctgcca aggtgaaacc agaagaatcc   2100
agggacatta cccggcccag tcgaccagct agctacaaaa aagctataga tgaggatctg   2160
acggcattag ccaaagaact aagagaactc cggattgaag aaacaaaccg cccaatgaag   2220
aaggtgactg attactcctc ctccagtgag gagtcagaaa gtagcgagga agaggaggaa   2280
gatggagaga gcgagaccca tgatgggaca gtggctgtca gcgacatacc cagactgata   2340
ccaacaggag ctccaggcag caacgagcag tacaatgtgg gaatggtggg gacgcatggg   2400
ctggagacct ctcatgcgga cagtttcagc ggcagtattt caagagaagg aaccttgatg   2460
attagagaga cgtctggaga gaagaagcga tctggccaca gtgacagcaa tggctttgct   2520
ggccacatca acctccctga cctggtgcag cagagccatt ctccagctgg aaccccgact   2580
gagggactgg ggcgcgtctc aacccattcc caggagatgg actctgggac tgaatatggc   2640
atggggagca gcaccaaagc ctccttcacc ccctttgtgg accccagagt ataccagacg   2700
tctcccactg atgaagatga agaggatgag gaatcatcag ccgcagctct gtttactagc   2760
gaacttctta ggcaagaaca ggccaaactc aatgaagcaa gaaagatttc ggtggtaaat   2820
gtaaacccaa ccaacattcg gcctcatagc gacacaccag aaatcagaaa atacaagaaa   2880
cgattcaact cagaaatact tgtgcagct ctgtggggtg taaaccttct ggtggggact    2940
gaaaatggcc tgatgctttt ggaccgaagt gggcaaggca aagtctataa tctgatcaac   3000
cggaggcgat ttcagcagat ggatgtgcta gagggactga atgtccttgt gacaatttca   3060
ggaaagaaga ataagctacg agtttactat ctttcatggt taagaaacag aatactacat   3120
aatgacccag aagtagaaaa gaaacaaggc tggatcactg ttggggactt ggaaggctgt   3180
atacattata aagttgttaa atatgaaagg atcaaatttt tggtgattgc cttaaagaat   3240
gctgtggaaa tatatgcttg ggctcctaaa ccgtatcata aattcatggc atttaagtct   3300
tttgcagatc tccagcacaa gcctctgcta gttgatctca cggtagaaga aggtcaaaga   3360
ttaaaggtta tttttggttc acacactggt ttccatgtaa ttgatgttga ttcaggaaac   3420
tcttatgata tctacatacc atctcatatt cagggcaata tcactcctca tgctattgtc   3480
atcttgccta aaacagatgg aatggaaatg cttgtttgct atgaggatga gggggtgtat   3540
gtaaacacct atggccggat aactaaggat gtggtgctcc aatggggaga aatgcccacg   3600
tctgtggcct acattcattc caatcagata atgggctggg gcgagaaagc tattgagatc   3660
cggtcagtgg aaacaggaca tttggatgga gtatttatgc ataagcgagc tcaaaggtta   3720
```

aagtttctat gtgaaagaaa tgataaggta ttttttgcat ccgtgcgatc tggaggaagt 3780
agccaagtgt ttttcatgac cctcaacaga aattccatga tgaactggta a 3831

<210> SEQ ID NO 6
<211> LENGTH: 3972
<212> TYPE: DNA
<213> ORGANISM: Homo sapiens

<400> SEQUENCE: 6
atggcgagcg actccccggc tcgaagcctg gatgaaatag atctctcggc tctgagggac 60
cctgcaggga tctttgaatt ggtggaactt gttggaaatg gaacatacgg gcaagtttat 120
aagggtcgtc atgtcaaaac gggccagctt gcagccatca aggttatgga tgtcacaggg 180
gatgaagagg aagaaatcaa acaagaaatt aacatgttga agaaatattc tcatcaccgg 240
aatattgcta catactatgg tgcttttatc aaaaagaacc caccaggcat ggatgaccaa 300
ctttggttgg tgatggagtt ttgtggtgct ggctctgtca ccgacctgat caagaacaca 360
aaaggtaaca cgttgaaaga ggagtggatt gcatacatct gcagggaaat cttacggggg 420
ctgagtcacc tgcaccagca taaagtgatt catcgagata ttaaagggca aaatgtcttg 480
ctgactgaaa atgcagaagt taaactagtg gactttggag tcagtgctca gcttgatcga 540
acagtgggca ggaggaatac tttcattgga actccctact ggatggcacc agaagttatt 600
gcctgtgatg aaaacccaga tgccacatat gatttcaaga gtgacttgtg gtctttgggt 660
atcaccgcca ttgaaatggc agaaggtgct cccctctct gtgacatgca ccccatgaga 720
gctctcttcc tcatcccccg gaatccagcg cctcggctga agtctaagaa gtggtcaaaa 780
aaattccagt catttattga gagctgcttg gtaaagaatc acagccagcg accagcaaca 840
gaacaattga tgaagcatcc atttatacga gaccaaccta atgagcgaca ggtccgcatt 900
caactcaagg accatattga tagaacaaag aagaagcgag gagaaaaaga tgagacagag 960
tatgagtaca gtggaagtga ggaagaagag gaggagaatg actcaggaga gcccagctcc 1020
atcctgaatc tgccagggga gtcgacgctg cggagggact ttctgaggct gcagctggcc 1080
aacaaggagc gttctgaggc cctacggagg cagcagctgg agcagcagca gcgggagaat 1140
gaggagcaca agcggcagct gctggccgag cgtcagaagc gcatcgagga gcagaaagag 1200
cagaggcggc ggctggagga gcaacaaagg cgagagaagg agctgcggaa gcagcaggag 1260
agggagcagc gccggcacta tgaggagcag atgcgccggg aggaggagag gaggcgtgcg 1320
gagcatgaac aggaatataa gcgcaaacaa ttggaagaac agagacaagc agaaagactg 1380
cagaggcagc taaagcaaga aagagactac ttagtttccc ttcagcatca gcggcaggag 1440
cagaggcctg tggagaagaa gccactgtac cattacaaag aaggaatgag tcctagtgag 1500
aagccagcat gggccaagga ggtagaagaa cggtcaaggc tcaaccggca aagttcccct 1560
gccatgcctc acaaggttgc caacaggata tctgacccca acctgccccc aaggtcggag 1620
tccttcagca ttagtggagt tcagcctgct cgaacacccc ccatgctcag accagtcgat 1680
ccccagatcc cacatctggt agctgtaaaa tcccagggac ctgccttgac cgcctcccag 1740
tcagtgcacg agcagcccac aaagggcctc tctgggtttc aggaggctct gaacgtgacc 1800
tcccaccgcg tggagatgcc acgccagaac tcagatccca cctcggaaaa tcctcctctc 1860
cccactcgca ttgaaaagtt tgaccgaagc tcttggttac gacaggaaga agacattcca 1920
ccaaaggtgc ctcaaagaac aacttctata tccccagcat tagccagaaa gaattctcct 1980
gggaatggta gtgctctggg acccagacta ggatctcaac ccatcagagc aagcaaccct 2040

-continued

```
gatctccgga gaactgagcc catcttggag agccccttgc agaggaccag cagtggcagt   2100
tcctccagct ccagcacccc tagctcccag cccagctccc aaggaggctc ccagcctgga   2160
tcacaagcag gatccagtga acgcaccaga gttcgagcca acagtaagtc agaaggatca   2220
cctgtgcttc cccatgagcc tgccaaggtg aaaccagaag aatccaggga cattacccgg   2280
cccagtcgac cagctgatct gacggcatta gccaaagaac taagagaact ccggattgaa   2340
gaaacaaacc gcccaatgaa gaaggtgact gattactcct cctccagtga ggagtcagaa   2400
agtagcgagg aagaggagga agatggagag agcgagaccc atgatgggac agtggctgtc   2460
agcgacatac ccagactgat accaacagga gctccaggca gcaacgagca gtacaatgtg   2520
ggaatggtgg ggacgcatgg gctggagacc tctcatgcgg acagtttcag cggcagtatt   2580
tcaagagaag gaaccttgat gattagagag acgtctggag agaagaagcg atctggccac   2640
agtgacagca atggctttgc tggccacatc aacctccctg acctggtgca gcagagccat   2700
tctccagctg gaaccccgac tgagggactg gggcgcgtct caacccattc ccaggagatg   2760
gactctggga ctgaatatgg catggggagc agcaccaaag cctccttcac cccctttgtg   2820
gaccccagag tataccagac gtctcccact gatgaagatg aagaggatga ggaatcatca   2880
gccgcagctc tgtttactag cgaacttctt aggcaagaac aggccaaact caatgaagca   2940
agaaagattt cggtggtaaa tgtaaaccca accaacattc ggcctcatag cgacacacca   3000
gaaatcagaa aatacaagaa acgattcaac tcagaaatac tttgtgcagc tctgtggggt   3060
gtaaaccttc tggtggggac tgaaaatggc ctgatgcttt tggaccgaag tgggcaaggc   3120
aaagtctata atctgatcaa ccggaggcga tttcagcaga tggatgtgct agagggactg   3180
aatgtccttg tgacaatttc aggaaagaag aataagctac gagtttacta tctttcatgg   3240
ttaagaaaca gaatactaca taatgaccca gaagtagaaa agaaacaagg ctggatcact   3300
gttggggact tggaaggctg tatacattat aaagttgtta aatatgaaag gatcaaattt   3360
ttggtgattg ccttaaagaa tgctgtggaa atatatgctt gggctcctaa accgtatcat   3420
aaattcatgg catttaagtc ttttgcagat ctccagcaca agcctctgct agttgatctc   3480
acggtagaag aaggtcaaag attaaaggtt atttttggtt cacacactgg tttccatgta   3540
attgatgttg attcaggaaa ctcttatgat atctacatac catctcatat tcagggcaat   3600
atcactcctc atgctattgt catcttgcct aaaacagatg gaatggaaat gcttgtttgc   3660
tatgaggatg agggggtgta tgtaaacacc tatggccgga taactaagga tgtggtgctc   3720
caatggggag aaatgcccac gtctgtggcc tacattcatt ccaatcagat aatgggctgg   3780
ggcgagaaag ctattgagat ccggtcagtg gaaacaggac atttggatgg agtatttatg   3840
cataagcgag ctcaaaggtt aaagtttcta tgtgaaagaa atgataaggt atttttttgca   3900 tccgtgcgat ctggaggaag tagccaagtg tttttcatga ccctcaacag aaattccatg   3960
atgaactggt aa                                                        3972

<210> SEQ ID NO 7
<211> LENGTH: 3894
<212> TYPE: DNA
<213> ORGANISM: Homo sapiens

<400> SEQUENCE: 7
atggcgagcg actccccggc tcgaagcctg gatgaaatag atctctcggc tctgagggac     60
cctgcaggga tctttgaatt ggtggaactt gttggaaatg gaacatacgg gcaagtttat    120
aagggtcgtc atgtcaaaac gggccagctt gcagccatca aggttatgga tgtcacaggg    180
```

-continued

```
gatgaagagg aagaaatcaa acaagaaatt aacatgttga agaaatattc tcatcaccgg    240
aatattgcta catactatgg tgcttttatc aaaaagaacc caccaggcat ggatgaccaa    300
ctttggttgg tgatggagtt ttgtggtgct ggctctgtca ccgacctgat caagaacaca    360
aaaggtaaca cgttgaaaga ggagtggatt gcatacatct gcagggaaat cttacggggg    420
ctgagtcacc tgcaccagca taaagtgatt catcgagata ttaaagggca aaatgtcttg    480
ctgactgaaa atgcagaagt taaactagtg gactttggag tcagtgctca gcttgatcga    540
acagtgggca ggaggaatac tttcattgga actccctact ggatggcacc agaagttatt    600
gcctgtgatg aaaacccaga tgccacatat gatttcaaga gtgacttgtg gtctttgggt    660
atcaccgcca ttgaaatggc agaaggtgct ccccctctct gtgacatgca ccccatgaga    720
gctctcttcc tcatcccccg gaatccagcg cctcggctga agtctaagaa gtggtcaaaa    780
aaattccagt catttattga gagctgcttg gtaaagaatc acagccagcg accagcaaca    840
gaacaattga tgaagcatcc atttatacga gaccaaccta atgagcgaca ggtccgcatt    900
caactcaagg accatattga tagaacaaag aagaagcgag gagaaaaaga tgagacagag    960
tatgagtaca gtggaagtga ggaagaagag gaggagaatg actcaggaga gcccagctcc   1020
atcctgaatc tgccagggga gtcgacgctg cggagggact ttctgaggct gcagctggcc   1080
aacaaggagc gttctgaggc cctacggagg cagcagctgg agcagcagca gcgggagaat   1140
gaggagcaca agcggcagct gctggccgag cgtcagaagc gcatcgagga gcagaaagag   1200
cagaggcggc ggctggagga gcaacaaagg cgagagaagg agctgcggaa gcagcaggag   1260
agggagcagc gccggcacta tgaggagcag atgcgccggg aggaggagag gaggcgtgcg   1320
gagcatgaac aggaatacat caggcgacag ttagaggagg agcagagaca gttagagatc   1380
ttgcagcagc agctactgca tgaacaagct ctacttctgg aatataagcg caaacaattg   1440
gaagaacaga gacaagcaga aagactgcag aggcagctaa agcaagaaag agactactta   1500
gtttcccttc agcatcagcg gcaggagcag aggcctgtgg agaagaagcc actgtaccat   1560
tacaaagaag gaatgagtcc tagtgagaag ccagcatggg ccaaggagat cccacatctg   1620
gtagctgtaa aatcccaggg acctgccttg accgcctccc agtcagtgca cgagcagccc   1680
acaaagggcc tctctgggtt tcaggaggct ctgaacgtga cctcccaccg cgtggagatg   1740
ccacgccaga actcagatcc cacctcggaa aatcctcctc tccccactcg cattgaaaag   1800
tttgaccgaa gctcttggtt acgacaggaa gaagacattc caccaaaggt gcctcaaaga   1860
acaacttcta tatccccagc attagccaga aagaattctc ctgggaatgg tagtgctctg   1920
ggacccagac taggatctca acccatcaga gcaagcaacc ctgatctccg gagaactgag   1980
cccatcttgg agagcccctt gcagaggacc agcagtggca gttcctccag ctccagcacc   2040
cctagctccc agcccagctc ccaaggaggc tcccagcctg gatcacaagc aggatccagt   2100
gaacgcacca gagttcgagc caacagtaag tcagaaggat cacctgtgct tccccatgag   2160
cctgccaagg tgaaaccaga agaatccagg gacattaccc ggcccagtcg accagctgat   2220
ctgacggcat tagccaaaga actaagagaa ctccggattg aagaaacaaa ccgcccaatg   2280
aagaaggtga ctgattactc ctcctccagt gaggagtcag aaagtagcga ggaagaggag   2340
gaagatggag agagcgagac ccatgatggg acagtggctg tcagcgacat acccagactg   2400
ataccaacag gagctccagg cagcaacgag cagtacaatg tgggaatggt ggggacgcat   2460
gggctggaga cctctcatgc ggacagtttc agcggcagta tttcaagaga aggaaccttg   2520
atgattagag agacgtctgg agagaagaag cgatctggcc acagtgacag caatggcttt   2580
```

gctggccaca tcaacctccc tgacctggtg cagcagagcc attctccagc tggaaccccg 2640
actgagggac tggggcgcgt ctcaacccat tcccaggaga tggactctgg gactgaatat 2700
ggcatgggga gcagcaccaa agcctccttc accccctttg tggaccccag agtataccag 2760
acgtctccca ctgatgaaga tgaagaggat gaggaatcat cagccgcagc tctgtttact 2820
agcgaacttc ttaggcaaga acaggccaaa ctcaatgaag caagaaagat ttcggtggta 2880
aatgtaaacc caaccaacat tcggcctcat agcgacacac cagaaatcag aaaatacaag 2940
aaacgattca actcagaaat actttgtgca gctctgtggg gtgtaaacct tctggtgggg 3000
actgaaaatg gcctgatgct tttggaccga agtgggcaag gcaaagtcta taatctgatc 3060
aaccggaggc gatttcagca gatggatgtg ctagagggac tgaatgtcct tgtgacaatt 3120
tcaggaaaga agaataagct acgagtttac tatctttcat ggttaagaaa cagaatacta 3180
cataatgacc cagaagtaga aaagaaacaa ggctggatca ctgttgggga cttggaaggc 3240
tgtatacatt ataaagttgt taaatatgaa aggatcaaat tttggtgat tgccttaaag 3300 aatgctgtgg aaatatatgc ttgggctcct aaaccgtatc ataaattcat ggcatttaag 3360
tcttttgcag atctccagca caagcctctg ctagttgatc tcacggtaga agaaggtcaa 3420
agattaaagg ttatttttgg ttcacacact ggtttccatg taattgatgt tgattcagga 3480
aactcttatg atatctacat accatctcat attcagggca atatcactcc tcatgctatt 3540
gtcatcttgc ctaaaacaga tggaatggaa atgcttgttt gctatgagga tgagggggtg 3600
tatgtaaaca cctatggccg gataactaag gatgtggtgc tccaatgggg agaaatgccc 3660
acgtctgtgg cctacattca ttccaatcag ataatgggct ggggcgagaa agctattgag 3720
atccggtcag tggaaacagg acatttggat ggagtattta tgcataagcg agctcaaagg 3780
ttaaagtttc tatgtgaaag aaatgataag gtatttttg catccgtgcg atctggagga 3840
agtagccaag tgtttttcat gaccctcaac agaaattcca tgatgaactg gtaa 3894

<210> SEQ ID NO 8
<211> LENGTH: 3807
<212> TYPE: DNA
<213> ORGANISM: Homo sapiens

<400> SEQUENCE: 8
atggcgagcg actccccggc tcgaagcctg gatgaaatag atctctcggc tctgagggac 60
cctgcaggga tctttgaatt ggtggaactt gttggaaatg gaacatacgg gcaagtttat 120
aagggtcgtc atgtcaaaac gggccagctt gcagccatca aggttatgga tgtcacaggg 180
gatgaagagg aagaaatcaa acaagaaatt aacatgttga agaaatattc tcatcaccgg 240
aatattgcta catactatgg tgcttttatc aaaaagaacc caccaggcat ggatgaccaa 300
ctttggttgg tgatggagtt ttgtggtgct ggctctgtca ccgacctgat caagaacaca 360
aaaggtaaca cgttgaaaga ggagtggatt gcatacatct gcagggaaat cttacggggg 420
ctgagtcacc tgcaccagca taaagtgatt catcgagata ttaaagggca aaatgtcttg 480
ctgactgaaa atgcagaagt taaactagtg gactttggag tcagtgctca gcttgatcga 540
acagtgggca ggaggaatac tttcattgga actccctact ggatggcacc agaagttatt 600
gcctgtgatg aaaacccaga tgccacatat gatttcaaga gtgacttgtg gtctttgggt 660
atcaccgcca ttgaaatggc agaaggtgct ccccctctct gtgacatgca ccccatgaga 720
gctctcttcc tcatccccccg gaatccagcg cctcggctga agtctaagaa gtggtcaaaa 780
aaattccagt catttattga gagctgcttg gtaaagaatc acagccagcg accagcaaca 840

-continued

```
gaacaattga tgaagcatcc atttatacga gaccaaccta atgagcgaca ggtccgcatt    900
caactcaagg accatattga tagaacaaag aagaagcgag gagaaaaaga tgagacagag    960
tatgagtaca gtggaagtga ggaagaagag gaggagaatg actcaggaga gcccagctcc   1020
atcctgaatc tgccagggga gtcgacgctg cggagggact ttctgaggct gcagctggcc   1080
aacaaggagc gttctgaggc cctacggagg cagcagctgg agcagcagca gcgggagaat   1140
gaggagcaca agcggcagct gctggccgag cgtcagaagc gcatcgagga gcagaaagag   1200
cagaggcggc ggctggagga gcaacaaagg cgagagaagg agctgcggaa gcagcaggag   1260
agggagcagc gccggcacta tgaggagcag atgcgccggg aggaggagag gaggcgtgcg   1320
gagcatgaac aggaatataa gcgcaaacaa ttggaagaac agagacaagc agaaagactg   1380
cagaggcagc taaagcaaga aagagactac ttagtttccc ttcagcatca gcggcaggag   1440
cagaggcctg tggagaagaa gccactgtac cattacaaag aaggaatgag tcctagtgag   1500
aagccagcat gggccaagga gatcccacat ctggtagctg taaaatccca gggacctgcc   1560
ttgaccgcct cccagtcagt gcacgagcag cccacaaagg gcctctctgg gtttcaggag   1620
gctctgaacg tgacctccca ccgcgtggag atgccacgcc agaactcaga tcccacctcg   1680
gaaaatcctc ctctccccac tcgcattgaa aagtttgacc gaagctcttg gttacgacag   1740
gaagaagaca ttccaccaaa ggtgcctcaa agaacaactt ctatatcccc agcattagcc   1800
agaaagaatt ctcctgggaa tggtagtgct ctgggaccca gactaggatc tcaacccatc   1860
agagcaagca accctgatct ccggagaact gagcccatct tggagagccc cttgcagagg   1920
accagcagtg gcagttcctc cagctccagc accccctagct cccagcccag ctcccaagga   1980
ggctcccagc ctggatcaca agcaggatcc agtgaacgca ccagagttcg agccaacagt   2040
aagtcagaag gatcacctgt gcttccccat gagcctgcca aggtgaaacc agaagaatcc   2100
agggacatta cccggcccag tcgaccagct gatctgacgg cattagccaa agaactaaga   2160
gaactccgga ttgaagaaac aaaccgccca atgaagaagg tgactgatta ctcctcctcc   2220
agtgaggagt cagaaagtag cgaggaagag gaggaagatg gagagagcga gacccatgat   2280
gggacagtgg ctgtcagcga catacccaga ctgataccaa caggagctcc aggcagcaac   2340
gagcagtaca atgtgggaat ggtggggacg catgggctgg agacctctca tgcggacagt   2400
ttcagcggca gtatttcaag agaaggaacc ttgatgatta gagagacgtc tggagagaag   2460
aagcgatctg gccacagtga cagcaatggc tttgctggcc acatcaacct ccctgacctg   2520
gtgcagcaga gccattctcc agctggaacc ccgactgagg gactggggcg cgtctcaacc   2580
cattcccagg agatggactc tgggactgaa tatggcatgg ggagcagcac caaagcctcc   2640
ttcacccccct ttgtggaccc cagagtatac cagacgtctc ccactgatga agatgaagag   2700
gatgaggaat catcagccgc agctctgttt actagcgaac ttcttaggca agaacaggcc   2760
aaactcaatg aagcaagaaa gatttcggtg gtaaatgtaa acccaaccaa cattcggcct   2820
catagcgaca caccagaaat cagaaaatac aagaaacgat tcaactcaga aatactttgt   2880
gcagctctgt ggggtgtaaa ccttctggtg gggactgaaa atggcctgat gcttttggac   2940
cgaagtgggc aaggcaaagt ctataatctg atcaaccgga ggcgatttca gcagatggat   3000
gtgctagagg gactgaatgt ccttgtgaca atttcaggaa agaagaataa gctacgagtt   3060
tactatcttt catggttaag aaacagaata ctacataatg acccagaagt agaaaagaaa   3120
caaggctgga tcactgttgg ggacttggaa ggctgtatac attataaagt tgttaaatat   3180
gaaaggatca aatttttggt gattgcctta aagaatgctg tggaaatata tgcttgggct   3240
```

-continued

```
cctaaaccgt atcataaatt catggcattt aagtcttttg cagatctcca gcacaagcct   3300

ctgctagttg atctcacggt agaagaaggt caaagattaa aggttatttt tggttcacac   3360

actggtttcc atgtaattga tgttgattca ggaaactctt atgatatcta cataccatct   3420

catattcagg gcaatatcac tcctcatgct attgtcatct tgcctaaaac agatggaatg   3480

gaaatgcttg tttgctatga ggatgagggg gtgtatgtaa acacctatgg ccggataact   3540

aaggatgtgg tgctccaatg ggagaaatg cccacgtctg tggcctacat tcattccaat   3600

cagataatgg gctggggcga gaaagctatt gagatccggt cagtggaaac aggacatttg   3660

gatggagtat ttatgcataa gcgagctcaa aggttaaagt ttctatgtga aagaaatgat   3720

aaggtatttt ttgcatccgt gcgatctgga ggaagtagcc aagtgttttt catgaccctc   3780

aacagaaatt ccatgatgaa ctggtaa                                      3807
```

<210> SEQ ID NO 9
<211> LENGTH: 2178
<212> TYPE: DNA
<213> ORGANISM: Homo sapiens

<400> SEQUENCE: 9

```
ggcacgaggg agagagcgag acccatgatg ggacagtggc tgtcagcgac atacccagac     60

tgataccaac aggagctcca ggcagcaacg agcagtacaa tgtgggaatg gtggggacgc    120

atgggctgga gacctctcat gcggacagtt tcagcggcag tatttcaaga gaaggaacct    180

tgatgattag agagacgtct ggagagaaga agcgatctgg ccacagtgac agcaatggct    240

ttgctggcca catcaacctc cctgacctgg tgcagcagag ccattctcca gctggaaccc    300

cgactgaggg actggggcgc gtctcaaccc attcccagga gatggactct gggactgaat    360

atggcatggg gagcagcacc aaagcctcct tcaccccctt tgtggacccc agagtatacc    420

agacgtctcc cactgatgaa gatgaagagg atgaggaatc atcagccgca gctctgttta    480

ctagcgaact tcttaggcaa gaacaggcca aactcaatga agcaagaaag atttcggtgg    540

taaatgtaaa cccaaccaac attcggcctc atagcgacac accagaaatc agaaaataca    600

agaaacgatt caactcagaa atactttgtg cagctctgtg ggtgtaaac cttctggtgg    660

ggactgaaaa tggcctgatg cttttggacc gaagtgggca aggcaaagtc tataatctga    720

tcaaccggag gcgatttcag cagatggatg tgctagaggg actgaatgtc cttgtgacaa    780

tttcaggaaa gaagaataag ctacgagttt actatctttc atggttaaga aacagaatac    840

tacataatga cccagaagta gaaaagaaac aaggctggat cactgttggg gacttggaag    900

gctgtataca ttataaagtt gttaaatatg aaaggatcaa atttttggtg attgccttaa    960

agaatgctgt ggaaatatat gcttgggctc ctaaaccgta tcataaattc atggcattta   1020

agtcttttgc agatctccag cacaagcctc tgctagttga tctcacggta gaagaaggtc   1080

aaagattaaa ggttattttt ggttcacaca ctggtttcca tgtaattgat gttgattcag   1140

gaaactctta tgatatctac ataccatctc atattcaggg caatatcact cctcatgcta   1200

ttgtcatctt gcctaaaaca gatggaatgg aaatgcttgt ttgctatgag gatgaggggg   1260

tgtatgtaaa cacctatggc cggataacta aggatgtggt gctccaatgg ggagaaatgc   1320

ccacgtctgt ggcctacatt cattccaatc agataatggg ctggggcgag aaagctattg   1380

agatccggtc agtggaaaca ggacatttgg atggagtatt tatgcataag cgagctcaaa   1440

ggttaaagtt tctatgtgaa agaaatgata aggtattttt tgcatccgtg cgatctggag   1500

gaagtagcca agtgtttttc atgaccctca acagaaattc catgatgaac tggtaacaga   1560
```

```
agagcacttg gcacttatct tcatggcgtt atttctaatt taaaagaaca taactcatgt   1620

ggacttatgc cagtctagag gcagaatcag aaggcttggt tgaacatatc gctttccctt   1680

tttcctctcc ctccgcccct cccagtacag tccatctttc aatgttgcag cctggttgag   1740

aaggagagaa aaaggtggca ggaatttcca ggagatcccc aagaatgctg ccttgtctgt   1800

ggacaaagat ggaccatgtg cccttcggaa ttagggatag aaacaaatat tgtgtgctct   1860

taacgattaa gctgtgttat ggtgggtttt caggttttta ccttttttct ttacccccttt   1920

actctgcaag aatggggaaa gaatgcatac tgcgaaaatg agtcttttaa attctgtctg   1980

cctactagtt ttaagtatat ggtatgttgt aaaatttcca atgatgagag acagcacaat   2040

aaatgtacct tatctcctta ggctgaaggc cataactaca tagtggagta atttaagaac   2100

tctcttgcct tcaccaaccc aaaaggttgc tttttgatag caactggcta atgaattttt   2160

aaaaaaaaaa aaaaaaaa                                                  2178
```

<210> SEQ ID NO 10
<211> LENGTH: 3996
<212> TYPE: DNA
<213> ORGANISM: Homo sapiens

<400> SEQUENCE: 10

```
atggcgagcg actccccggc tcgaagcctg gatgaaatag atctctcggc tctgagggac     60

cctgcaggga tctttgaatt ggtggaactt gttggaaatg gaacatacgg gcaagtttat    120

aagggtcgtc atgtcaaaac gggccagctt gcagccatca aggttatgga tgtcacaggg    180

gatgaagagg aagaaatcaa acaagaaatt aacatgttga agaaatattc tcatcaccgg    240

aatattgcta catactatgg tgcttttatc aaaaagaacc caccaggcat ggatgaccaa    300

ctttggttgg tgatggagtt ttgtggtgct ggctctgtca ccgacctgat caagaacaca    360

aaaggtaaca cgttgaaaga ggagtggatt gcatacatct gcagggaaat cttacggggg    420

ctgagtcacc tgcaccagca taaagtgatt catcgagata ttaaagggca aaatgtcttg    480

ctgactgaaa atgcagaagt taaactagtg gactttggag tcagtgctca gcttgatcga    540

acagtgggca ggaggaatac tttcattgga actccctact ggatggcacc agaagttatt    600

gcctgtgatg aaaacccaga tgccacatat gatttcaaga gtgacttgtg gtctttgggt    660

atcaccgcca ttgaaatggc agaaggtgct ccccctctct gtgacatgca ccccatgaga    720

gctctcttcc tcatcccccg gaatccagcg cctcggctga agtctaagaa gtggtcaaaa    780

aaattccagt catttattga gagctgcttg gtaaagaatc acagccagcg accagcaaca    840

gaacaattga tgaagcatcc atttatacga gaccaaccta atgagcgaca ggtccgcatt    900

caactcaagg accatattga tagaacaaag aagaagcgag gagaaaaaga tgagacagag    960

tatgagtaca gtggaagtga ggaagaagag gaggagaatg actcaggaga gcccagctcc   1020

atcctgaatc tgccaggggga gtcgacgctg cggagggact ttctgaggct gcagctggcc   1080

aacaaggagc gttctgaggc cctacggagg cagcagctgg agcagcagca gcgggagaat   1140

gaggagcaca agcggcagct gctggccgag cgtcagaagc gcatcgagga gcagaaagag   1200

cagaggcggc ggctggagga gcaacaaagg cgagagaagg agctgcggaa gcagcaggag   1260

agggagcagc gccggcacta tgaggagcag atgcgccggg aggaggagag gaggcgtgcg   1320

gagcatgaac aggaatataa gcgcaaacaa ttggaagaac agagacaagc agaaagactg   1380

cagaggcagc taaagcaaga aagagactac ttagtttccc ttcagcatca gcggcaggag   1440

cagaggcctg tggagaagaa gccactgtac cattacaaag aaggaatgag tcctagtgag   1500
```

-continued

```
aagccagcat gggccaagga ggtagaagaa cggtcaaggc tcaaccggca aagttcccct   1560
gccatgcctc acaaggttgc caacaggata tctgacccca acctgccccc aaggtcggag   1620
tccttcagca ttagtggagt tcagcctgct cgaacacccc ccatgctcag accagtcgat   1680
ccccagatcc cacatctggt agctgtaaaa tcccagggac ctgccttgac cgcctcccag   1740
tcagtgcacg agcagcccac aaagggcctc tctgggtttc aggaggctct gaacgtgacc   1800
tcccaccgcg tggagatgcc acgccagaac tcagatccca cctcggaaaa tcctcctctc   1860
cccactcgca ttgaaaagtt tgaccgaagc tcttggttac gacaggaaga agacattcca   1920
ccaaaggtgc ctcaaagaac aacttctata tccccagcat tagccagaaa gaattctcct   1980
gggaatggta gtgctctggg acccagacta ggatctcaac ccatcagagc aagcaaccct   2040
gatctccgga gaactgagcc catcttggag agccccttgc agaggaccag cagtggcagt   2100
tcctccagct ccagcacccc tagctcccag cccagctccc aaggaggctc ccagcctgga   2160
tcacaagcag gatccagtga acgcaccaga gttcgagcca acagtaagtc agaaggatca   2220
cctgtgcttc cccatgagcc tgccaaggtg aaaccagaag aatccaggga cattacccgg   2280
cccagtcgac cagctagcta caaaaaagct atagatgagg atctgacggc attagccaaa   2340
gaactaagag aactccggat tgaagaaaca aaccgcccaa tgaagaaggt gactgattac   2400
tcctcctcca gtgaggagtc agaaagtagc gaggaagagg aggaagatgg agagagcgag   2460
acccatgatg ggacagtggc tgtcagcgac atacccagac tgataccaac aggagctcca   2520
ggcagcaacg agcagtacaa tgtgggaatg gtggggacgc atgggctgga gacctctcat   2580
gcggacagtt tcagcggcag tatttcaaga gaaggaacct tgatgattag agagacgtct   2640
ggagagaaga agcgatctgg ccacagtgac agcaatggct ttgctggcca catcaacctc   2700
cctgacctgg tgcagcagag ccattctcca gctggaaccc cgactgaggg actggggcgc   2760
gtctcaaccc attcccagga gatggactct gggactgaat atggcatggg gagcagcacc   2820
aaagcctcct tcacccccttt tgtggacccc agagtatacc agacgtctcc cactgatgaa   2880
gatgaagagg atgaggaatc atcagccgca gctctgttta ctagcgaact tcttaggcaa   2940
gaacaggcca aactcaatga agcaagaaag atttcggtgg taaatgtaaa cccaaccaac   3000
attcggcctc atagcgacac accagaaatc agaaaataca agaaacgatt caactcagaa   3060
atactttgtg cagctctgtg ggtgtaaac cttctggtgg ggactgaaaa tggcctgatg   3120
cttttggacc gaagtgggca aggcaaagtc tataatctga tcaaccggag gcgatttcag   3180
cagatggatg tgctagaggg actgaatgtc cttgtgacaa tttcaggaaa gaagaataag   3240
ctacgagttt actatctttc atggttaaga aacagaatac tacataatga cccagaagta   3300
gaaaagaaac aaggctggat cactgttggg gacttggaag gctgtataca ttataaagtt   3360
gttaaatatg aaaggatcaa atttttggtg attgccttaa agaatgctgt ggaaatatat   3420
gcttgggctc ctaaaccgta tcataaattc atggcattta agtcttttgc agatctccag   3480
cacaagcctc tgctagttga tctcacggta gaagaaggtc aaagattaaa ggttattttt   3540
ggttcacaca ctggtttcca tgtaattgat gttgattcag gaaactctta tgatatctac   3600
ataccatctc atattcaggg caatatcact cctcatgcta ttgtcatctt gcctaaaaca   3660
gatggaatgg aaatgcttgt ttgctatgag gatgaggggg tgtatgtaaa cacctatggc   3720
cggataacta aggatgtggt gctccaatgg ggagaaatgc ccacgtctgt ggcctacatt   3780
cattccaatc agataatggg ctggggcgag aaagctattg agatccggtc agtggaaaca   3840
ggacatttgg atggagtatt tatgcataag cgagctcaaa ggttaaagtt tctatgtgaa   3900
```

-continued agaaatgata aggtattttt tgcatccgtg cgatctggag gaagtagcca agtgtttttc 3960
atgaccctca acagaaattc catgatgaac tggtaa 3996

<210> SEQ ID NO 11
<211> LENGTH: 2490
<212> TYPE: DNA
<213> ORGANISM: Homo sapiens

<400> SEQUENCE: 11
agtacagcag caatcataag aggggaaaag ccatcactgt ggcttgggca ggagtcccag 60
aatactgggg cacaatttct aatcccacat attttcccat taactctggg ggtgaccagc 120
ttcacctttc caaaacaaaa tgagaaccca atgtttgtat atatgtgtac atacacatat 180
gtacacatat atattcagga ctgaacagtc tcagtctagc tattggtttt gaaaaagttt 240
aaattgattt catctttctt ttctagcttc tacacgctac aaacatcatt ttcttagttc 300
catgcagtaa ctatgtttgt cacagttcta tatagagctt ttttttttct tgttgcttaa 360
gctggagcac tgacttgctg agagatgtag ctttggtcgt atctaccact catatgctga 420
acaaattttt ctttcatagg atctgacggc attagccaaa gaactaagag aactccggat 480
tgaagaaaca aaccgcccaa tgaagaaggt gactgattac tcctcctcca gtgaggagtc 540
agaaagtagc gaggaagagg aggaagatgg agagagcgag acccatgatg ggacagtggc 600
tgtcagcgac atacccagac tgataccaac aggagctcca ggcagcaacg agcagtacaa 660
tgtgggaatg gtggggacgc atgggctgga gacctctcat gcggacagtt tcagtggcag 720
tatttcaaga gaaggaacct tgatgattag agagacgtct ggagagaaga agcgatctgg 780
ccacagtgac agcaatggct ttgctggcca catcaacctc cctgacctgg tgcagcagag 840
ccattctcca gctggaaccc cgactgaggg actggggcgc gtctcaaccc attcccagga 900
gatggactct gggactgaat atggcatggg gagcagcacc aaagcctcct tcacccccct 960
tgtggacccc agagtatacc agacgtctcc cactgatgaa gatgaagagg atgaggaatc 1020
atcagccaca gctctgttta ctagcgaact tcttaggcaa gaacaggcca aactcaatga 1080
agcaagaaag atttcggtgg taaatgtaaa cccaaccaac attcggcctc atagcgacac 1140
accagaaatc agaaaataca agaaacgatt caactcagaa atactttgtg cagctctgtg 1200
gggtgtaaac cttctggtgg ggactgaaaa tggcctgatg cttttggacc gaagtgggca 1260
aggcaaagtc tataatctga tcaaccggag gcgatttcag cagatggatg tgctagaggg 1320
actgaatgtc cttgtgacaa tttcaggaaa gaagaataag ctacgagttt actatctttc 1380
atggttaaga aacagaatac tacataatga cccagaagta gaaaagaaac aaggctggat 1440
cactgttggg gacttggaag gctgtataca ttataaagtt gttaaatatg aaaggatcaa 1500
atttttggtg attgccttaa agaatgctgt ggaaatatat gcttgggctc ctaaaccgta 1560
tcataaattc atggcattta agtcttttgc agatctccag cacaagcctc tgctagttga 1620
tctcacggta gaagaaggtc aaagattaaa ggttattttt ggttcacaca ctggtttcca 1680
tgtaattgat gttgattcag gaaactctta tgatatctac ataccatctc atattcaggg 1740
caatatcact cctcatgcta ttgtcatctt gcctaaaaca gatggaatgg aaatgcttgt 1800
ttgctatgag gatgaggggg tgtatgtaaa cacctatggc cggataacta aggatgtggt 1860
gctccaatgg ggagaaatgc ccacgtctgt ggcctacatt cattccaatc agataatggg 1920
ctggggcgag aaagctattg agatccggtc agtggaaaca ggacatttgg atggagtatt 1980
tatgcataag cgagctcaaa ggttaaagtt tctatgtgaa agaaatgata aggtattttt 2040
tgcatccgtg cgatctggag gaagtagcca agtgtttttc atgaccctca acagaaattc 2100
catgatgaac tggtaacaga agagcacttg gcacttatct tcatggcgtt atttctaatt 2160
taaaagaaca taactcatgt ggacttatgc cagtctagag gcagaatcag aaggcttggt 2220
tgaacatatc gctttccctt tttcctctcc ctccgcccct cccagtacag tccatctttc 2280
aatgttgcag cctggttgag aaggagagaa aaaggtggca ggaatttcca ggagatcccc 2340
aagaatgctg ccttgtctgt ggacaaagat ggaccatgtg cccttcggaa ttagggatag 2400
aaacaaatat tgtgtgctct taacgattaa aaaaaaaaaa aaaaaaaaaa aaaaaaaaaa 2460
aaaaaaaaaa aaggaaaaaa aaaaaaaaaa 2490

<210> SEQ ID NO 12
<211> LENGTH: 3817
<212> TYPE: DNA
<213> ORGANISM: Homo sapiens

<400> SEQUENCE: 12
cacagagcga cagagacatt tattgttatt tgtttttgg tggcaaaaag ggaaaatggc 60
gaacgactcc cctgcaaaaa gtctggtgga catcgacctc tcctccctgc gggatcctgc 120
tgggattttt gagctggtgg aagtggttgg aaatggcacc tatggacaag tctataaggg 180
tcgacatgtt aaaacgggtc agttggcagc catcaaagtt atggatgtca ctgaggatga 240
agaggaagaa atcaaactgg agataaatat gctaaagaaa tactctcatc acagaaacat 300
tgcaacatat tatggtgctt tcatcaaaaa gagccctcca ggacatgatg accaactctg 360
gcttgttatg gagttctgtg ggctgggtc cattacagac cttgtgaaga acaccaaagg 420
gaacacactc aaagaagact ggatcgctta catctccaga gaaatcctga ggggactggc 480
acatcttcac attcatcatg tgattcaccg ggatatcaag ggccagaatg tgttgctgac 540
tgagaatgca gaggtgaaac ttgttgactt tggtgtgagt gctcagctgg acaggactgt 600
ggggcggaga aatacgttca taggcactcc ctactggatg gctcctgagg tcatcgcctg 660
tgatgagaac ccagatgcca cctatgatta cagaagtgat ctttggtctt gtggcattac 720
agccattgag atggcagaag gtgctccccc tctctgtgac atgcatccaa tgagagcact 780
gtttctcatt cccagaaacc ctcctccccg gctgaagtca aaaaaatggt cgaagaagtt 840
ttttagtttt atagaagggt gcctggtgaa gaattacatg cagcggccct ctacagagca 900
gcttttgaaa catcctttta taagggatca gccaaatgaa aggcaagtta gaatccagct 960
taaggatcat atagatcgta ccaggaagaa gagaggcgag aaagatgaaa ctgagtatga 1020
gtacagtggg agtgaggaag aagaggagga agtgcctgaa caggaaggag agccaagttc 1080
cattgtgaac gtgcctggtg agtctactct tcgccgagat ttcctgagac tgcagcagga 1140
gaacaaggaa cgttccgagg ctcttcggag acaacagtta ctacaggagc aacagctccg 1200
ggagcaggaa gaatataaaa ggcaactgct ggcagagaga cagaagcgga ttgagcagca 1260
gaaagaacag aggcgacggc tagaagagca acaaaggaga gagcgggaag ctagaaggca 1320
gcaggaacgt gaacagcgaa ggagagaaca agaagaaaag aggcgtctag aggagttgga 1380
gagaaggcgc aaagaagaag aggagaggag acgggcagaa gaagaaaaga ggagagttga 1440
aagagaacag gagtatatca ggcgacagct agaagaggag cagcggcact tggaagtcct 1500
tcagcagcag ctgctccagg agcaggccat gttactgcat gaccatagga ggccgcaccc 1560
gcagcactcg cagcagccgc caccaccgca gcaggaaagg agcaagccaa gcttccatgc 1620
tcccgagccc aaagcccact acgagcctgc tgaccgagcg cgagaggttc ctgtgagaac 1680

```
aacatctcgc tcccctgttc tgtcccgtcg agattcccca ctgcagggca gtgggcagca   1740
gaatagccag gcaggacaga gaaactccac cagcagtatt gagcccaggc ttctgtggga   1800
gagagtggag aagctggtgc ccagacctgg cagtggcagc tcctcagggt ccagcaactc   1860
aggatcccag cccgggtctc accctgggtc tcagagtggc tccggggaac gcttcagagt   1920
gagatcatca tccaagtctg aaggctctcc atctcagcgc ctggaaaatg cagtgaaaaa   1980
acctgaagat aaaaaggaag ttttcagacc cctcaagcct gctggcgaag tggatctgac   2040
cgcactggcc aaagagcttc gagcagtgga agatgtacgg ccacctcaca aagtaacgga   2100
ctactcctca tccagtgagg agtcggggac gacggatgag gaggacgacg atgtggagca   2160
ggaaggggct gacgagtcca cctcaggacc agaggacacc agagcagcgt catctctgaa   2220
tttgagcaat ggtgaaacgg aatctgtgaa aaccatgatt gtccatgatg atgtagaaag   2280
tgagccggcc atgaccccat ccaaggaggg cactctaatc gtccgccaga ctcagtccgc   2340
tagtagcaca ctccagaaac acaaatcttc ctcctccttt acacctttta tagaccccag   2400
attactacag atttctccat ctagcggaac aacagtgaca tctgtggtgg gattttcctg   2460
tgatgggatg agaccagaag ccataaggca agatcctacc cggaaaggct cagtggtcaa   2520
tgtgaatcct accaacacta ggccacagag tgacaccccg gagattcgta aatacaagaa   2580
gaggtttaac tctgagattc tgtgtgctgc cttatgggga gtgaatttgc tagtgggtac   2640
agagagtggc ctgatgctgc tggacagaag tggccaaggg aaggtctatc ctcttatcaa   2700
ccgaagacga tttcaacaaa tggacgtact tgagggcttg aatgtcttgg tgacaatatc   2760
tggcaaaaag gataagttac gtgtctacta tttgtcctgg ttaagaaata aaatacttca   2820
caatgatcca gaagttgaga agaagcaggg atggacaacc gtaggggatt tggaaggatg   2880
tgtacattat aaagttgtaa aatatgaaag aatcaaattt ctggtgattg ctttgaagag   2940
ttctgtggaa gtctatgcgt gggcaccaaa gccatatcac aaatttatgg cctttaagtc   3000
atttggagaa ttggtacata agccattact ggtggatctc actgttgagg aaggccagag   3060
gttgaaagtg atctatggat cctgtgctgg attccatgct gttgatgtgg attcaggatc   3120
agtctatgac atttatctac caacacatgt aagaaagaac ccacactcta tgatccagtg   3180
tagcatcaaa ccccatgcaa tcatcatcct ccccaataca gatggaatgg agcttctggt   3240
gtgctatgaa gatgaggggg tttatgtaaa cacatatgga aggatcacca aggatgtagt   3300
tctacagtgg ggagagatgc ctacatcagt agcatatatt cgatccaatc agacaatggg   3360
ctggggagag aaggccatag agatccgatc tgtggaaact ggtcacttgg atggtgtgtt   3420
catgcacaaa agggctcaaa gactaaaatt cttgtgtgaa cgcaatgaca aggtgttctt   3480
tgcctctgtt cggtctggtg gcagcagtca ggtttatttc atgaccttag gcaggacttc   3540
tcttctgagc tggtagaagc agtgtgatcc agggattact ggcctccaga gtcttcaaga   3600
tcctgagaac ttggaattcc ttgtaactgg agctcggagc tgcaccgagg gcaaccagga   3660
cagctgtgtg tgcagacctc atgtgttggg ttctctcccc tccttcctgt tcctcttata   3720
taccagttta tccccattct ttttttttt cttactccaa aataaatcaa ggctgcaatg   3780
cagctggtgc tgttcagatt ctaaaaaaaa aaaaaaa                            3817
```

<210> SEQ ID NO 13
<211> LENGTH: 3864
<212> TYPE: DNA
<213> ORGANISM: Homo sapiens

<400> SEQUENCE: 13

-continued

```
aattcgagga tccgggtacc atggcacaga gcgacagaga catttattgt tatttgtttt      60
ttggtggcaa aaagggaaaa tggcgaacga ctcccctgca aaaagtctgg tggacatcga     120
cctctcctcc ctgcgggatc ctgctgggat ttttgagctg gtggaagtgg ttggaaatgg     180
cacctatgga caagtctata agggtcgaca tgttaaaacg ggtcagttgg cagccatcaa     240
agttatggat gtcactgagg atgaagagga agaaatcaaa ctggagataa atatgctaaa     300
gaaatactct catcacagaa acattgcaac atattatggt gctttcatca aaaagagccc     360
tccaggacat gatgaccaac tctggcttgt tatggagttc tgtggggctg ggtccattac     420
agaccttgtg aagaacacca aagggaacac actcaaagaa gactggatcg cttacatctc     480
cagagaaatc ctgaggggac tggcacatct tcacattcat catgtgattc accgggatat     540
caagggccag aatgtgttgc tgactgagaa tgcagaggtg aaacttgttg actttggtgt     600
gagtgctcag ctggacagga ctgtggggcg gagaaatacg ttcataggca ctccctactg     660
gatggctcct gaggtcatcg cctgtgatga gaacccagat gccacctatg attacagaag     720
tgatctttgg tcttgtggca ttacagccat tgagatggca gaaggtgctc cccctctctg     780
tgacatgcat ccaatgagag cactgtttct cattcccaga aaccctcctc cccggctgaa     840
gtcaaaaaaa tggtcgaaga agttttttag ttttatagaa gggtgcctgg tgaagaatta     900
catgcagcgg ccctctacag agcagctttt gaaacatcct tttataaggg atcagccaaa     960
tgaaaggcaa gttagaatcc agcttaagga tcatatagat cgtaccagga agaagagagg    1020
cgagaaagat gaaactgagt atgagtacag tgggagtgag gaagaagagg aggaagtgcc    1080
tgaacaggaa ggagagccaa gttccattgt gaacgtgcct ggtgagtcta ctcttcgccg    1140
agatttcctg agactgcagc aggagaacaa ggaacgttcc gaggctcttc ggagacaaca    1200
gttactacag gagcaacagc tccgggagca ggaagaatat aaaaggcaac tgctggcaga    1260
gagacagaag cggattgagc agcagaaaga acagaggcga cggctagaag agcaacaaag    1320
gagagagcgg gaggctagaa ggcagcagga acgtgaacag cgaaggagag aacaagaaga    1380
aaagaggcgt ctagaggagt tggagagaag gcgcaaagaa gaagaggaga ggagacgggc    1440
agaagaagaa aagaggagag ttgaaagaga acaggagtat atcaggcgac agctagaaga    1500
ggagcagcgg cacttggaag tccttcagca gcagctgctc caggagcagg ccatgttact    1560
gcatgaccat aggaggccgc acccgcagca ctcgcagcag ccgccaccac cgcagcagga    1620
aaggagcaag ccaagcttcc atgctcccga gcccaaagcc cactacgagc ctgctgaccg    1680
agcgcgagag gttcctgtga gaacaacatc tcgctcccct gttctgtccc gtcgagattc    1740
cccactgcag ggcagtgggc agcagaatag ccaggcagga cagagaaact ccaccagtat    1800
tgagcccagg cttctgtggg agagagtgga gaagctggtg cccagacctg gcagtggcag    1860
ctcctcaggg tccagcaact caggatccca gcccgggtct caccctgggt ctcagagtgg    1920
ctccggggaa cgcttcagag tgagatcatc atccaagtct gaaggctctc catctcagcg    1980
cctggaaaat gcagtgaaaa aacctgaaga taaaaaggaa gttttcagac ccctcaagcc    2040
tgctggcgaa gtggatctga ccgcactggc caaagagctt cgagcagtgg aagatgtacg    2100
gccacctcac aaagtaacgg actactcctc atccagtgag gagtcgggga cgacggatga    2160
ggaggacgac gatgtggagc aggaaggggc tgacgagtcc acctcaggac cagaggacac    2220
cagagcagcg tcatctctga atttgagcaa tggtgaaacg gaatctgtga aaaccatgat    2280
tgtccatgat gatgtagaaa gtgagccggc catgacccca tccaaggagg gcactctaat    2340
cgtccgccag actcagtccg ctagtagcac actccagaaa cacaaatctt cctcctcctt    2400
```

-continued

```
tacacctttt atagacccca gattactaca gatttctcca tctagcggaa caacagtgac   2460

atctgtggtg ggattttcct gtgatgggat gagaccagaa gccataaggc aagatcctac   2520

ccggaaaggc tcagtggtca atgtgaatcc taccaacact aggccacaga gtgacacccc   2580

ggagattcgt aaatacaaga agaggtttaa ctctgagatt ctgtgtgctg ccttatgggg   2640

agtgaatttg ctagtgggta cagagagtgg cctgatgctg ctggacagaa gtggccaagg   2700

gaaggtctat cctcttatca accgaagacg atttcaacaa atggacgtac ttgagggctt   2760

gaatgtcttg gtgacaatat ctggcaaaaa ggataagtta cgtgtctact atttgtcctg   2820

gttaagaaat aaaatacttc acaatgatcc agaagttgag aagaagcagg gatggacaac   2880

cgtaggggat ttggaaggat gtgtacatta taaagttgta aaatatgaaa gaatcaaatt   2940

tctggtgatt gctttgaaga gttctgtgga agtctatgcg tgggcaccaa agccatatca   3000

caaatttatg gcctttaagt catttggaga attggtacat aagccattac tggtggatct   3060

cactgttgag gaaggccaga ggttgaaagt gatctatgga tcctgtgctg gattccatgc   3120

tgttgatgtg gattcaggat cagtctatga catttatcta ccaacacatg taagaaagaa   3180

cccacactct atgatccagt gtagcatcaa accccatgca atcatcatcc tccccaatac   3240

agatggaatg gagcttctgg tgtgctatga agatgagggg gtttatgtaa acacatatgg   3300

aaggatcacc aaggatgtag ttctacagtg gggagagatg cctacatcag tagcatatat   3360

tcgatccaat cagacaatgg gctggggaga gaaggccata gagatccgat ctgtggaaac   3420

tggtcacttg gatggtgtgt tcatgcacaa aagggctcaa agactaaaat tcttgtgtga   3480

acgcaatgac aaggtgttct ttgcctctgt tcggtctggt ggcagcagtc aggtttattt   3540

catgacctta ggcaggactt ctcttctgag ctggtagaag cagtgtgatc cagggattac   3600

tggcctccag agtcttcaag atcctgagaa cttggaattc cttgtaactg gagctcggag   3660

ctgcaccgag ggcaaccagg acagctgtgt gtgcagacct catgtgttgg gttctctccc   3720

ctccttcctg ttcctcttat ataccagttt atccccattc tttttttttt tcttactcca   3780

aaataaatca aggctgcaat gcagctggtg ctgttcagat tccaaaaaaa aaaaaaaacc   3840

atggtacccg gatcctcgaa ttcc                                          3864
```

<210> SEQ ID NO 14
<211> LENGTH: 3608
<212> TYPE: DNA
<213> ORGANISM: Homo sapiens

<400> SEQUENCE: 14

```
agggaacaca ctcaaagaag actggatcgc ttacatctcc agagaaatcc tgaggggact     60

ggcacatctt cacattcatc atgtgattca ccgggatatc aagggccaga atgtgttgct    120

gactgagaat gcagaggtga aacttgttga ctttggtgtg agtgctcagc tggacaggac    180

tgtggggcgg agaaatacgt tcataggcac tccctactgg atggctcctg aggtcatcgc    240

ctgtgatgag aacccagatg ccacctatga ttacagaagt gatctttggt cttgtggcat    300

tacagccatt gagatggcag aaggtgctcc ccctctctgt gacatgcatc caatgagagc    360

actgtttctc attcccagaa accctcctcc ccggctgaag tcaaaaaaat ggtcgaagaa    420

gtttttttagt tttatagaag ggtgcctggt gaagaattac atgcagcggc cctctacaga    480

gcagcttttg aaacatcctt ttataaggga tcagccaaat gaaaggcaag ttagaatcca    540

gcttaaggat catatagatc gtaccaggaa gaagagaggc gagaaagatg aaactgagta    600

tgagtacagt gggagtgagg aagaagagga ggaagtgcct gaacaggaag gagagccaag    660
```

-continued

```
ttccattgtg aacgtgcctg gtgagtctac tcttcgccga gatttcctga gactgcagca    720
ggagaacaag gaacgttccg aggctcttcg gagacaacag ttactacagg agcaacagct    780
ccgggagcag gaagaatata aaaggcaact gctggcagag agacagaagc ggattgagca    840
gcagaaagaa cagaggcgac ggctagaaga gcaacaaagg agagagcggg aagctagaag    900
gcagcaggaa cgtgaacagc gaaggagaga acaagaagaa aagaggcgtc tagaggagtt    960
ggagagaagg cgcaaagaag aagaggagag gagacgggca gaagaagaaa agaggagagt   1020
tgaaagagaa caggagtata tcaggcgaca gctagaagag gagcagcggc acttggaagt   1080
ccttcagcag cagctgctcc aggagcaggc catgttactg gagtgccgat ggcgggagat   1140
ggaggagcac cggcaggcag agaggctcca gaggcagttg caacaagaac aagcatatct   1200
cctgtctcta cagcatgacc ataggaggcc gcacccgcag cactcgcagc agccgccacc   1260
accgcagcag gaaaggagca agccaagctt ccatgctccc gagcccaaag cccactacga   1320
gcctgctgac cgagcgcgag aggtggaaga tagatttagg aaaactaacc acagctcccc   1380
tgaagcccag tctaagcaga caggcagagt attggagcca ccagtgcctt cccgatcaga   1440
gtctttttcc aatggcaact ccgagtctgt gcatcccgcc ctgcagagac cagcggagcc   1500
acagggttcc tgtgagaaca acatctcgct cccctgttct gtcccgtcga gattccccac   1560
tgcagggcag tgggcagcag aatagccagg caggacagag aaactccacc agcagtattg   1620
agcccaggct tctgtgggag agagtggaga agctggtgcc cagacctggc agtggcagct   1680
cctcagggtc cagcaactca ggatcccagc ccgggtctca ccctgggtct cagagtggct   1740
ccggggaacg cttcagagtg agatcatcat ccaagtctga aggctctcca tctcagcgcc   1800
tggaaaatgc agtgaaaaaa cctgaagata aaaaggaagt tttcagaccc ctcaagcctg   1860
ctgatctgac cgcactggcc aaagagcttc gagcagtgga agatgtacgg ccacctcaca   1920
aagtaacgga ctactcctca tccagtgagg agtcggggac gacggatgag gaggacgacg   1980
atgtggagca ggaaggggct gacgagtcca cctcaggacc agaggacacc agagcagcgt   2040
catctctgaa tttgagcaat ggtgaaacgg aatctgtgaa aaccatgatt gtccatgatg   2100
atgtagaaag tgagccggcc atgaccccat ccaaggaggg cactctaatc gtccgccaga   2160
ctcagtccgc tagtagcaca ctccagaaac acaaatcttc ctcctccttt acacctttta   2220
tagaccccag attactacag atttctccat ctagcggaac aacagtgaca tctgtggtgg   2280
gattttcctg tgatgggatg agaccagaag ccataaggca agatcctacc cggaaaggct   2340
cagtggtcaa tgtgaatcct accaacacta ggccacagag tgacaccccg gagattcgta   2400
aatacaagaa gaggtttaac tctgagattc tgtgtgctgc cttatgggga gtgaatttgc   2460
tagtgggtac agagagtggc ctgatgctgc tggacagaag tggccaaggg aaggtctatc   2520
ctcttatcaa ccgaagacga tttcaacaaa tggacgtact tgagggcttg aatgtcttgg   2580
tgacaatatc tggcaaaaag gataagttac gtgtctacta tttgtcctgg ttaagaaata   2640
aaatacttca caatgatcca gaagttgaga agaagcaggg atggacaacc gtaggggatt   2700
tggaaggatg tgtacattat aaagttgtaa aatatgaaag aatcaaattt ctggtgattg   2760
ctttgaagag ttctgtggaa gtctatgcgt gggcaccaaa gccatatcac aaatttatgg   2820
cctttaagtc atttggagaa ttggtacata agccattact ggtggatctc actgttgagg   2880
aaggccagag gttgaaagtg atctatggat cctgtgctgg attccatgct gttgatgtgg   2940
attcaggatc agtctatgac atttatctac caacacatat ccagtgtagc atcaaacccc   3000
atgcaatcat catcctcccc aatacagatg gaatggagct tctggtgtgc tatgaagatg   3060
```

```
aggggggttta tgtaaacaca tatggaagga tcaccaagga tgtagttcta cagtggggag   3120
agatgcctac atcagtagca tatattcgat ccaatcagac aatgggctgg ggagagaagg   3180
ccatagagat ccgatctgtg gaaactggtc acttggatgg tgtgttcatg cacaaaaggg   3240
ctcaaagact aaaattcttg tgtgaacgca atgacaaggt gttctttgcc tctgttcggt   3300
ctggtggcag cagtcaggtt tatttcatga ccttaggcag gacttctctt ctgagctggt   3360
agaagcagtg tgatccaggg attactggcc tccagagtct tcaagatcct gagaacttgg   3420
aattccttgt aactggagct cggagctgca ccgagggcaa ccaggacagc tgtgtgtgca   3480
gacctcatgt gttgggttct ctcccctcct tcctgttcct cttatatacc agtttatccc   3540
cattcttttt tttttcttta ctccaaaata aatcaaggct gcaatgcagc tggtgctgtt   3600
cagattct                                                           3608
```

<210> SEQ ID NO 15
<211> LENGTH: 4266
<212> TYPE: DNA
<213> ORGANISM: Homo sapiens

<400> SEQUENCE: 15

```
caagtctata agggtcgaca tgttaaaacg ggtcagttgg cagccatcaa agttatggat     60
gtcactgagg atgaagagga agaaatcaaa ctggagataa atatgctaaa gaaatactct    120
catcacagaa acattgcaac atattatggt gctttcatca aaaagagccc tccaggacat    180
gatgaccaac tctggcttgt tatggagttc tgtggggctg ggtccattac agaccttgtg    240
aagaacacca aagggaacac actcaaagaa gactggatcg cttacatctc cagagaaatc    300
ctgaggggac tggcacatct tcacattcat catgtgattc accgggatat caagggccag    360
aatgtgttgc tgactgagaa tgcagaggtg aaacttgttg actttggtgt gagtgctcag    420
ctggacagga ctgtggggcg gagaaatacg ttcataggca ctccctactg gatggctcct    480
gaggtcatcg cctgtgatga gaacccagat gccacctatg attacagaag tgatctttgg    540
tcttgtggca ttacagccat tgagatggca gaaggtgctc cccctctctg tgacatgcat    600
ccaatgagag cactgtttct cattcccaga aaccctcctc cccggctgaa gtcaaaaaaa    660
tggtcgaaga agtttttttag ttttatagaa gggtgcctgg tgaagaatta catgcagcgg    720
ccctctacag agcagctttt gaaacatcct tttataaggg atcagccaaa tgaaaggcaa    780
gttagaatcc agcttaagga tcatatagat cgtaccagga agaagagagg cgagaaaagat    840
gaaactgagt atgagtacag tgggagtgag gaagaagagg aggaagtgcc tgaacaggaa    900
ggagagccaa gttccattgt gaacgtgcct ggtgagtcta ctcttcgccg agatttcctg    960
agactgcagc aggagaacaa ggaacgttcc gaggctcttc ggagacaaca gttactacag   1020
gagcaacagc tccgggagca ggaagaatat aaaaggcaac tgctggcaga gagacagaag   1080
cggattgagc agcagaaaga acagaggcga cggctagaag agcaacaaag gagagagcgg   1140
gaagctagaa ggcagcagga acgtgaacag cgaaggagag aacaagaaga aaagaggcgt   1200
ctagaggagt tggagagaag gcgcaaagaa gaagaggaga ggagacgggc agaagaagaa   1260
aagaggagag ttgaaagaga acaggagtat atcaggcgac agctagaaga ggagcagcgg   1320
cacttggaag tccttcagca gcagctgctc caggagcagg ccatgttact gcatgaccat   1380
aggaggccgc acccgcagca ctcgcagcag ccgccaccac cgcagcagga aaggagcaag   1440
ccaagcttcc atgctcccga gcccaaagcc cactacgagc ctgctgaccg agcgcgagag   1500
gtggaagata gatttaggaa aactaaccac agctcccctg aagcccagtc taagcagaca   1560
```

-continued

```
ggcagagtat tggagccacc agtgccttcc cgatcagagt ctttttccaa tggcaactcc   1620
gagtctgtgc atcccgccct gcagagacca gcggagccac aggttcctgt gagaacaaca   1680
tctcgctccc ctgttctgtc ccgtcgagat tccccactgc agggcagtgg gcagcagaat   1740
agccaggcag gacagagaaa ctccaccagc agtattgagc ccaggcttct gtgggagaga   1800
gtggagaagc tggtgcccag acctggcagt ggcagctcct cagggtccag caactcagga   1860
tcccagcccg ggtctcaccc tgggtctcag agtggctccg gggaacgctt cagagtgaga   1920
tcatcatcca agtctgaagg ctctccatct cagcgcctgg aaaatgcagt gaaaaaacct   1980
gaagataaaa aggaagtttt cagacccctc aagcctgctg gcgaagtgga tctgaccgca   2040
ctggccaaag agcttcgagc agtggaagat gtacggccac ctcacaaagt aacggactac   2100
tcctcatcca gtgaggagtc ggggacgacg gatgaggagg acgacgatgt ggagcaggaa   2160
ggggctgacg agtccacctc aggaccagag gacaccagag cagcgtcatc tctgaatttg   2220
agcaatggtg aaacggaatc tgtgaaaacc atgattgtcc atgatgatgt agaaagtgag   2280
ccggccatga ccccatccaa ggagggcact ctaatcgtcc gccagactca gtccgctagt   2340
agcacactcc agaaacacaa atcttcctcc tcctttacac cttttataga ccccagatta   2400
ctacagattt ctccatctag cggaacaaca gtgacatctg tggtgggatt ttcctgtgat   2460
gggatgagac cagaagccat aaggcaagat cctacccgga aaggctcagt ggtcaatgtg   2520
aatcctacca acactaggcc acagagtgac accccggaga ttcgtaaata caagaagagg   2580
tttaactctg agattctgtg tgctgcctta tggggagtga atttgctagt gggtacagag   2640
agtggcctga tgctgctgga cagaagtggc caagggaagg tctatcctct tatcaaccga   2700
agacgatttc aacaaatgga cgtacttgag ggcttgaatg tcttggtgac aatatctggc   2760
aaaaaggata agttacgtgt ctactatttg tcctggttaa gaaataaaat acttcacaat   2820
gatccagaag ttgagaagaa gcagggatgg acaaccgtag gggatttgga aggatgtgta   2880
cattataaag ttgtaaaata tgaaagaatc aaatttctgg tgattgcttt gaagagttct   2940
gtggaagtct atgcgtgggc accaaagcca tatcacaaat ttatggcctt taagtcattt   3000
ggagaattgg tacataagcc attactggtg gatctcactg ttgaggaagg ccagaggttg   3060
aaagtgatct atggatcctg tgctggattc catgctgttg atgtggattc aggatcagtc   3120
tatgacattt atctaccaac acatatccag tgtagcatca aaccccatgc aatcatcatc   3180
ctccccaata cagatggaat ggagcttctg gtgtgctatg aagatgaggg ggtttatgta   3240
aacacatatg gaaggatcac caaggatgta gttctacagt ggggagagat gcctacatca   3300
gtagcatata ttcgatccaa tcagacaatg ggctggggag agaaggccat agagatccga   3360
tctgtggaaa ctggtcactt ggatggtgtg ttcatgcaca aaagggctca aagactaaaa   3420
ttcttgtgtg aacgcaatga caaggtgttc tttgcctctg ttcggtctgg tggcagcagt   3480
caggtttatt tcatgacctt aggcaggact tctcttctga gctggtagaa gcagtgtgat   3540
ccagggatta ctggcctcca gagtcttcaa gatcctgaga acttggaatt ccttgtaact   3600
ggagctcgga gctgcaccga gggcaaccag gacagctgtg tgtgcagacc tcatgtgttg   3660
ggttctctcc cctccttcct gttcctctta tataccagtt tatccccatt cttttttttt   3720
ttcttactcc aaaataaatc aaggctgcaa tgcagctggt gctgttcaga ttctaccatc   3780
aggtgctata agtgtttggg attgagcatc atactggaaa gcaaacacct ttcctccagc   3840
tccagaattc cttgtctctg aatgactctg tcttgtgggt gtctgacagt ggcgacgatg   3900
aacatgccgt tggttttatt ggcagtgggc acaaggaggt gagaagtggt ggtaaaagga   3960
```

gcggagtgct gaagcagaga gcagatttaa tatagtaaca ttaacagtgt atttaattga 4020
catttctttt ttgtaatgtg acgatatgtg gacaaagaag aagatgcagg tttaagaagt 4080
taatatttat aaaatgtgaa agacacagtt actaggataa ctttttgtg ggtggggctt 4140 gggagatggg gtggggtggg ttaaggggtc ccattttgtt tctttggatt tggggtgggg 4200
gtcctggcca agaactcagt catttttctg tgtaccaggt tgcctaaatc atgtgcagat 4260
ggttct 4266

<210> SEQ ID NO 16
<211> LENGTH: 3448
<212> TYPE: DNA
<213> ORGANISM: Homo sapiens

<400> SEQUENCE: 16 gtttttagt tttatagaag ggtgcctggt gaagaattac atgcagcggc cctctacaga 60
gcagcttttg aaacatcctt ttataaggga tcagccaaat gaaaggcaag ttagaatcca 120
gcttaaggat catatagatc gtaccaggaa gaagagaggc gagaaagatg aaactgagta 180
tgagtacagt gggagtgagg aagaagagga ggaagtgcct gaacaggaag gagagccaag 240
ttccattgtg aacgtgcctg gtgagtctac tcttcgccga gatttcctga gactgcagca 300
ggagaacaag gaacgttccg aggctcttcg gagacaacag ttactacagg agcaacagct 360
ccgggagcag gaagaatata aaaggcaact gctggcagag agacagaagc ggattgagca 420
gcagaaagaa cagaggcgac ggctagaaga gcaacaaagg agagagcggg aagctagaag 480
gcagcaggaa cgtgaacagc gaaggagaga acaagaagaa aagaggcgtc tagaggagtt 540
ggagagaagg cgcaaagaag aagaggagag gagacgggca gaagaagaaa agaggagagt 600
tgaaagagaa caggagtata tcaggcgaca gctagaagag gagcagcggc acttggaagt 660
ccttcagcag cagctgctcc aggagcaggc catgttactg gagtgccgat ggcgggagat 720
ggaggagcac cggcaggcag agaggctcca gaggcagttg caacaagaac aagcatatct 780
cctgtctcta cagcatgacc ataggaggcc gcacccgcag cactcgcagc agccgccacc 840
accgcagcag gaaaggagca agccaagctt ccatgctccc gagcccaaag cccactacga 900
gcctgctgac cgagcgcgag aggtggaaga tagatttagg aaaactaacc acagctcccc 960
tgaagcccag tctaagcaga caggcagagt attggagcca ccagtgcctt cccgatcaga 1020
gtctttttcc aatggcaact ccgagtctgt gcatcccgcc ctgcagagac cagcggagcc 1080
acaggtacag tggtcccacc tggcatctct caagaacaat gtttcccctg tctcgcgatc 1140
ccattccttc agtgaccctt ctcccaaatt tgcacaccac catcttcgtt ctcaggaccc 1200
atgtccacct tcccgcagtg aggtgctcag tcagagctct gactctaagt cagaggcgcc 1260
tgaccctacc caaaaggctt ggtctagatc agacagtgac gaggtgcctc caagggttcc 1320
tgtgagaaca acatctcgct cccctgttct gtcccgtcga gattccccac tgcagggcag 1380
tgggcagcag aatagccagg caggacagag aaactccacc agcagtattg agcccaggct 1440
tctgtgggag agagtggaga agctggtgcc cagacctggc agtggcagct cctcagggtc 1500
cagcaactca ggatcccagc ccgggtctca ccctgggtct cagagtggct ccggggaacg 1560
cttcagagtg agatcatcat ccaagtctga aggctctcca tctcagcgcc tggaaaatgc 1620
agtgaaaaaa cctgaagata aaaaggaagt tttcagaccc ctcaagcctg ctggcgaagt 1680
ggatctgacc gcactggcca aagagcttcg agcagtggaa gatgtacggc cacctcacaa 1740
agtaacggac tactcctcat ccagtgagga gtcggggacg acggatgagg aggacgacga 1800

-continued

```
tgtggagcag gaaggggctg acgagtccac ctcaggacca gaggacacca gagcagcgtc   1860

atctctgaat ttgagcaatg gtgaaacgga atctgtgaaa accatgattg tccatgatga   1920

tgtagaaagt gagccggcca tgaccccatc caaggagggc actctaatcg tccgccagac   1980

tcagtccgct agtagcacac tccagaaaca caaatcttcc tcctccttta caccttttat   2040

agaccccaga ttactacaga tttctccatc tagcggaaca acagtgacat ctgtggtggg   2100

attttcctgt gatgggatga gaccagaagc cataaggcaa gatcctaccc ggaaaggctc   2160

agtggtcaat gtgaatccta ccaacactag gccacagagt gacaccccgg agattcgtaa   2220

atacaagaag aggtttaact ctgagattct gtgtgctgcc ttatggggag tgaatttgct   2280

agtgggtaca gagagtggcc tgatgctgct ggacagaagt ggccaaggga aggtctatcc   2340

tcttatcaac cgaagacgat ttcaacaaat ggacgtactt gagggcttga atgtcttggt   2400

gacaatatct ggcaaaaagg ataagttacg tgtctactat ttgtcctggt taagaaataa   2460

aatacttcac aatgatccag aagttgagaa gaagcaggga tggacaaccg taggggattt   2520

ggaaggatgt gtacattata aagttgtaaa atatgaaaga atcaaatttc tggtgattgc   2580

tttgaagagt tctgtggaag tctatgcgtg ggcaccaaag ccatatcaca aatttatggc   2640

ctttaagtca tttggagaat tggtacataa gccattactg gtggatctca ctgttgagga   2700

aggccagagg ttgaaagtga tctatggatc ctgtgctgga ttccatgctg ttgatgtgga   2760

ttcaggatca gtctatgaca tttatctacc aacacatatc cagtgtagca tcaaacccca   2820

tgcaatcatc atcctcccca atacagatgg aatggagctt ctggtgtgct atgaagatga   2880

gggggtttat gtaaacacat atggaaggat ccaccaagga tgtagttcta cagtggggag   2940

agatgcctac atcagtagca tatattcgat ccaatcagac aatgggctgg ggagagaagg   3000

ccatagagat ccgatctgtg gaaactggtc acttggatgg tgtgttcatg cacaaaaggg   3060

ctcaaagact aaaattcttg tgtgaacgca atgacaaggt gttctttgcc tctgttcggt   3120

ctggtggcag cagtcaggtt tatttcatga ccttaggcag gacttctctt ctgagctggt   3180

agaagcagtg tgatccaggg attactggcc tccagagtct tcaagatcct gagaacttgg   3240

aattccttgt aactggagct cggagctgca ccgagggcaa ccaggacagc tgtgtgtgca   3300

gacctcatgt gttgggttct ctcccctcct tcctgttcct cttatatacc agtttatccc   3360

cattcttttt ttttttctta ctccaaaata aatcaaggct gcaatgcagc tggtgctgtt   3420

cagattctaa aaaaaaaaaa aaaaaaaa                                      3448
```

<210> SEQ ID NO 17
<211> LENGTH: 2667
<212> TYPE: DNA
<213> ORGANISM: Homo sapiens

<400> SEQUENCE: 17

```
atataaaagg caactgctgg cagagagaca gaagcggatt gagcagcaga aagaacagag     60

gcgacggcta gaagagcaac aaaggagaga gcgggaagct agaaggcagc aggaacgtga    120

acagcgaagg agagaacaag aagaaaagag gcgtctagag gagttggaga gaaggcgcaa    180

agaagaagag gagaggagac gggcagaaga agaaaagagg agagttgaaa gagaacagga    240

gtatatcagg cgacagctag aagaggagca acggcacttg gaagtccttc agcagcagct    300

gctccaggag caggccatgt tactggagtg ccgatggcgg gagatggagg agcaccggca    360

ggcagagagg ctccagaggc agttgcaaca agaacaagca tatctcctgt ctctacagca    420

tgaccatagg aggccgcacc cgcagcactc gcagcagccg ccaccaccgc agcaggaaag    480
```

-continued

```
gagcaagcca agcttccatg ctcccgagcc caaagcccac tacgagcctg ctgaccgagc    540
gcgagaggtt cctgtgagaa caacatctcg ctcccctgtt ctgacccgtc gagattcccc    600
actgcagggc agtgggcagc agaatagcca ggcaggacag agaaactcca ccagtattga    660
gcccaggctt ctgtgggaga gagtggagaa gctggtgccc agacctggca gtggcagctc    720
ctcagggtcc agcaactcag gatcccagcc cgggtctcac cctgggtctc agagtggctc    780
cggggaacgc ttcagagtga gatcatcatc caagtctgaa ggctctccat ctcagcgcct    840
ggaaaatgca gtgaaaaaac ctgaagataa aaaggaagtt ttcagacccc tcaagcctgc    900
tgatctgacc gcactggcca aagagcttcg agcagtggaa gatgtacggc cacctcacaa    960
agtaacggac tactcctcat ccagtgagga gtcggggacg acggatgagg aggacgacga   1020
tgtggagcag gaaggggctg acgagtccac ctcaggacca gaggacacca gagcagcgtc   1080
atctctgaat ttgagcaatg gtgaaacgga atctgtgaaa accatgattg tccatgatga   1140
tgtagaaagt gagccggcca tgaccccatc caaggagggc actctaatcg tccgccagac   1200
tcagtccgct agtagcacac tccagaaaca caaatcttcc tcctccttta caccttttat   1260
agaccccaga ttactacaga tttctccatc tagcggaaca acagtgacat ctgtggtggg   1320
attttcctgt gatgggatga gaccagaagc cataaggcaa gatcctaccc ggaaaggctc   1380
agtggtcaat gtgaatccta ccaacactag gccacagagt gacaccccgg agattcgtaa   1440
atacaagaag aggtttaact ctgagattct gtgtgctgcc ttatggggag tgaatttgct   1500
agtgggtaca gagagtggcc tgatgctgct ggacagaagt ggccaaggga aggtctatcc   1560
tcttatcaac cgaagacgat ttcaacaaat ggacgtactt gagggcttga atgtcttggt   1620
gacaatatct ggcaaaaagg ataagttacg tgtctactat ttgtcctggt taagaaataa   1680
aatacttcac aatgatccag aagttgagaa gaagcaggga tggacaaccg taggggattt   1740
ggaaggatgt gtacattata aagttgtaaa atatgaaaga atcaaatttc tggtgattgc   1800
tttgaagagt tctgtggaag tctatgcgtg ggcaccaaag ccatatcaca aatttatggc   1860
ctttaagtca tttggagaat tggtacataa gccattactg gcggatctca ctgttgagga   1920
aggccagagg ttgaaagtga tctatggatc ctgtgctgga ttccatgctg ttgatgtgga   1980
ttcaggatca gtctatgaca tttatctacc aacacatatc cagtgtagca tcaaacccca   2040
tgcaatcatc atcctcccca atacagatgg aatggagctt ctggtgtgct atgaagatga   2100
gggggtttat gtaaacacat atggaaggat caccaaggat gtagttctac agtggggaga   2160
gatgcctaca tcagtagcat atattcgatc caatcagaca atgggctggg gagagaaggc   2220
catagagatc cgatctgtgg aaactggtca cttggatggt gtgttcatgc acaaaagggc   2280
tcaaagacta aaattcttgt gtgaacgcaa tgacaaggtg ttctttgcct ctgttcggtc   2340
tggtggcagc agtcaggttt atttcatgac cttaggcagg acttctcttc tgagctggta   2400
gaagcagtgt gatccaggga ttactggcct ccagagtctt caagatcctg agaacttgga   2460
attccttgta actggagctc ggagctgcac cgagggcaac caggacagct gtgtgtgcag   2520
acctcatgtg ttgggttctc tcccctcctt cctgttcctc ttatatacca gtttatcccc   2580
attctttttt tttttcttac tccaaaataa atcaaggctg caatgcagct ggtgctgttc   2640
agattctaaa aaaaaaaaaa aaaaaaa                                       2667
```

<210> SEQ ID NO 18
<211> LENGTH: 2034
<212> TYPE: DNA
<213> ORGANISM: Homo sapiens

<400> SEQUENCE: 18
agcagaatag ccaggcagga cagagaaact ccaccagcag tattgagccc aggcttctgt 60
gggagagagt ggagaagctg gtgcccagac ctggcagtgg cagctcctca gggtccagca 120
actcaggatc ccagcccggg tctcaccctg ggtctcagag tggctccggg gaacgcttca 180
gagtgagatc atcatccaag tctgaaggct ctccatctca gcgcctggaa aatgcagtga 240
aaaaacctga agataaaaag gaagttttca gacccctcaa gcctgctgat ctgaccgcac 300
tggccaaaga gcttcgagca gtggaagatg tacggccacc tcacaaagta acggactact 360
cctcatccag tgaggagtcg gggacgacgg atgaggagga cgacgatgtg gagcaggaag 420
gggctgacga gtccacctca ggaccagagg acaccagagc agcgtcatct ctgaatttga 480
gcaatggtga aacggaatct gtgaaaacca tgattgtcca tgatgatgta gaaagtgagc 540
cggccatgac cccatccaag gagggcactc taatcgtccg ccagactcag tccgctagta 600
gcacactcca gaaacacaaa tcttcctcct cctttacacc ttttatagac cccagattac 660
tacagatttc tccatctagc ggaacaacag tgacatctgt ggtgggattt tcctgtgatg 720
ggatgagacc agaagccata aggcaagatc ctacccggaa aggctcagtg gtcaatgtga 780
atcctaccaa cactaggcca cagagtgaca ccccggagat tcgtaaatac aagaagaggt 840
ttaactctga gattctgtgt gctgccttat ggggagtgaa tttgctagtg ggtacagaga 900
gtggcctgat gctgctggac agaagtggcc aagggaaggt ctatcctctt atcaaccgaa 960
gacgatttca acaaatggac gtacttgagg gcttgaatgt cttggtgaca atatctggca 1020
aaaaggataa gttacgtgtc tactatttgt cctggttaag aaataaaata cttcacaatg 1080
atccagaggt tgagaagaag cagggatgga caaccgtagg ggatttggaa ggatgtgtac 1140
attataaagt tgtaaaatat gaaagaatca aatttctggt gattgctttg aagagttctg 1200
tggaagtcta tgcgtgggca ccaaagccat atcacaaatt tatggccttt aagtcatttg 1260
gagaattggt acataagcca ttactggtgg atctcactgt tgaggaaggc cagaggttga 1320
aagtgatcta tggatcctgt gctggattcc atgctgttga tgtggattca ggatcagtct 1380
atgacattta tctaccaaca catatccagt gtagcatcaa accccatgca atcatcatcc 1440
tccccaatac agatggaatg gagcttctgg tgtgctatga agatgagggg gtttatgtaa 1500
acacatatgg aaggatcacc aaggatgtag ttctacagtg gggagagatg cctacatcag 1560
tagcatatat tcgatccaat cagacaatgg gctggggaga gaaggccata gagatccgat 1620
ctgtggaaac tggtcacttg gatggtgtgt tcatgcacaa aagggctcaa agactaaaat 1680
tcttgtgtga acgcaatgac aaggtgttct ttgcctctgt tcggtctggt ggcagcagtc 1740
aggtttattt catgacctta ggcaggactt ctcttctgag ctggtagaag cagtgtgatc 1800
cagggattac tggcctccag agtcttcaag atcctgagaa cttggaattc cttgtaactg 1860
gagctcggag ctgcaccgag ggcaaccagg acagctgtgt gtgcagacct catgtgttgg 1920
gttctctccc ctccttcctg ttcctcttat ataccagttt atccccattc tttttttttt 1980
ttcttactcc aaaataaatc aaggctgcaa tgcagctggt gctgttcaga ttct 2034

<210> SEQ ID NO 19
<211> LENGTH: 4284
<212> TYPE: DNA
<213> ORGANISM: Homo sapiens

<400> SEQUENCE: 19
cacagagcga cagagacatt tattgttatt tgttttttgg tggcaaaaag ggaaaatggc 60

```
gaacgactcc cctgcaaaaa gtctggtgga catcgacctc tcctccctgc gggatcctgc    120
tgggattttt gagctggtgg aagtggttgg aaatggcacc tatggacaag tctataaggg    180
tcgacatgtt aaaacgggtc agttggcagc catcaaagtt atggatgtca ctgaggatga    240
agaggaagaa atcaaactgg agataaatat gctaaagaaa tactctcatc acagaaacat    300
tgcaacatat tatggtgctt tcatcaaaaa gagccctcca ggacatgatg accaactctg    360
gcttgttatg gagttctgtg gggctgggtc cattacagac cttgtgaaga acaccaaagg    420
gaacacactc aaagaagact ggatcgctta catctccaga gaaatcctga ggggactggc    480
acatcttcac attcatcatg tgattcaccg ggatatcaag ggccagaatg tgttgctgac    540
tgagaatgca gaggtgaaac ttgttgactt tggtgtgagt gctcagctgg acaggactgt    600
ggggcggaga aatacgttca taggcactcc ctactggatg gctcctgagg tcatcgcctg    660
tgatgagaac ccagatgcca cctatgatta cagaagtgat ctttggtctt gtggcattac    720
agccattgag atggcagaag gtgctccccc tctctgtgac atgcatccaa tgagagcact    780
gtttctcatt cccagaaacc ctcctccccg gctgaagtca aaaaaatggt cgaagaagtt    840
ttttagtttt atagaagggt gcctggtgaa gaattacatg cagcggccct ctacagagca    900
gcttttgaaa catcctttta taagggatca gccaaatgaa aggcaagtta gaatccagct    960
taaggatcat atagatcgta ccaggaagaa gagaggcgag aaagatgaaa ctgagtatga   1020
gtacagtggg agtgaggaag aagaggagga agtgcctgaa caggaaggag agccaagttc   1080
cattgtgaac gtgcctggtg agtctactct tcgccgagat ttcctgagac tgcagcagga   1140
gaacaaggaa cgttccgagg ctcttcggag acaacagtta ctacaggagc aacagctccg   1200
ggagcaggaa gaatataaaa ggcaactgct ggcagagaga cagaagcgga ttgagcagca   1260
gaaagaacag aggcgacggc tagaagagca acaaaggaga gagcgggaag ctagaaggca   1320
gcaggaacgt gaacagcgaa ggagagaaca agaagaaaag aggcgtctag aggagttgga   1380
gagaaggcgc aaagaagaag aggagaggag acgggcagaa gaagaaaaga ggagagttga   1440
aagagaacag gagtatatca ggcgacagct agaagaggag cagcggcact tggaagtcct   1500
tcagcagcag ctgctccagg agcaggccat gttactggag tgccgatggc gggagatgga   1560
ggagcaccgg caggcagaga ggctccagag gcagttgcaa caagaacaag catatctcct   1620
gtctctacag catgaccata ggaggccgca cccgcagcac tcgcagcagc cgccaccacc   1680
gcagcaggaa aggagcaagc caagcttcca tgctcccgag cccaaagccc actacgagcc   1740
tgctgaccga gcgcgagagg tggaagatag atttaggaaa actaaccaca gctcccctga   1800
agcccagtct aagcagacag gcagagtatt ggagccacca gtgccttccc gatcagagtc   1860
tttttccaat ggcaactccg agtctgtgca tcccgccctg cagagaccag cggagccaca   1920
ggtacagtgg tcccacctgg catctctcaa gaacaatgtt tcccctgtct cgcgatccca   1980
ttccttcagt gacccttctc ccaaatttgc acaccaccat cttcgttctc aggacccatg   2040
tccaccttcc cgcagtgagg tgctcagtca gagctctgac tctaagtcag aggcgcctga   2100
ccctacccaa aaggcttggt ctagatcaga cagtgacgag gtgcctccaa gggttcctgt   2160
gagaacaaca tctcgctccc ctgttctgtc ccgtcgagat tccccactgc agggcagtgg   2220
gcagcagaat agccaggcag gacagagaaa ctccaccagc agtattgagc ccaggcttct   2280
gtgggagaga gtggagaagc tggtgcccag acctggcagt ggcagctcct cagggtccag   2340
caactcagga tcccagcccg ggtctcaccc tgggtctcag agtggctccg gggaacgctt   2400
cagagtgaga tcatcatcca agtctgaagg ctctccatct cagcgcctgg aaaatgcagt   2460
```

```
gaaaaaacct gaagataaaa aggaagtttt cagacccctc aagcctgctg gcgaagtgga   2520
tctgaccgca ctggccaaag agcttcgagc agtggaagat gtacggccac ctcacaaagt   2580
aacggactac tcctcatcca gtgaggagtc ggggacgacg gatgaggagg acgacgatgt   2640
ggagcaggaa ggggctgacg agtccacctc aggaccagag gacaccagag cagcgtcatc   2700
tctgaatttg agcaatggtg aaacggaatc tgtgaaaacc atgattgtcc atgatgatgt   2760
agaaagtgag ccggccatga ccccatccaa ggagggcact ctaatcgtcc gccagactca   2820
gtccgctagt agcacactcc agaaacacaa atcttcctcc tcctttacac cttttataga   2880
ccccagatta ctacagattt ctccatctag cggaacaaca gtgacatctg tggtgggatt   2940
ttcctgtgat gggatgagac cagaagccat aaggcaagat cctacccgga aaggctcagt   3000
ggtcaatgtg aatcctacca acactaggcc acagagtgac accccggaga ttcgtaaata   3060
caagaagagg tttaactctg agattctgtg tgctgcctta tggggagtga atttgctagt   3120
gggtacagag agtggcctga tgctgctgga cagaagtggc caagggaagg tctatcctct   3180
tatcaaccga agacgatttc aacaaatgga cgtacttgag ggcttgaatg tcttggtgac   3240
aatatctggc aaaaaggata agttacgtgt ctactatttg tcctggttaa gaaataaaat   3300
acttcacaat gatccagaag ttgagaagaa gcagggatgg acaaccgtag gggatttgga   3360
aggatgtgta cattataaag ttgtaaaata tgaaagaatc aaatttctgg tgattgcttt   3420
gaagagttct gtggaagtct atgcgtgggc accaaagcca tatcacaaat ttatggcctt   3480
taagtcattt ggagaattgg tacataagcc attactggtg gatctcactg ttgaggaagg   3540
ccagaggttg aaagtgatct atggatcctg tgctggattc catgctgttg atgtggattc   3600
aggatcagtc tatgacattt atctaccaac acatatccag tgtagcatca aaccccatgc   3660
aatcatcatc ctccccaata cagatggaat ggagcttctg gtgtgctatg aagatgaggg   3720
ggtttatgta aacacatatg gaaggatcac caaggatgta gttctacagt ggggagagat   3780
gcctacatca gtagcatata ttcgatccaa tcagacaatg ggctggggag agaaggccat   3840
agagatccga tctgtggaaa ctggtcactt ggatggtgtg ttcatgcaca aaagggctca   3900
aagactaaaa ttcttgtgtg aacgcaatga caaggtgttc tttgcctctg ttcggtctgg   3960
tggcagcagt caggtttatt tcatgacctt aggcaggact tctcttctga gctggtagaa   4020
gcagtgtgat ccagggatta ctggcctcca gagtcttcaa gatcctgaga acttggaatt   4080
ccttgtaact ggagctcgga gctgcaccga gggcaaccag gacagctgtg tgtgcagacc   4140
tcatgtgttg ggttctctcc cctccttcct gttcctctta tataccagtt tatccccatt   4200
cttttttttt ttcttactcc aaaataaatc aaggctgcaa tgcagctggt gctgttcaga   4260
ttctaaaaaa aaaaaaaaaa aaaa                                           4284
```

<210> SEQ ID NO 20
<211> LENGTH: 3940
<212> TYPE: DNA
<213> ORGANISM: Homo sapiens

<400> SEQUENCE: 20

```
cacagagcga cagagacatt tattgttatt tgtttttttgg tggcaaaaag ggaaaatggc     60
gaacgactcc cctgcaaaaa gtctggtgga catcgacctc tcctccctgc gggatcctgc    120
tgggattttt gagctggtgg aagtggttgg aaatggcacc tatggacaag tctataaggg    180
tcgacatgtt aaaacgggtc agttggcagc catcaaagtt atggatgtca ctgaggatga    240
agaggaagaa atcaaactgg agataaatat gctaaagaaa tactctcatc acagaaacat    300
```

-continued

```
tgcaacatat tatggtgctt tcatcaaaaa gagccctcca ggacatgatg accaactctg    360
gcttgttatg gagttctgtg gggctgggtc cattacagac cttgtgaaga acaccaaagg    420
gaacacactc aaagaagact ggatcgctta catctccaga gaaatcctga ggggactggc    480
acatcttcac attcatcatg tgattcaccg ggatatcaag ggccagaatg tgttgctgac    540
tgagaatgca gaggtgaaac ttgttgactt tggtgtgagt gctcagctgg acaggactgt    600
ggggcggaga aatacgttca taggcactcc ctactggatg gctcctgagg tcatcgcctg    660
tgatgagaac ccagatgcca cctatgatta cagaagtgat ctttggtctt gtggcattac    720
agccattgag atggcagaag gtgctccccc tctctgtgac atgcatccaa tgagagcact    780
gtttctcatt cccagaaacc ctcctccccg gctgaagtca aaaaaatggt cgaagaagtt    840
ttttagtttt atagaagggt gcctggtgaa gaattacatg cagcggccct ctacagagca    900
gcttttgaaa catcctttta taagggatca gccaaatgaa aggcaagtta gaatccagct    960
taaggatcat atagatcgta ccaggaagaa gagaggcgag aaagatgaaa ctgagtatga   1020
gtacagtggg agtgaggaag aagaggagga agtgcctgaa caggaaggag agccaagttc   1080
cattgtgaac gtgcctggtg agtctactct tcgccgagat ttcctgagac tgcagcagga   1140
gaacaaggaa cgttccgagg ctcttcggag acaacagtta ctacaggagc aacagctccg   1200
ggagcaggaa gaatataaaa ggcaactgct ggcagagaga cagaagcgga ttgagcagca   1260
gaaagaacag aggcgacggc tagaagagca acaaaggaga gagcgggaag ctagaaggca   1320
gcaggaacgt gaacagcgaa ggagagaaca agaagaaaag aggcgtctag aggagttgga   1380
gagaaggcgc aaagaagaag aggagaggag acgggcagaa gaagaaaaga ggagagttga   1440
aagagaacag gagtatatca ggcgacagct agaagaggag cagcggcact tggaagtcct   1500
tcagcagcag ctgctccagg agcaggccat gttactgcat gaccatagga ggccgcaccc   1560
gcagcactcg cagcagccgc caccaccgca gcaggaaagg agcaagccaa gcttccatgc   1620
tcccgagccc aaagcccact acgagcctgc tgaccgagcg cgagaggtgg aagatagatt   1680
taggaaaact aaccacagct cccctgaagc ccagtctaag cagacaggca gagtattgga   1740
gccaccagtg ccttcccgat cagagtcttt ttccaatggc aactccgagt ctgtgcatcc   1800
cgccctgcag agaccagcgg agccacaggt tcctgtgaga acaacatctc gctcccctgt   1860
tctgtcccgt cgagattccc cactgcaggg cagtgggcag cagaatagcc aggcaggaca   1920
gagaaactcc accagcagta ttgagcccag gcttctgtgg gagagagtgg agaagctggt   1980
gcccagacct ggcagtggca gctcctcagg gtccagcaac tcaggatccc agcccgggtc   2040
tcaccctggg tctcagagtg gctccgggga acgcttcaga gtgagatcat catccaagtc   2100
tgaaggctct ccatctcagc gcctggaaaa tgcagtgaaa aaacctgaag ataaaaagga   2160
agttttcaga cccctcaagc ctgctggcga agtggatctg accgcactgg ccaaagagct   2220
tcgagcagtg gaagatgtac ggccacctca caaagtaacg gactactcct catccagtga   2280
ggagtcgggg acgacggatg aggaggacga cgatgtggag caggaagggg ctgacgagtc   2340
cacctcagga ccagaggaca ccagagcagc gtcatctctg aatttgagca atggtgaaac   2400
ggaatctgtg aaaaccatga ttgtccatga tgatgtagaa agtgagccgg ccatgacccc   2460
atccaaggag ggcactctaa tcgtccgcca gactcagtcc gctagtagca cactccagaa   2520
acacaaatct tcctcctcct ttacaccttt tatagacccc agattactac agatttctcc   2580
atctagcgga acaacagtga catctgtggt gggattttcc tgtgatggga tgagaccaga   2640
agccataagg caagatccta cccggaaagg ctcagtggtc aatgtgaatc ctaccaacac   2700
```

```
taggccacag agtgacaccc cggagattcg taaatacaag aagaggttta actctgagat   2760
tctgtgtgct gccttatggg gagtgaattt gctagtgggt acagagagtg gcctgatgct   2820
gctggacaga agtggccaag ggaaggtcta tcctcttatc aaccgaagac gatttcaaca   2880
aatggacgta cttgagggct tgaatgtctt ggtgacaata tctggcaaaa aggataagtt   2940
acgtgtctac tatttgtcct ggttaagaaa taaaatactt cacaatgatc cagaagttga   3000
gaagaagcag ggatggacaa ccgtagggga tttggaagga tgtgtacatt ataaagttgt   3060
aaaatatgaa agaatcaaat ttctggtgat tgctttgaag agttctgtgg aagtctatgc   3120
gtgggcacca aagccatatc acaaatttat ggcctttaag tcatttggag aattggtaca   3180
taagccatta ctggtggatc tcactgttga ggaaggccag aggttgaaag tgatctatgg   3240
atcctgtgct ggattccatg ctgttgatgt ggattcagga tcagtctatg acatttatct   3300
accaacacat atccagtgta gcatcaaacc ccatgcaatc atcatcctcc ccaatacaga   3360
tggaatggag cttctggtgt gctatgaaga tgagggggtt tatgtaaaca catatggaag   3420
gatcaccaag gatgtagttc tacagtgggg agagatgcct acatcagtag catatattcg   3480
atccaatcag acaatgggct ggggagagaa ggccatagag atccgatctg tggaaactgg   3540
tcacttggat ggtgtgttca tgcacaaaag ggctcaaaga ctaaaattct tgtgtgaacg   3600
caatgacaag gtgttctttg cctctgttcg gtctggtggc agcagtcagg tttatttcat   3660
gaccttaggc aggacttctc ttctgagctg gtagaagcag tgtgatccag ggattactgg   3720
cctccagagt cttcaagatc ctgagaactt ggaattcctt gtaactggag ctcggagctg   3780
caccgagggc aaccaggaca gctgtgtgtg cagacctcat gtgttgggtt ctctcccctc   3840
cttcctgttc ctcttatata ccagtttatc cccattcttt tttttttct tactccaaaa   3900
taaatcaagg ctgcaatgca gctggtgctg ttcagattct                        3940
```

<210> SEQ ID NO 21
<211> LENGTH: 3888
<212> TYPE: DNA
<213> ORGANISM: Homo sapiens

<400> SEQUENCE: 21

```
atgggcgacc cagcccccgc ccgcagcctg gacgacatcg acctgtccgc cctgcgggac     60
cctgctggga tctttgagct tgtggaggtg gtcggcaatg gaacctacgg acaggtgtac    120
aagggtcggc atgtcaagac ggggcagctg gctgccatca aggtcatgga tgtcacggag    180
gacgaggagg aagagatcaa acaggagatc aacatgctga aaaagtactc tcaccaccgc    240
aacatcgcca cctactacgg agccttcatc aagaagagcc ccccgggaaa cgatgaccag    300
ctctggctgg tgatggagtt ctgtggtgct ggttcagtga ctgacctggt aaagaacaca    360
aaaggcaacg ccctgaagga ggactgtatc gcctatatct gcagggagat cctcaggggt    420
ctggcccatc tccatgccca caaggtgatc catcgagaca tcaaggggca gaatgtgctg    480
ctgacagaga atgctgaggt caagctagtg gattttgggg tgagtgctca gctggaccgc    540
accgtgggca gacggaacac tttcattggg actccctact ggatggctcc agaggtcatc    600
gcctgtgatg agaaccctga tgccacctat gattacagga gtgatatttg gtctctagga    660
atcacagcca tcgagatggc agagggagcc ccccctctgt gtgacatgca ccccatgcga    720
gccctcttcc tcattcctcg gaaccctccg cccaggctca agtccaagaa gtggtctaag    780
aagttcattg acttcattga cacatgtctc atcaagactt acctgagccg cccacccacg    840
gagcagctac tgaagtttcc cttcatccgg gaccagccca cggagcggca ggtccgcatc    900
```

-continued

```
cagcttaagg accacattga ccgatcccgg aagaagcggg gtgagaaaga ggagacagaa    960
tatgagtaca gcggcagcga ggaggaagat gacagccatg gagaggaagg agagccaagc   1020
tccatcatga acgtgcctgg agagtcgact ctacgccggg agtttctccg gctccagcag   1080
gaaaataaga gcaactcaga ggctttaaaa cagcagcagc agctgcagca gcagcagcag   1140
cgagaccccg aggcacacat caaacacctg ctgcaccagc ggcagcggcg catagaggag   1200
cagaaggagg agcggcgccg cgtggaggag caacagcggc gggagcggga gcagcggaag   1260
ctgcaggaga aggagcagca gcggcggctg gaggacatgc aggctctgcg gcgggaggag   1320
gagcggcggc aggcggagcg cgagcaggaa tacaagcgga agcagctgga ggagcagcgg   1380
cagtcagaac gtctccagag gcagctgcag caggagcatg cctacctcaa gtccctgcag   1440
cagcagcaac agcagcagca gcttcagaaa cagcagcagc agcagctcct gcctggggac   1500
aggaagcccc tgtaccatta tggtcggggc atgaatcccg ctgacaaacc agcctgggcc   1560
cgagaggtag aagagagaac aaggatgaac aagcagcaga actctccctt ggccaagagc   1620
aagccaggca gcacggggcc tgagcccccc atcccccagg cctccccagg gcccccagga   1680
ccccttccc agactcctcc tatgcagagg ccggtggagc cccaggaggg accgcacaag    1740
agcctggtgg cacaccgggt cccactgaag ccatatgcag cacctgtacc ccgatcccag   1800
tccctgcagg accagcccac ccgaaacctg gctgccttcc cagcctccca tgaccccgac   1860
cctgccatcc ccgcacccac tgccacgccc agtgcccgag gagctgtcat ccgccagaat   1920
tcagacccca cctctgaagg acctggcccc agcccgaatc cccagcctg ggtccgccca    1980
gataacgagg ccccacccaa ggtgcctcag aggacctcat ctatcgccac tgcccttaac   2040
accagtgggg ccggagggtc ccggccagcc caggcagtcc gtgccagtaa ccccgacctc   2100
aggaggagcg accctggctg ggaacgctcg gacagcgtcc ttccagcctc tcacgggcac   2160
ctcccccagg ctggctcact ggagcggaac cgcgtgggag tctcctccaa accggacagc   2220
tcccctgtgc tctcccctgg gaataaagcc aagcccgacg accaccgctc acggccaggc   2280
cggcccgcag actttgtgtt gctgaaagag cggactctgg acgaggcccc tcggcctccc   2340
aagaaggcca tggactactc gtcgtccagc gaggaggtgg aaagcagtga ggacgacgag   2400
gaggaaggcg aaggcgggcc agcagagggg agcagagata cccctggggg ccgcagcgat   2460
ggggatacag acagcgtcag caccatggtg gtccacgacg tcgaggagat caccgggacc   2520
cagcccccat acgggggcgg caccatggtg gtccagcgca cccctgaaga ggagcggaac   2580
ctgctgcatg ctgacagcaa tgggtacaca aacctgcctg acgtggtcca gcccagccac   2640
tcacccaccg agaacagcaa aggccaaagc ccaccctcga aggatgggag tggtgactac   2700
cagtctcgtg ggctggtaaa ggcccctggc aagagctcgt tcacgatgtt tgtggatcta   2760
gggatctacc agcctggagg cagtggggac agcatcccca tcacagccct agtgggtgga   2820
gagggcactc ggctcgacca gctgcagtac gacgtgagga agggttctgt ggtcaacgtg   2880
aatcccacca acacccgggc ccacagtgag acccctgaga tccggaagta caagaagcga   2940
ttcaactccg agatcctctg tgcagccctt tggggggtca acctgctggt gggcacggag   3000
aacgggctga tgttgctgga ccgaagtggg cagggcaagg tgtatggact cattgggcgg   3060
cgacgcttcc agcagatgga tgtgctggag gggctcaacc tgctcatcac catctcaggg   3120
aaaaggaaca aactgcgggt gtattacctg tcctggctcc ggaacaagat tctgcacaat   3180
gacccagaag tggagaagaa gcagggctgg accaccgtgg gggacatgga gggctgcggg   3240
cactaccgtg ttgtgaaata cgagcggatt aagttcctgg tcatcgccct caagagctcc   3300
```

```
gtggaggtgt atgcctgggc ccccaaaccc taccacaaat tcatggcctt caagtccttt   3360

gccgacctcc cccaccgccc tctgctggtc gacctgacag tagaggaggg gcagcggctc   3420

aaggtcatct atggctccag tgctggcttc catgctgtgg atgtcgactc ggggaacagc   3480

tatgacatct acatccctgt gcacatccag agccagatca cgccccatgc catcatcttc   3540

ctccccaaca ccgacggcat ggagatgctg ctgtgctacg aggacgaggg tgtctacgtc   3600

aacacgtacg ggcgcatcat taaggatgtg gtgctgcagt gggggggagat gcctacttct   3660

gtggcctaca tctgctccaa ccagataatg ggctggggtg agaaagccat tgagatccgc   3720

tctgtggaga cgggccacct cgacggggtc ttcatgcaca aacgagctca gaggctcaag   3780

ttcctgtgtg agcggaatga caaggtgttt tttgcctcag tccgctctgg gggcagcagc   3840

caagtttact tcatgactct gaaccgtaac tgcatcatga actggtga               3888
```

<210> SEQ ID NO 22
<211> LENGTH: 5014
<212> TYPE: DNA
<213> ORGANISM: Homo sapiens

<400> SEQUENCE: 22

```
ggctggctcc ggggagatag cgcctgtcag tcggtgggtc ggtcctcgcg ccggccctcc     60

ccctccccgg tctccggggg aggcgcggtg gagtccgccc ccggggttct ccgatggggg    120

agaagcggcg acggcggcag tggagtaacc gagccggagc gtgagcggcc ccggtgcccc    180

gttccccacg gaggccatgg gcgacccagc cccgcccgc agcctggacg acatcgacct    240

gtccgccctg cgggaccctg ctgggatctt tgagcttgtg gaggtggtcg gcaatggaac    300

ctacggacag gtgtacaagg gtcggcatgt caagacgggg cagctggctg ccatcaaggt    360

catggatgtc acggaggacg aggaggaaga gatcaaacag gagatcaaca tgctgaaaaa    420

gtactctcac caccgcaaca tcgccaccta ctacggagcc ttcatcaaga agagcccccc    480

gggaaacgat gaccagctct ggctggtgat ggagttctgt ggtgctggtt cagtgactga    540

cctggtaaag aacacaaaag gcaacgccct gaaggaggac tgtatcgcct atatctgcag    600

ggagatcctc aggggtctgg cccatctcca tgcccacaag gtgatccatc gagacatcaa    660

ggggcagaat gtgctgctga cagagaatgc tgaggtcaag ctagtggatt ttggggtgag    720

tgctcagctg gaccgcaccg tgggcagacg gaacactttc attgggactc cctactggat    780

ggctccagag gtcatcgcct gtgatgagaa ccctgatgcc acctatgatt acaggagtga    840

tatttggtct ctaggaatca cagccatcga gatggcagag ggagcccccc ctctgtgtga    900

catgcacccc atgcgagccc tcttcctcat tcctcggaac cctccgccca ggctcaagtc    960

caagaagtgg tctaagaagt tcattgactt cattgacaca tgtctcatca agacttacct   1020

gagccgccca cccacggagc agctactgaa gtttcccttc atccgggacc agcccacgga   1080

gcggcaggtc cgcatccagc ttaaggacca cattgaccga tcccggaaga agcggggtga   1140

gaaagaggag acagaatatg agtacagcgg cagcgaggag gaagatgaca gccatggaga   1200

ggaaggagag ccaagctcca tcatgaacgt gcctggagag tcgactctac gccgggagtt   1260

tctccggctc cagcaggaaa ataagagcaa ctcagaggct ttaaaacagc agcagcagct   1320

gcagcagcag cagcagcgag accccgaggc acacatcaaa cacctgctgc accagcggca   1380

gcggcgcata gaggagcaga aggaggagcg gcgccgcgtg gaggagcaac agcggcggga   1440

gcgggagcag cggaagctgc aggagaagga gcagcagcgg cggctggagg acatgcaggc   1500

tctgcggcgg gaggaggagc ggcggcaggc ggagcgcgag caggaataca agcggaagca   1560
```

-continued

```
gctggaggag cagcggcagt cagaacgtct ccagaggcag ctgcagcagg agcatgccta   1620
cctcaagtcc ctgcagcagc agcaacagca gcagcagctt cagaaacagc agcagcagca   1680
gctcctgcct ggggacagga agcccctgta ccattatggt cggggcatga atcccgctga   1740
caaaccagcc tgggcccgag aggtagaaga gagaacaagg atgaacaagc agcagaactc   1800
tcccttggcc aagagcaagc caggcagcac ggggcctgag ccccccatcc cccaggcctc   1860
cccagggccc ccaggacccc tttcccagac tcctcctatg cagaggccgg tggagcccca   1920
ggagggaccg cacaagagcc tggtggcaca ccgggtccca ctgaagccat atgcagcacc   1980
tgtaccccga tcccagtccc tgcaggacca gcccacccga aacctggctg ccttcccagc   2040
ctcccatgac cccgaccctg ccatccccgc acccactgcc acgcccagtg cccgaggagc   2100
tgtcatccgc cagaattcag accccacctc tgaaggacct ggccccagcc cgaatccccc   2160
agcctgggtc cgcccagata acgaggcccc acccaaggtg cctcagagga cctcatctat   2220
cgccactgcc cttaacacca gtggggccgg agggtcccgg ccagcccagg cagtccgtgc   2280
cagacctcgc agcaactccg cctggcaaat ctatctgcaa aggcgggcag agcggggcac   2340
cccaaagcct ccagggcccc ctgctcagcc ccctggcccg cccaacgcct ctagtaaccc   2400
cgacctcagg aggagcgacc ctggctggga acgctcggac agcgtccttc cagcctctca   2460
cgggcacctc ccccaggctg gctcactgga gcggaaccgc gtgggagcct cctccaaact   2520
ggacagctcc cctgtgctct cccctgggaa taaagccaag cccgacgacc accgctcacg   2580
gccaggccgg cccgcagact ttgtgttgct gaaagagcgg actctggacg aggcccctcg   2640
gcctcccaag aaggccatgg actactcgtc gtccagcgag gaggtggaaa gcagtgagga   2700
cgacgaggag gaaggcgaag gcgggccagc agaggggagc agagataccc ctgggggccg   2760
cagcgatggg gatacagaca gcgtcagcac catggtggtc cacgacgtcg aggagatcac   2820
cgggacccag cccccatacg ggggcggcac catggtggtc cagcgcaccc ctgaagagga   2880
gcggaacctg ctgcatgctg acagcaatgg gtacacaaac ctgcctgacg tggtccagcc   2940
cagccactca cccaccgaga acagcaaagg ccaaagccca ccctcgaagg atgggagtgg   3000
tgactaccag tctcgtgggc tggtaaaggc ccctggcaag agctcgttca cgatgtttgt   3060
ggatctaggg atctaccagc ctggaggcag tggggacagc atccccatca cagccctagt   3120
gggtggagag ggcactcggc tcgaccagct gcagtacgac gtgaggaagg gttctgtggt   3180
caacgtgaat cccaccaaca cccgggccca cagtgagacc cctgagatcc ggaagtacaa   3240
gaagcgattc aactccgaga tcctctgtgc agccctttgg ggggtcaacc tgctggtggg   3300
cacggagaac gggctgatgt tgctggaccg aagtgggcag ggcaaggtgt atggactcat   3360
tgggcggcga cgcttccagc agatggatgt gctggagggg ctcaacctgc tcatcaccat   3420
ctcagggaaa aggaacaaac tgcgggtgta ttacctgtcc tggctccgga acaagattct   3480
gcacaatgac ccagaagtgg agaagaagca gggctggacc accgtggggg acatggaggg   3540
ctgcgggcac taccgtgttg tgaaatacga gcggattaag ttcctggtca tcgccctcaa   3600
gagctccgtg gaggtgtatg cctgggcccc caaaccctac cacaaattca tggccttcaa   3660
gtcctttgcc gacctccccc accgccctct gctggtcgac ctgacagtag aggaggggca   3720
gcggctcaag gtcatctatg gctccagtgc tggcttccat gctgtggatg tcgactcggg   3780
gaacagctat gacatctaca tccctgtgca catccagagc cagatcacgc cccatgccat   3840
catcttcctc cccaacaccg acggcatgga gatgctgctg tgctacgagg acgagggtgt   3900
ctacgtcaac acgtacgggc gcatcattaa ggatgtggtg ctgcagtggg gggagatgcc   3960
```

tacttctgtg gcctacatct gctccaacca gataatgggc tggggtgaga aagccattga 4020
gatccgctct gtggagacgg gccacctcga cggggtcttc atgcacaaac gagctcagag 4080
gctcaagttc ctgtgtgagc ggaatgacaa ggtgtttttt gcctcagtcc gctctggggg 4140
cagcagccaa gtttacttca tgactctgaa ccgtaactgc atcatgaact ggtgacgggg 4200
ccctgggctg gggctgtccc acactggacc cagctctccc cctgcagcca ggcttcccgg 4260
gccgcccctc tttcccctcc ctgggctttt gcttttactg gtttgatttc actggagcct 4320
gctgggaacg tgacctctga cccctgatgc tttcgtgatc acgtgaccat cctcttcccc 4380
aacatgtcct cttcccaaaa ctgtgcctgt ccccagcttc tggggaggga cacagcttcc 4440
ccttcccagg aattgagtgg gcctagcccc tcccccttt tctccatttg agaggagagt 4500
gcttggggct tgaacccctt accccactgc tgctgactgg gcagggccct ggaccccttt 4560
atttgcacgt caggggagcc ggctcccccc ttgaatgtac cagaccctgg ggggggtcac 4620
tgggccctag atttttgggg ggtcaccagc cactccaggg gcagggacca tttcttcatt 4680
ttctgaaagc actttaatga ttccccttcc cccaaactcc agggaatgga ggggggaccc 4740
cgccagccaa aacattcccc ccattcccga cccccatctc ctcttctagc ccatgccctt 4800
ccccggtgga gggagggagc agggagccct cactctccac gccccttgct tgcatctgta 4860
tatagtgtga gcagcaagta acccttctcc tccctccccc ctcacccctc ctcaatgtag 4920
tggccttgga tatcctgttt gttaataaag acaattcaac cagcaaaaaa aaaaaaaaaa 4980
aaaaaaaaaa aaaaaaaaaa aaaaaaaaaa aaaa 5014

<210> SEQ ID NO 23
<211> LENGTH: 1665
<212> TYPE: DNA
<213> ORGANISM: Homo sapiens

<400> SEQUENCE: 23
gaagtgtccg actgggtgcg catggggaat gcccttgaca acatctgctt ctgggccgct 60
ctggtgctct tcagcgtggg ctccagcctc atcttcctcg ggcctactt caaccgagtg 120 cctgatctcc cctacgcgcc gtgtatccag ccttagctcg caccgacttc aatttcccac 180
ccatctccag taggaaattg attttgaaaa agtaggctgc cgccaccacg gcattatgat 240
cccttccccc tgctgatcaa tctgcagttt gtgaacttca caagaatggt gtgtgccctt 300
ccctggcgtg tgtaggcctg gccgcagtcc aggggtcagc aggaggaaag ggttcacata 360
ggctctcagg tgccagtctt ccagaaagca aggactgccc ttcattcagc cttgctgacc 420
tcccagcctt tctaaggctc agccccacgg gactctggtg gctgccagct tgtgagctat 480
ctatctatat tcatttcata gccaaacagg agaccccttt gcaggacttg cacacaggga 540
ggctgtagcc aggaaaccct cttcttccct ggtctggctc tgctggagcg ggtgggaacc 600
aaacaccttc agtgctggtg gccctcaggc ccacaggttt aaggctgagg ctgccctgac 660
ccttccacag tcatttcttc taggttttct tggcccagca ctgcccatcc caccccatga 720
ggctcactca ttgcagatcc cagcccaccc tgccccttc ttccccaccc tggaggctct 780
ctctgcctag tctacagtac tgacagaaag caaggacatg cggcctgcat ggtgggagct 840
ggttgaattg tctttattaa caaacaggat atccaaggcc actacattga ggaggggtgg 900
ggggggaggg agaagggtta cttgctgctc acactatata cagatgcaag caaggggcgt 960
ggagagtgag ggctccctgc tccctccctc caccggggaa gggcatgggc tagaagagga 1020
gaggggggtc gggaatgggg ggaatgtttt ggctggcggg gtcccccctc cattccctgg 1080

```
agtttggggg aaggggaatc attaaagtgc tttcagaaaa tgaagaaatg gtccctgccc   1140

ctggagtggc tggtgacccc ccaaaaatct agggcccagt gacccccccc agggtctggt   1200

acattcaagg ggggagccgg ctcccctgac gtgcaaataa aggggtccag ggccctgccc   1260

agtcagcagc agtggggtaa ggggttcaag ccccaagcac tctcctctca aatggagaaa   1320

agggggggagg ggctaggccc actcaattcc tgggaagggg aagctgtgtc cctccccaga  1380

agctggggac aggcacagtt ttgggaagag gacatgttgg ggaagaggat ggtcacgtga   1440

tcacgaaagc atcaggggtc agaggtcacg ttcccagcag gctccagtga aatcaaacca   1500

gtaaaagcaa aagcccaggg aggggaaaga ggggcggccc gggaagcctg gctgcagggg   1560

gagagctggg tccagtgtgg gacagcccca gcccagggcc ccgtcaccag ttcatgatgc   1620

agttacggtt cagagtcatg aagtaaactt ggctgctgcc cccag                   1665
```

<210> SEQ ID NO 24
<211> LENGTH: 3152
<212> TYPE: DNA
<213> ORGANISM: Homo sapiens

<400> SEQUENCE: 24

```
taaaggcccc tggcaagagc tcgttcacga tgtttgtgga tctagggatc taccagcctg     60

gaggcagtgg ggacagcatc cccatcacag gtgaggacag gaggacagac ctgctgtgag    120

gccagggtcc aggggcagcc tggaggggag cacagtggtc ttgagacgca gcctcacaaa    180

gcatagccac aggacctctc ccttgggccc tagcacctgc ctgggcacag aggcaaggaa    240

gagcctctga gacccctcct tcctgtccca caggacagga aatgctcaga gttgccaggg    300

gacctgggca aagactcaaa gctaacaagt gacagaaatg ggacttgagc cagacctttt    360

gactccaagt ccagcactct atccccctct cccatgcacc tcctctcctc ctgtctttct    420

cctcctttct gcgtattatg aggtgccaag acctgatata ggggatggag gtaaaaagag    480

atggggtgag aagctgcagc ccctcctccc acctcctcct ccttctggca gccctagtgg    540

gtggagaggg cactcggctc gaccagctgc agtacgacgt gaggaagggt tctgtggtca    600

acgtgaatcc caccaacacc cgggcccaca gtgagacccc tgagatccgg aagtacaaga    660

agcgattcaa ctccgagatc ctctgtgcag ccctttgggg ggtcaacctg ctggtgggca    720

cggagaacgg gctgatgttg ctggaccgaa gtgggcaggg caaggtgtat ggactcattg    780

ggcggcgacg cctccagcag atggatgtgc tggaggggct caacctgctc atcaccatct    840

caggtacagg tgtggtgagt gggggaggga ggaggggctc agctccttgg cgctgtcacc    900

atcttctgcc tgggaggagg gcaggcactg gaaggtgggg ccacactttc tcacccccttg   960

tggtatgctg acagaggagg ccagggcggt ggcattcggg cctcagatga gaatgggggc   1020

gggtgtgtat gtctgtccgt ccctcaggga aaaggaacaa actgcgggtg tattacctgt   1080

cctggctccg gaacaagatt ctgcacaatg acccagaagt ggagaagaag cagggctgga   1140

ccaccgtggg ggacatggag ggctgcgggc actaccgtgt tggtgaggat gtcccaacag   1200

agtggccagc gcatacttgt tcatgaagag agaaatggat ctgggagcca gggacttggg   1260

gcctgggtgg ggcagtgtag tgacagacca cggggaggcg cccgtggcgc aagaagggaa   1320

gtctcagcat ccctcttctc tcccgccccc agtgaaatac gagcggatta agttcctggt   1380

catcgccctc aagagctccg tggaggtgta tgcctgggcc cccaaaccct accacaaatt   1440

catggccttc aagtcctttg ccgacctccc ccaccgccct ctgctggtcg acctgacagt   1500

agaggagggg cagcggctca aggtcatcta tggctccagt gctggcttcc atgctgtgga   1560
```

tgtcgactcg gggaacagct atgacatcta catccctgtg cacatccaga gccagatcac 1620
gccccatgcc atcatcttcc tccccaacac cgacggcatg gagatgctgc tgtgctacga 1680
ggacgagggt gtctacgtca acacgtacgg gcgcatcatt aaggatgtgg tgctgcagtg 1740
gggggagatg cctacttctg tggcctacat ctgctccaac cagataatgg gctggggtga 1800
gaaagccatt gagatccgct ctgtggagac gggccacctc gacggggtct tcatgcacaa 1860
acgagctcag aggctcaagt tcctgtgtga gcggaatgac aaggtgggag gctccttccc 1920
tctgaaagcc ctgctgtccc ggctgccatg accctaggcc cctgggcaga gttctgggga 1980
gaggatggtg gtggtggctt cctaaaagcg ggcccctctg ggagctcgga gggcagtcag 2040
ccactaccac tgccctgcgc tcccttcaga ttccgaggac ttcctagctg gcccccagag 2100
ggcgagtggt gcaccctctc ccctaacatc ccagcctgcc tttcctccgg gtgaggggca 2160
ctgtgagtct cctcctgcag tctctgtgtc tccctcaact cttctgccac cccttcttcc 2220
cttctttccc tctcccagtt gagacacccc cccaacctca gcccttggtg acttcttctc 2280
ctgccccacc caggtgtttt ttgcctcagt ccgctctggg ggcagcagcc aagtttactt 2340
catgactctg aaccgtaact gcatcatgaa ctggtgacgg ggccctgggc tggggctgtc 2400
ccacactgga cccagctctc cccctgcagc caggcttccc gggccgcccc tcttcccctc 2460
cctgggcttt tgcttttact ggtttgattt cactggagcc tgctgggaac gtgacctctg 2520
acccctgatg ctttcgtgat cacgtgacca tcctcttccc caacatgtcc tcttcccaaa 2580
actgtgcctg tccccagctt ctggggaggg acacagcttc cccttcccag gaattgagtg 2640
ggcctagccc ctccccccctt ttctccattt gagaggagag tgcttggggc ttgaacccct 2700
taccccactg ctgctgactg ggcagggccc tggacccctt tatttgcacg tcaggggagc 2760
cggctccccc cttgaatgta ccagaccctg ggggggggtca ctgggcccta gatttttggg 2820
gggtcaccag ccactccagg ggcagggacc atttcttcat tttctgaaag cactttaatg 2880
attccccttc ccccaaactc cagggaatgg aggggggacc ccgccagcca aaacattccc 2940
cccattcccg acccccatct cctcttctag cccatgccct tccccggcgg agggagggag 3000
cagggagccc tcactctcca cgccccttgc ttgcatctgt atatagtgtg agcagcaagt 3060
aacccttctc ctccctcccc cctcacccct cctcaatgta gtggccttgg atatcctgtt 3120
tgttaataaa gacaattcaa ccagctccca cc 3152

<210> SEQ ID NO 25
<211> LENGTH: 4878
<212> TYPE: DNA
<213> ORGANISM: Homo sapiens

<400> SEQUENCE: 25
ggctggctcc ggggagatag cgcctgtcag tcggtgggtc ggtcctcgcg ccggccctcc 60
ccctccccgg tctccggggg aggcgcggtg gagtccgccc ccggggttct ccgatggggg 120
agaagcggcg acggcggcag tggagtaacc gagccggagc gtgagcggcc ccggtgcccc 180
gttccccacg gaggccatgg gcgacccagc ccccgcccgc agcctggacg acatcgacct 240
gtccgccctg cgggaccctg ctgggatctt tgagcttgtg gaggtggtcg gcaatggaac 300
ctacggacag gtgtacaagg gtcggcatgt caagacgggg cagctggctg ccatcaaggt 360
catggatgtc acggaggacg aggaggaaga gatcaaacag gagatcaaca tgctgaaaaa 420
gtactctcac caccgcaaca tcgccaccta ctacggagcc ttcatcaaga agagcccccc 480
gggaaacgat gaccagctct ggctggtgat ggagttctgt ggtgctggtt cagtgactga 540

-continued

```
cctggtaaag aacacaaaag gcaacgccct gaaggaggac tgtatcgcct atatctgcag    600
ggagatcctc aggggtctgg cccatctcca tgcccacaag gtgatccatc gagacatcaa    660
ggggcagaat gtgctgctga cagagaatgc tgaggtcaag ctagtggatt ttggggtgag    720
tgctcagctg gaccgcaccg tgggcagacg gaacactttc attgggactc cctactggat    780
ggctccagag gtcatcgcct gtgatgagaa ccctgatgcc acctatgatt acaggagtga    840
tatttggtct ctaggaatca cagccatcga gatggcagag ggagcccccc ctctgtgtga    900
catgcacccc atgcgagccc tcttcctcat tcctcggaac cctccgccca ggctcaagtc    960
caagaagtgg tctaagaagt tcattgactt cattgacaca tgtctcatca agacttacct   1020
gagccgccca cccacggagc agctactgaa gtttcccttc atccgggacc agcccacgga   1080
gcggcaggtc cgcatccagc ttaaggacca cattgaccga tcccggaaga agcggggtga   1140
gaaagaggag acagaatatg agtacagcgg cagcgaggag gaagatgaca gccatggaga   1200
ggaaggagag ccaagctcca tcatgaacgt gcctggagag tcgactctac gccgggagtt   1260
tctccggctc cagcaggaaa ataagagcaa ctcagaggct ttaaaacagc agcagcagct   1320
gcagcagcag cagcagcgag accccgaggc acacatcaaa cacctgctgc accagcggca   1380
gcggcgcata gaggagcaga aggaggagcg gcgccgcgtg gaggagcaac agcggcggga   1440
gcgggagcag cggaagctgc aggagaagga gcagcagcgg cggctggagg acatgcaggc   1500
tctgcggcgg gaggaggagc ggcggcaggc ggagcgcgag caggaataca agcggaagca   1560
gctggaggag cagcggcagt cagaacgtct ccagaggcag ctgcagcagg agcatgccta   1620
cctcaagtcc ctgcagcagc agcaacagca gcagcagctt cagaaacagc agcagcagca   1680
gctcctgcct ggggacagga agcccctgta ccattatggt cggggcatga atcccgctga   1740
caaaccagcc tgggcccgag aggtagaaga gagaacaagg atgaacaagc agcagaactc   1800
tcccttggcc aagagcaagc caggcagcac ggggcctgag ccccccatcc cccaggcctc   1860
cccagggccc ccaggaccc tttcccagac tcctcctatg cagaggccgg tggagcccca   1920
ggagggaccg cacaagagcc tggtggcaca ccgggtccca ctgaagccat atgcagcacc   1980
tgtaccccga tcccagtccc tgcaggacca gcccacccga aacctggctg ccttcccagc   2040
ctcccatgac cccgaccctg ccatccccgc acccactgcc acgcccagtg cccgaggagc   2100
tgtcatccgc cagaattcag accccacctc tgaaggacct ggccccagcc cgaatccccc   2160
agcctgggtc cgcccagata acgaggcccc acccaaggtg cctcagagga cctcatctat   2220
cgccactgcc cttaacacca gtggggccgg agggtcccgg ccagcccagg cagtccgtgc   2280
cagtaacccc gacctcagga ggagcgaccc tggctgggaa cgctcggaca gcgtccttcc   2340
agcctctcac gggcacctcc cccaggctgg ctcactggag cggaaccgcg tgggagtctc   2400
ctccaaaccg gacagctccc ctgtgctctc ccctgggaat aaagccaagc ccgacgacca   2460
ccgctcacgg ccaggccggc ccgcagactt tgtgttgctg aaagagcgga ctctggacga   2520
ggcccctcgg cctcccaaga aggccatgga ctactcgtcg tccagcgagg aggtggaaag   2580
cagtgaggac gacgaggagg aaggcgaagg cgggccagca gaggggagca gagataccc   2640
tgggggccgc agcgatgggg atacagacag cgtcagcacc atggtggtcc acgacgtcga   2700
ggagatcacc gggacccagc cccatacgg gggcggcacc atggtggtcc agcgcacccc   2760
tgaagaggag cggaacctgc tgcatgctga cagcaatggg tacacaaacc tgcctgacgt   2820
ggtccagccc agccactcac ccaccgagaa cagcaaaggc caaagcccac cctcgaagga   2880
tgggagtggt gactaccagt ctcgtgggct ggtaaaggcc cctggcaaga gctcgttcac   2940
```

gatgtttgtg gatctaggga tctaccagcc tggaggcagt ggggacagca tccccatcac 3000
agccctagtg ggtggagagg gcactcggct cgaccagctg cagtacgacg tgaggaaggg 3060
ttctgtggtc aacgtgaatc ccaccaacac ccgggcccac agtgagaccc ctgagatccg 3120
gaagtacaag aagcgattca actccgagat cctctgtgca gccctttggg gggtcaacct 3180
gctggtgggc acggagaacg ggctgatgtt gctggaccga agtgggcagg gcaaggtgta 3240
tggactcatt gggcggcgac gcttccagca gatggatgtg ctggaggggc tcaacctgct 3300
catcaccatc tcagggaaaa ggaacaaact gcgggtgtat tacctgtcct ggctccggaa 3360
caagattctg cacaatgacc cagaagtgga gaagaagcag ggctggacca ccgtgggga 3420 catggagggc tgcgggcact accgtgttgt gaaatacgag cggattaagt tcctggtcat 3480
cgccctcaag agctccgtgg aggtgtatgc ctgggccccc aaaccctacc acaaattcat 3540
ggccttcaag tcctttgccg acctccccca ccgccctctg ctggtcgacc tgacagtaga 3600
ggaggggcag cggctcaagg tcatctatgg ctccagtgct ggcttccatg ctgtggatgt 3660
cgactcgggg aacagctatg acatctacat ccctgtgcac atccagagcc agatcacgcc 3720
ccatgccatc atcttcctcc ccaacaccga cggcatggag atgctgctgt gctacgagga 3780
cgagggtgtc tacgtcaaca cgtacgggcg catcattaag gatgtggtgc tgcagtgggg 3840
ggagatgcct acttctgtgg cctacatctg ctccaaccag ataatgggct ggggtgagaa 3900
agccattgag atccgctctg tggagacggg ccacctcgac ggggtcttca tgcacaaacg 3960
agctcagagg ctcaagttcc tgtgtgagcg gaatgacaag gtgttttttg cctcagtccg 4020
ctctgggggc agcagccaag tttacttcat gactctgaac cgtaactgca tcatgaactg 4080
gtgacggggc cctgggctgg ggctgtccca cactggaccc agctctcccc ctgcagccag 4140
gcttcccggg ccgcccctct ttcccctccc tgggcttttg cttttactgg tttgatttca 4200
ctggagcctg ctgggaacgt gacctctgac ccctgatgct ttcgtgatca cgtgaccatc 4260
ctcttcccca acatgtcctc ttcccaaaac tgtgcctgtc cccagcttct ggggagggac 4320
acagcttccc cttcccagga attgagtggg cctagcccct ccccccttt ctccatttga 4380 gaggagagtg cttggggctt gaacccctta ccccactgct gctgactggg cagggccctg 4440 gacccctta tttgcacgtc aggggagccg gctcccccct tgaatgtacc agaccctggg 4500
gggggtcact gggccctaga tttttggggg gtcaccagcc actccagggg cagggaccat 4560
ttcttcattt tctgaaagca ctttaatgat tccccttccc ccaaactcca gggaatggag 4620
gggggacccc gccagccaaa acattccccc cattcccgac ccccatctcc tcttctagcc 4680
catgcccttc cccggtggag ggagggagca gggagccctc actctccacg cccccttgctt 4740 gcatctgtat atagtgtgag cagcaagtaa cccttctcct ccctccccccc tcacccctcc 4800 tcaatgtagt ggccttggat atcctgtttg ttaataaaga caattcaacc agctcccacc 4860
aaaaaaaaaa aaaaaaaa 4878

<210> SEQ ID NO 26
<211> LENGTH: 4989
<212> TYPE: DNA
<213> ORGANISM: Homo sapiens

<400> SEQUENCE: 26
ggctggctcc ggggagatag cgcctgtcag tcggtgggtc ggtcctcgcg ccggccctcc 60
ccctccccgg tctccggggg aggcgcggtg gagtccgccc ccggggttct ccgatggggg 120
agaagcggcg acggcggcag tggagtaacc gagccggagc gtgagcggcc ccggtgcccc 180

-continued

```
gttccccacg gaggccatgg gcgacccagc ccccgcccgc agcctggacg acatcgacct    240
gtccgccctg cgggaccctg ctgggatctt tgagcttgtg gaggtggtcg gcaatggaac    300
ctacggacag gtgtacaagg gtcggcatgt caagacgggg cagctggctg ccatcaaggt    360
catggatgtc acggaggacg aggaggaaga gatcaaacag gagatcaaca tgctgaaaaa    420
gtactctcac caccgcaaca tcgccaccta ctacggagcc ttcatcaaga agagcccccc    480
gggaaacgat gaccagctct ggctggtgat ggagttctgt ggtgctggtt cagtgactga    540
cctggtaaag aacacaaaag gcaacgccct gaaggaggac tgtatcgcct atatctgcag    600
ggagatcctc aggggtctgg cccatctcca tgcccacaag gtgatccatc gagacatcaa    660
ggggcagaat gtgctgctga cagagaatgc tgaggtcaag ctagtggatt ttggggtgag    720
tgctcagctg gaccgcaccg tgggcagacg gaacactttc attgggactc cctactggat    780
ggctccagag gtcatcgcct gtgatgagaa ccctgatgcc acctatgatt acaggagtga    840
tatttggtct ctaggaatca cagccatcga gatggcagag ggagcccccc ctctgtgtga    900
catgcacccc atgcgagccc tcttcctcat tcctcggaac cctccgccca ggctcaagtc    960
caagaagtgg tctaagaagt tcattgactt cattgacaca tgtctcatca agacttacct   1020
gagccgccca cccacggagc agctactgaa gtttcccttc atccgggacc agcccacgga   1080
gcggcaggtc cgcatccagc ttaaggacca cattgaccga tcccggaaga agcggggtga   1140
gaaagaggag acagaatatg agtacagcgg cagcgaggag gaagatgaca gccatggaga   1200
ggaaggagag ccaagctcca tcatgaacgt gcctggagag tcgactctac gccgggagtt   1260
tctccggctc cagcaggaaa ataagagcaa ctcagaggct ttaaaacagc agcagcagct   1320
gcagcagcag cagcagcgag accccgaggc acacatcaaa cacctgctgc accagcggca   1380
gcggcgcata gaggagcaga aggaggagcg gcgccgcgtg gaggagcaac agcggcggga   1440
gcgggagcag cggaagctgc aggagaagga gcagcagcgg cggctggagg acatgcaggc   1500
tctgcggcgg gaggaggagc ggcggcaggc ggagcgcgag caggaataca agcggaagca   1560
gctggaggag cagcggcagt cagaacgtct ccagaggcag ctgcagcagg agcatgccta   1620
cctcaagtcc ctgcagcagc agcaacagca gcagcagctt cagaaacagc agcagcagca   1680
gctcctgcct ggggacagga agcccctgta ccattatggt cggggcatga atcccgctga   1740
caaaccagcc tgggcccgag aggtagaaga gagaacaagg atgaacaagc agcagaactc   1800
tcccttggcc aagagcaagc caggcagcac ggggcctgag ccccccatcc cccaggcctc   1860
cccagggccc ccaggacccc tttcccagac tcctcctatg cagaggccgg tggagcccca   1920
ggagggaccg cacaagagcc tggtggcaca ccgggtccca ctgaagccat atgcagcacc   1980
tgtaccccga tcccagtccc tgcaggacca gcccacccga aacctggctg ccttcccagc   2040
ctcccatgac cccgaccctg ccatccccgc acccactgcc acgcccagtg cccgaggagc   2100
tgtcatccgc cagaattcag accccacctc tgaaggacct ggccccagcc cgaatccccc   2160
agcctgggtc cgcccagata acgaggcccc acccaaggtg cctcagagga cctcatctat   2220
cgccactgcc cttaacacca gtggggccgg agggtcccgg ccagcccagg cagtccgtgc   2280
cagacctcgc agcaactccg cctggcaaat ctatctgcaa aggcgggcag agcggggcac   2340
cccaaagcct ccagggcccc ctgctcagcc ccctggcccg cccaacgcct ctagtaaccc   2400
cgacctcagg aggagcgacc ctggctggga acgctcggac agcgtccttc cagcctctca   2460
cgggcacctc ccccaggctg gctcactgga gcggaaccgc gtgggagtct cctccaaacc   2520
ggacagctcc cctgtgctct cccctgggaa taaagccaag cccgacgacc accgctcacg   2580
```

-continued

```
gccaggccgg cccgcagact ttgtgttgct gaaagagcgg actctggacg aggcccctcg   2640
gcctcccaag aaggccatgg actactcgtc gtccagcgag gaggtggaaa gcagtgagga   2700
cgacgaggag gaaggcgaag gcgggccagc agaggggagc agagataccc ctgggggccg   2760
cagcgatggg gatacagaca gcgtcagcac catggtggtc cacgacgtcg aggagatcac   2820
cgggacccag cccccatacg ggggcggcac catggtggtc cagcgcaccc ctgaagagga   2880
gcggaacctg ctgcatgctg acagcaatgg gtacacaaac ctgcctgacg tggtccagcc   2940
cagccactca cccaccgaga acagcaaagg ccaaagccca ccctcgaagg atgggagtgg   3000
tgactaccag tctcgtgggc tggtaaaggc ccctggcaag agctcgttca cgatgtttgt   3060
ggatctaggg atctaccagc ctggaggcag tggggacagc atccccatca cagccctagt   3120
gggtggagag ggcactcggc tcgaccagct gcagtacgac gtgaggaagg gttctgtggt   3180
caacgtgaat cccaccaaca cccgggccca cagtgagacc cctgagatcc ggaagtacaa   3240
gaagcgattc aactccgaga tcctctgtgc agccctttgg ggggtcaacc tgctggtggg   3300
cacggagaac gggctgatgt tgctggaccg aagtgggcag ggcaaggtgt atggactcat   3360
tgggcggcga cgcttccagc agatggatgt gctggagggg ctcaacctgc tcatcaccat   3420
ctcagggaaa aggaacaaac tgcgggtgta ttacctgtcc tggctccgga acaagattct   3480
gcacaatgac ccagaagtgg agaagaagca gggctggacc accgtggggg acatggaggg   3540
ctgcgggcac taccgtgttg tgaaatacga gcggattaag ttcctggtca tcgccctcaa   3600
gagctccgtg gaggtgtatg cctgggcccc caaaccctac cacaaattca tggccttcaa   3660
gtcctttgcc gacctccccc accgccctct gctggtcgac ctgacagtag aggaggggca   3720
gcggctcaag gtcatctatg gctccagtgc tggcttccat gctgtggatg tcgactcggg   3780
gaacagctat gacatctaca tccctgtgca catccagagc cagatcacgc cccatgccat   3840
catcttcctc cccaacaccg acggcatgga gatgctgctg tgctacgagg acgagggtgt   3900
ctacgtcaac acgtacgggc gcatcattaa ggatgtggtg ctgcagtggg gggagatgcc   3960
tacttctgtg gcctacatct gctccaacca gataatgggc tggggtgaga aagccattga   4020
gatccgctct gtggagacgg gccacctcga cggggtcttc atgcacaaac gagctcagag   4080
gctcaagttc ctgtgtgagc ggaatgacaa ggtgtttttt gcctcagtcc gctctggggg   4140
cagcagccaa gtttacttca tgactctgaa ccgtaactgc atcatgaact ggtgacgggg   4200
ccctgggctg gggctgtccc acactggacc cagctctccc cctgcagcca ggcttcccgg   4260
gccgcccctc tttcccctcc ctgggctttt gcttttactg gtttgatttc actggagcct   4320
gctgggaacg tgacctctga cccctgatgc tttcgtgatc acgtgaccat cctcttcccc   4380
aacatgtcct cttcccaaaa ctgtgcctgt ccccagcttc tggggaggga cacagcttcc   4440
ccttcccagg aattgagtgg gcctagcccc tccccccttt tctccatttg agaggagagt   4500
gcttggggct tgaacccctt accccactgc tgctgactgg gcagggccct ggaccccttt   4560
atttgcacgt caggggagcc ggctcccccc ttgaatgtac cagaccctgg ggggggtcac   4620
tgggccctag atttttgggg ggtcaccagc cactccaggg gcagggacca tttcttcatt   4680
ttctgaaagc actttaatga ttccccttcc cccaaactcc agggaatgga ggggggaccc   4740
cgccagccaa aacattcccc ccattcccga ccccctctc  ctcttctagc ccatgccctt   4800
ccccggtgga gggagggagc agggagccct cactctccac gccccttgct tgcatctgta   4860
tatagtgtga gcagcaagta acccttctcc tccctccccc ctcacccctc ctcaatgtag   4920
tggccttgga tatcctgttt gttaataaag acaattcaac cagctcccac caaaaaaaaa   4980
```

aaaaaaaaa 4989

<210> SEQ ID NO 27
<211> LENGTH: 4902
<212> TYPE: DNA
<213> ORGANISM: Homo sapiens

<400> SEQUENCE: 27
ggctggctcc ggggagatag cgcctgtcag tcggtgggtc ggtcctcgcg ccggccctcc 60
ccctccccgg tctccggggg aggcgcggtg gagtccgccc ccggggttct ccgatggggg 120
agaagcggcg acggcggcag tggagtaacc gagccggagc gtgagcggcc ccggtgcccc 180
gttccccacg gaggccatgg gcgacccagc ccccgcccgc agcctggacg acatcgacct 240
gtccgccctg cgggaccctg ctgggatctt tgagcttgtg gaggtggtcg gcaatggaac 300
ctacggacag gtgtacaagg gtcggcatgt caagacgggg cagctggctg ccatcaaggt 360
catggatgtc acggaggacg aggaggaaga gatcaaacag gagatcaaca tgctgaaaaa 420
gtactctcac caccgcaaca tcgccaccta ctacggagcc ttcatcaaga agagcccccc 480
gggaaacgat gaccagctct ggctggtgat ggagttctgt ggtgctggtt cagtgactga 540
cctggtaaag aacacaaaag gcaacgccct gaaggaggac tgtatcgcct atatctgcag 600
ggagatcctc aggggtctgg cccatctcca tgcccacaag gtgatccatc gagacatcaa 660
ggggcagaat gtgctgctga cagagaatgc tgaggtcaag ctagtggatt ttggggtgag 720
tgctcagctg gaccgcaccg tgggcagacg gaacactttc attgggactc cctactggat 780
ggctccagag gtcatcgcct gtgatgagaa ccctgatgcc acctatgatt acaggagtga 840
tatttggtct ctaggaatca cagccatcga gatggcagag ggagcccccc ctctgtgtga 900
catgcacccc atgcgagccc tcttcctcat tcctcggaac cctccgccca ggctcaagtc 960
caagaagtgg tctaagaagt tcattgactt cattgacaca tgtctcatca agacttacct 1020
gagccgccca cccacggagc agctactgaa gtttcccttc atccgggacc agcccacgga 1080
gcggcaggtc cgcatccagc ttaaggacca cattgaccga tcccggaaga agcggggtga 1140
gaaagaggag acagaatatg agtacagcgg cagcgaggag gaagatgaca gccatggaga 1200
ggaaggagag ccaagctcca tcatgaacgt gcctggagag tcgactctac gccgggagtt 1260
tctccggctc cagcaggaaa ataagagcaa ctcagaggct ttaaaacagc agcagcagct 1320
gcagcagcag cagcagcgag accccgaggc acacatcaaa cacctgctgc accagcggca 1380
gcggcgcata gaggagcaga aggaggagcg gcgccgcgtg gaggagcaac agcggcggga 1440
gcgggagcag cggaagctgc aggagaagga gcagcagcgg cggctggagg acatgcaggc 1500
tctgcggcgg gaggaggagc ggcggcaggc ggagcgcgag caggaataca agcggaagca 1560
gctggaggag cagcggcagt cagaacgtct ccagaggcag ctgcagcagg agcatgccta 1620
cctcaagtcc ctgcagcagc agcaacagca gcagcagctt cagaaacagc agcagcagca 1680
gctcctgcct ggggacagga agcccctgta ccattatggt cggggcatga atcccgctga 1740
caaaccagcc tgggcccgag aggtagaaga gagaacaagg atgaacaagc agcagaactc 1800
tcccttggcc aagagcaagc caggcagcac ggggcctgag ccccccatcc cccaggcctc 1860
cccagggccc ccaggacccc tttcccagac tcctcctatg cagaggccgg tggagcccca 1920
ggagggaccg cacaagagcc tggtggcaca ccgggtccca ctgaagccat atgcagcacc 1980
tgtaccccga tcccagtccc tgcaggacca gcccacccga aacctggctg ccttcccagc 2040
ctcccatgac cccgaccctg ccatccccgc acccactgcc acgcccagtg cccgaggagc 2100

```
tgtcatccgc cagaattcag accccacctc tgaaggacct ggccccagcc cgaatccccc   2160
agcctgggtc cgcccagata acgaggcccc acccaaggtg cctcagagga cctcatctat   2220
cgccactgcc cttaacacca gtggggccgg agggtcccgg ccagcccagg cagtccgtgc   2280
cagtaacccc gacctcagga ggagcgaccc tggctgggaa cgctcggaca gcgtccttcc   2340
agcctctcac gggcacctcc cccaggctgg ctcactggag cggaaccgcg tgggagtctc   2400
ctccaaaccg gacagctccc ctgtgctctc ccctgggaat aaagccaagc ccgacgacca   2460
ccgctcacgg ccaggccggc ccgcaagcta taagcgagca attggtgagg actttgtgtt   2520
gctgaaagag cggactctgg acgaggcccc tcggcctccc aagaaggcca tggactactc   2580
gtcgtccagc gaggaggtgg aaagcagtga ggacgacgag gaggaaggcg aaggcgggcc   2640
agcagagggg agcagagata cccctggggg ccgcagcgat ggggatacag acagcgtcag   2700
caccatggtg gtccacgacg tcgaggagat caccgggacc cagcccccat acgggggcgg   2760
caccatggtg gtccagcgca cccctgaaga ggagcggaac ctgctgcatg ctgacagcaa   2820
tgggtacaca aacctgcctg acgtggtcca gcccagccac tcacccaccg agaacagcaa   2880
aggccaaagc ccaccctcga aggatgggag tggtgactac cagtctcgtg ggctggtaaa   2940
ggcccctggc aagagctcgt tcacgatgtt tgtggatcta gggatctacc agcctggagg   3000
cagtggggac agcatcccca tcacagccct agtgggtgga gagggcactc ggctcgacca   3060
gctgcagtac gacgtgagga agggttctgt ggtcaacgtg aatcccacca acacccgggc   3120
ccacagtgag acccctgaga tccggaagta caagaagcga ttcaactccg agatcctctg   3180
tgcagccctt tggggggtca acctgctggt gggcacggag aacgggctga tgttgctgga   3240
ccgaagtggg cagggcaagg tgtatggact cattgggcgg cgacgcttcc agcagatgga   3300
tgtgctggag gggctcaacc tgctcatcac catctcaggg aaaaggaaca aactgcgggt   3360
gtattacctg tcctggctcc ggaacaagat tctgcacaat gacccagaag tggagaagaa   3420
gcagggctgg accaccgtgg gggacatgga gggctgcggg cactaccgtg ttgtgaaata   3480
cgagcggatt aagttcctgg tcatcgccct caagagctcc gtggaggtgt atgcctgggc   3540
ccccaaaccc taccacaaat tcatggcctt caagtccttt gccgacctcc cccaccgccc   3600
tctgctggtc gacctgacag tagaggaggg gcagcggctc aaggtcatct atggctccag   3660
tgctggcttc catgctgtgg atgtcgactc ggggaacagc tatgacatct acatccctgt   3720
gcacatccag agccagatca cgccccatgc catcatcttc ctccccaaca ccgacggcat   3780
ggagatgctg ctgtgctacg aggacgaggg tgtctacgtc aacacgtacg ggcgcatcat   3840
taaggatgtg gtgctgcagt ggggggagat gcctacttct gtggcctaca tctgctccaa   3900
ccagataatg ggctggggtg agaaagccat tgagatccgc tctgtggaga cgggccacct   3960
cgacggggtc ttcatgcaca aacgagctca gaggctcaag ttcctgtgtg agcggaatga   4020
caaggtgttt tttgcctcag tccgctctgg gggcagcagc caagtttact tcatgactct   4080
gaaccgtaac tgcatcatga actggtgacg gggccctggg ctggggctgt cccacactgg   4140
acccagctct ccccctgcag ccaggcttcc cgggccgccc ctctttcccc tccctgggct   4200
tttgctttta ctggtttgat ttcactggag cctgctggga acgtgacctc tgacccctga   4260
tgctttcgtg atcacgtgac catcctcttc cccaacatgt cctcttccca aaactgtgcc   4320
tgtccccagc ttctggggag ggacacagct tccccttccc aggaattgag tgggcctagc   4380
ccctcccccc ttttctccat ttgagaggag agtgcttggg gcttgaaccc cttaccccac   4440
tgctgctgac tgggcagggc cctggacccc tttatttgca cgtcagggga gccggctccc   4500
```

cccttgaatg taccagaccc tgggggggt cactgggccc tagatttttg gggggtcacc 4560
agccactcca ggggcaggga ccatttcttc attttctgaa agcactttaa tgattcccct 4620
tcccccaaac tccagggaat ggagggggga ccccgccagc caaaacattc cccccattcc 4680
cgacccccct ctcctcttct agcccatgcc cttccccggt ggagggaggg agcagggagc 4740
cctcactctc cacgcccctt gcttgcatct gtatatagtg tgagcagcaa gtaacccttc 4800
tcctccctcc cccctcaccc ctcctcaatg tagtggcctt ggatatcctg tttgttaata 4860
aagacaattc aaccagctcc caccaaaaaa aaaaaaaaaa aa 4902

<210> SEQ ID NO 28
<211> LENGTH: 4737
<212> TYPE: DNA
<213> ORGANISM: Homo sapiens

<400> SEQUENCE: 28
atggcgggac ctgggggctg gagggacagg gaggtcacgg atctgggcca cctgccggat 60
ccaactggaa tattctcact agataaaacc attggccttg gtacttatgg cagaatctat 120
ttgggacttc atgagaagac tggtgcattt acagctgtta aagtgatgaa cgctcgtaag 180 accccttac ctgaaatagg aaggcgagtg agagtgaata aatatcaaaa atctgttggg 240
tggagataca gtgatgagga agaggatctc aggactgaac tcaaccttct gaggaagtac 300
tctttccaca aaaacattgt gtccttctat ggagcatttt tcaagctgag tccccctggt 360
cagcggcacc aactttggat ggtgatggag ttatgtgcag caggttcggt cactgatgta 420
gtgagaatga ccagtaatca gagtttaaaa gaagattgga ttgcttatat ctgccgagaa 480
atccttcagg gcttagctca ccttcacgca caccgagtaa ttcaccggga catcaaaggt 540
cagaatgtgc tgctgactca taatgctgaa gtaaaactgg ttgattttgg agtgagtgcc 600
caggtgagca gaactaatgg aagaaggaat agtttcattg ggacaccata ctggatggca 660
cctgaggtga ttgactgtga tgaggaccca agacgctcct atgattacag aagtgatgtg 720
tggtctgtgg gaattactgc cattgaaatg gctgaaggag cccctctgtg taaccttcaa 780
cccttggaag ctctcttcgt tattttgcgg gaatctgctc ccacagtcaa atccagcgga 840
tggtcccgta agttccacaa tttcatggaa aagtgtacga taaaaaattt cctgtttcgt 900
cctacttctg caaacatgct tcaacaccca tttgttcggg atataaaaaa tgaacgacat 960
gttgttgagt cattaacaag gcatcttact ggaatcatta aaaaaagaca gaaaaaagga 1020 ataccttga tctttgaaag agaagaagct attaaggaac agtacaccgt gagaagattt 1080
agaggaccct cttgcactca cgagcttctg agattgccaa ccagcagcag atgcagacca 1140
cttagagtcc tgcatgggga accctctcag ccaaggtggc tacctgatcg agaagagcca 1200
caggtccagg cacttcagca gctacaggga gcagccaggg tattcatgcc actgcaggct 1260
ctggacagtg cacctaagcc tctaaagggg caggctcagg cacctcaacg actacaaggg 1320
gcagctcggg tgttcatgcc actacaggct caggtgaagg ctaaagcctc taaacctcta 1380
caaatgcaga ttaaggcacc tccacgacta cggagggcag ccagggtgct catgccacta 1440
caggcacagg ttagggcacc taggcttctg caggtacagt cccaggtatc caaaaagcag 1500
caggcccaga cccagacatc agaaccacaa gatttggacc aggtaccaga ggaatttcag 1560
ggtcaagatc aggtacccga acaacaaagg cagggccagg cccctgaaca acagcagagg 1620
cacaaccagg tgcctgaaca agagctggag cagaaccagg cacctgaaca gccagaggta 1680
caggaacagg ctgccgagcc tgcacaggca gagactgagg cagaggaacc tgagtcatta 1740

```
cgagtaaatg cccaggtatt tctgcccctg ctatcacaag atcaccatgt gctgttgcca   1800
ctacatttgg atactcaggt gctcattcca gtagaggggc aaactgaagg atcacctcag   1860
gcacaggctt ggacactaga acccccacag gcaattggct cagttcaagc actgatagag   1920
ggactatcaa gagacttgct tcgggcacca aactcaaata actcaaagcc acttggtccg   1980
ttgcaaaccc tgatggaaaa tctgtcatca aataggtttt actcacaacc agaacaggca   2040
cgggagaaaa aatcaaaagt ttctactctg aggcaagcac tggcaaaaag actatcacca   2100
aagaggttca gggcaaagtc atcatggaga cctgaaaagc ttgaactctc ggatttagaa   2160
gcccgcaggc aaaggcgcca acgcagatgg gaagatatct ttaatcagca tgaggaagaa   2220
ttgagacaag ttgataagga caaagaagat gaatcatcag acaatgatga agtatttcat   2280
tcgattcagg ctgaagtcca gatagagcca ttgaagccat acatttcaaa tcctaaaaaa   2340
attgaggttc aagagagatc tccttctgtg cctaacaacc aggatcatgc acatcatgtc   2400
aagttctctt caagcgttcc tcagcggtct cttttggaac aagctcagaa gcccattgac   2460
atcagacaaa ggagttcgca aaatcgtcaa aattggctgg cagcatcaga atcttcttct   2520
gaggaagaaa gtcctgtgac tggaaggagg tctcagtcat caccacctta ttctactatt   2580
gatcagaagt tgctggttga catccatgtt ccagatggat ttaaagtagg aaaaatatca   2640
ccccctgtat acttgacaaa cgaatgggta ggctataatg cactctctga aatcttccgg   2700
aatgattggt taactccggc acctgtcatt cagccacctg aagaggatgg tgattatgtt   2760
gaactctatg atgccagtgc tgatactgat ggtgatgatg atgatgagtc taatgatact   2820
tttgaagata cctatgatca tgccaatggc aatgatgact tggataacca ggttgatcag   2880
gctaatgatg tttgtaaaga ccatgatgat gacaacaata agtttgttga tgatgtaaat   2940
aataattatt atgaggcgcc tagttgtcca agggcaagct atggcagaga tggaagctgc   3000
aagcaagatg gttatgatgg aagtcgtgga aaagaggaag cctacagagg ctatggaagc   3060
catacagcca atagaagcca tggaggaagt gcagccagtg aggacaatgc agccattgga   3120
gatcaggaag aacatgcagc caatataggc agtgaaagaa gaggcagtga gggtgatgga   3180
ggtaagggag tcgttcgaac cagtgaagag agtggagccc ttggactcaa tggagaagaa   3240
aattgctcag agacagatgg tccaggattg aagagacctg cgtctcagga ctttgaatat   3300
ctacaggagg agccaggtgg tggaaatgag gcctcaaatg ccattgactc aggtgctgca   3360
ccgtcagcac ctgatcatga gagtgacaat aaggacatat cagaatcatc aacacaatca   3420
gatttttctg ccaatcactc atctccttcc aaaggttctg ggatgtctgc tgatgctaac   3480
tttgccagtg ccatctacgc tggattcgta gaagtacctg aggaatcacc taagcaaccc   3540
tctgaagtca atgttaaccc actctatgtc tctcctgcat gtaaaaaacc actaatccac   3600
atgtatgaaa aggagttcac ttctgagatc tgctgtggtt ctttgtgggg agtcaatttg   3660
ctgttgggaa cccgatctaa tctatatctg atggacagaa gtggaaaggc tgacattact   3720
aaacttataa ggcgaagacc attccgccag attcaagtct tagagccact caatttgctg   3780
attaccatct caggtcataa gaacagactt cgggtgtatc atctgacctg gttgaggaac   3840
aagattttga ataatgatcc agaaagtaaa agaaggcaag aagaaatgct gaagacagag   3900
gaagcctgca aagctattga taagttaaca ggctgtgaac acttcagtgt ccaacatgaa   3960
gaaacaacat atattgcaat tgctttgaaa tcatcaattc acctttatgc atgggcacca   4020
aagtcctttg atgaaagcac tgctattaaa gtatgcattg atcaatcagc agactctgaa   4080
ggagactaca tgtcctatca agcctatata cgaatactgg caaaaataca ggcagctgat   4140
```

-continued

```
ccagtgaacc ggtttaagag accagatgag ctccttcatt tgctgaagct caaggtattt   4200

ccaacacttg atcataagcc agtgacagtt gacctggcta ttggttctga aaaaagacta   4260

aagattttct tcagctcagc agatggatat cacctcatcg atgcagaatc tgaggttatg   4320

tctgatgtga ccctgccaaa gaatcccctg gaaatcatta taccacagaa tatcatcatt   4380

ttacctgatt gcttgggaat tggcatgatg ctcaccttca atgctgaagc cctctctgtg   4440

gaagcaaatg aacaactctt caagaagatc cttgaaatgt ggaaagacat accatcttct   4500

atagcttttg aatgtacaca gcgaaccaca ggatggggcc aaaaggccat tgaagtgcgc   4560

tctttgcaat ccagggttct ggaaagtgag ctgaagcgca ggtcaattaa gaagctgaga   4620

ttcctgtgca cccggggtga caagctgttc tttacctcta ccctgcgcaa tcaccacagc   4680

cgggtttact tcatgacact tggaaaactt gaagagctcc aaagcaatta tgatgtc      4737
```

<210> SEQ ID NO 29
<211> LENGTH: 942
<212> TYPE: DNA
<213> ORGANISM: Homo sapiens

<400> SEQUENCE: 29

```
aatcatcaat tcacctttat gcatgggcac caaagtcctt tgatgaaagc actgctatta     60

aagtatttcc aacacttgat cataagccag tgacagttga cctggctatt ggttctgaaa    120

aaagactaaa gattttcttc agctcagcag atggatatca cctcatcgat gcagaatctg    180

aggttatgtc tgatgtgacc ctgccaaaga atcccctgga aatcattata ccacagaata    240

tcatcatttt acctgattgc ttgggaattg gcatgatgct caccttcaat gctgaagccc    300

tctctgtgga agcaaatgaa caactcttca agaagatcct tgaaatgtgg aaagacatac    360

catcttctat agcttttgaa tgtacacagc gaaccacagg atggggccaa aaggccattg    420

aagtgcgctc tttgcaatcc agggttctgg aaagtgagct gaagcgcagg tcaattaaga    480

agctgagatt cctgtgcacc cggggtgaca agctgttctt tacctctacc ctgcgcaatc    540

accacagccg ggtttacttc atgacacttg gaaaacttga agagctccaa agcaattatg    600

atgtctaaaa gtttccagtg atttattacc acattataaa catcatgtat aggcagtctg    660

catcttcaga tttcagagat taaatgagta ttcagtttta tttttagtaa agattaaatc    720

caaaacttta cttttaatgt agcacagaat agttttaatg agaaatgcag ctttatgtat    780

aaaattaact atagcaagct ctaggtactc caatggtgta caatgtcttt tgcacaaact    840

ttgtaacttt tgttactgtg aattcaaaca ttactctttg gacagtttgg acagtatctg    900

tattcagatt ttacaacatg gagtaaagaa acctgttatg aa                       942
```

<210> SEQ ID NO 30
<211> LENGTH: 513
<212> TYPE: DNA
<213> ORGANISM: Homo sapiens
<220> FEATURE:
<221> NAME/KEY: misc_feature
<222> LOCATION: (507)..(507)
<223> OTHER INFORMATION: n is a, c, g, or t

<400> SEQUENCE: 30

```
ccttctagct tcttcgtctc caggactgac gctcaggctc ctctctcgcc ttagcccaac     60

ttgctttccc gcctcgcaaa ctccggtttc cctccactcc caactctttt cactacacgt    120

ttcccctcct ctatctccca cgccacgaac cccgatcccc agactcctct ctcccgccct    180

cctccttcct ctctcctccc ttcaactctt catccgcttc cacctcagac tctgcgcgca    240
```

-continued

```
cccaattcag tcgcccgctc ccgttcggct cctcgaagcc atggcgggac ctgggggctg    300

gagggacagg gaggtcacgg atctgggcca cctgccggat ccaactggaa tattctcact    360

agataaaacc attggcatgg tacttatggc agaatctatt tgggacttca tgagaagact    420

ggtgcattta cagctgttaa agtgatgaac gctcgtaaga cccctttacc tgaaatagga    480

aggcgagtga gagtgaataa atatcanaaa tct                                 513
```

<210> SEQ ID NO 31
<211> LENGTH: 8082
<212> TYPE: DNA
<213> ORGANISM: Homo sapiens

<400> SEQUENCE: 31

```
ggacagcgct ctcgacacgg agcacccttc tagcttcttc gtctccagga ctgacgctca     60

ggctcctctc tcgccttagc ccaacttgct ttcccgcctc gcaaactccg gtttccctcc    120

actcccaact cttttcacta cacgtttccc ctcctctatc tcccacgcca cgaaccccga    180

tccccagact cctctctccc gccctcctcc ttcctctctc ctcccttcaa ctcttcatcc    240

gcttccacct cagactctgc gcgcacccaa ttcagtcgcc cgctcccgtt cggctcctcg    300

aagccatggc gggacctggg ggctggaggg acagggaggt cacggatctg ggccacctgc    360

cggatccaac tggaatattc tcactagata aaaccattgg ccttggtact tatggcagaa    420

tctatttggg acttcatgag aagactggtg catttacagc tgttaaagtg atgaacgctc    480

gtaagacccc tttacctgaa ataggaaggc gagtgagagt gaataaatat caaaaatctg    540

ttgggtggag atacagtgat gaggaagagg atctcaggac tgaactcaac cttctgagga    600

agtactcttt ccacaaaaac attgtgtcct tctatggagc atttttcaag ctgagtcccc    660

ctggtcagcg gcaccaactt tggatggtga tggagttatg tgcagcaggt tcggtcactg    720

atgtagtgag aatgaccagt aatcagagtt taaaagaagg ttggattgct tatatctgcc    780

gagaaatcct tcagggctta gctcaccttc acgcacaccg agtaattcac cgggacatca    840

aaggtcagaa tgtgctgctg actcataatg ctgaagtaaa actggttgat tttggagtga    900

gtgcccaggt gagcagaact aatggaagaa ggaatagttt cattgggaca ccatactgga    960

tggcacctga ggtgattgac tgtgatgagg acccaagacg ctcctatgat tacagaagtg   1020

atgtgtggtc tgtgggaatt actgccattg aaatggctga aggagcccct cctctgtgta   1080

accttcaacc cttggaagct ctcttcgtta ttttgcggga atctgctccc acagtcaaat   1140

ccagcggatg gtcccgtaag ttccacaatt tcatggaaaa gtgtacgata aaaaatttcc   1200

tgtttcgtcc tacttctgca aacatgcttc aacacccatt tgttcgggat ataaaaaatg   1260

aacgacatgt tgttgagtca ttaacaaggc atcttactgg aatcattaaa aaaagacaga   1320

aaaaaggaat acctttgatc tttgaaagag aagaagctat taaggaacag tacaccgtga   1380

gaagattcag aggaccctct tgcactcacg agcttctgag attgccaacc agcagcagat   1440

gcagaccact tagagtcctg catggggaac cctctcagcc aaggtggcta cctgatcgag   1500

aagagccaca ggtccaggca cttcagcagc tacagggagc agccagggta ttcatgccac   1560

tgcaggctct ggacagtgca cctaagcctc taaaggggca ggctcaggca cctcaacgac   1620

tacaaggggc agctcgggtg ttcatgccac tacaggctca ggtgaaggct aaggcctcta   1680

aacctctaca aatgcagatt aaggcacctc cacgactacg gagggcagcc agggtgctca   1740

tgccactaca ggcacaggtt agggcaccta ggcttctgca ggtacagtcc caggtatcca   1800

aaaagcagca ggcccagacc cagacatcag aaccacaaga tttggaccag gtaccagagg   1860
```

-continued

```
aatttcagag tcaagatcag gtacccgaac aacaaaggca gggccaggcc cctgaacaac   1920
agcagaggca caaccaggtg cctgaacaag agctggagca gaaccaggca cctgaacagc   1980
cagaggtaca ggaacaggct gccgagcctg cacaggcagg gactgaggca gaggaacctg   2040
agtcattacg agtaaatgcc caggtatttc tgcccctgct atcacaagat caccatgtgc   2100
tgttgccact acatttggat actcaggtgc tcattccagt agaggggcaa actgaaggat   2160
cacctcaggc acaggcttgg acactagagc cccacaggc aattggctca gttcaagcac    2220
tgatagaggg actatcaaga gacttgcttc gggcgccaaa ctcaaataac tcaaagccac   2280
ttggtccgtt gcaaaccctg atggaaaatc tgtcatcaaa taggttttac tcacaaccag   2340
aacaggcacg ggagaaaaaa tcaaaagttt ctactctgag gcaagcactg gcaaaaagac   2400
tatcaccaaa gaggttcggg gcaaagtcat catggagacc tgaaaagctt gaactctcgg   2460
atttagaagc ccgcaggcaa aggcgccaac gcagatggga agatatcttt aatcagcatg   2520
aggaagaatt gagacaagtt gataaagaca aagaagatga atcatcagac aatgatgaag   2580
tatttcattc gattcaggct gaagtccaga tagagccatt gaagccatac atttcaaatc   2640
ctaaaaaaat tgaggttcaa gagagatctc cttctgtgcc taacaaccag gatcatgcac   2700
atcatgtcaa gttctcttca agcgttcctc agcggtctct tttggaacaa gctcagaagc   2760
ccattgacat cagacaaagg agttcgcaaa atcgtcaaaa ttggctggca gcatcagaat   2820
cttcttctga ggaagaaagt cctgtgactg gaaggaggtc tcagtcatca ccaccttatt   2880
ctactattga tcagaagttg ctggttgaca tccatgttcc agatggattt aaagtaggaa   2940
aaatatcacc ccctgtatac ttgacaaacg aatgggtagg ctataatgca ctctctgaaa   3000
tcttccggaa tgattggtta actccggcac ctgtcattca gccacctgaa gaggatggtg   3060
attatgttga actctatgat gccagtgctg atactgatgg tgatgatgat gatgagtcta   3120
atgatacttt tgaagatacc tatgatcatg ccaatggcaa tgatgacttg gataaccagg   3180
ttgatcaggc taatgatgtt tgtaaagacc atgatgatga caacaataag tttgttgatg   3240
atgtaaataa taattattat gaggcgccta gttgtccaag ggcaagctat ggcagagatg   3300
gaagctgcaa gcaagatggt tatgatggaa gtcgtggaaa agaggaagcc tacagaggct   3360
atggaagcca tacagccaat agaagccatg gaggaagtgc agccagtgag gacaatgcag   3420
ccattggaga tcaggaagaa catgcagcca atataggcag tgaaagaaga ggcagtgagg   3480
gtgatggagg taagggagtc gttcgaacca gtgaagagag tggagccctt ggactcaatg   3540
gagaagaaaa ttgctcagag acagatggtc caggattgaa gagacctgcg tctcaggact   3600
ttgaatatct acaggaggag ccaggtggtg gaaatgaggc ctcaaatgcc attgactcag   3660
gtgctgcacc gtcagcacct gatcatgaga gtgacaataa ggacatatca gaatcaccaa   3720
cacaatcaga tttttctgcc aatcactcat ctccttccaa aggttctggg atgtctgctg   3780
atgctaactt tgccagtgcc atcttatacg ctggattcgt agaagtacct gaggaatcac   3840
ctaagcaacc ctctgaagtc aatgttaacc cactctatgt ctctcctgca tgtaaaaaac   3900
cactaatcca catgtatgaa aaggagttca cttctgagat ctgctgcggt tctttgtggg   3960
gagtcaattt gctgttggga acccgatcta atctatatct gatggacaga agtggaaagg   4020
ctgacattac taaacttata aggcgaagac cattccgcca gattcaagtc ttagagccac   4080
tcaatttgct gattaccatc tcaggtcata agaacagact tcgggtgtat catctgacct   4140
ggttgaggaa caagattttg aataatgatc cagaaagtaa aagaaggcaa gaagaaatgc   4200
tgaagacaga ggaagcctgc aaagctattg ataagttaac aggctgtgaa cacttcagtg   4260
```

-continued

```
tcctccaaca tgaagaaaca acatatattg caattgcttt gaaatcatca attcaccttt   4320
atgcatgggc accaaagtcc tttgatgaaa gcactgctat taaagtatgc attgatcaat   4380
cagcagactc tgaaggagac tacatgtcct atcaagccta tatacgaata ctggcaaaaa   4440
tacaggcagc tgatccagtg aaccggttta agagaccaga tgagctcctt catttgctga   4500
agctcaaggt atttccaaca cttgatcata agccagtgac agttgacctg gctattggtt   4560
ctgaaaaaag actaaagatt ttcttcagct cagcagatgg atatcacctc atcgatgcag   4620
aatctgaggt tatgtctgat gtgaccctgc caaagaatcc cctggaaatc attataccac   4680
agaatatcat cattttacct gattgcttgg gaattggcat gatgctcacc ttcaatgctg   4740
aagccctctc tgtggaagca aatgaacaac tcttcaagaa gatccttgaa atgtggaaag   4800
acataccatc ttctatagct tttgaatgta cacagcgaac cacaggatgg ggccaaaagg   4860
ccattgaagt gcgctctttg caatccaggg ttctggaaag tgagctgaag cgcaggtcaa   4920
ttaagaagct gagattcctg tgcacccggg gtgacaagct gttctttacc tctaccctgc   4980
gcaatcacca cagccgggtt tacttcatga cacttggaaa acttgaagag ctccaaagca   5040
attatgatgt ctaaaagttt ccagtgattt attaccacat tataaacatc atgtataggc   5100
agtctgcatc ttcagatttc agagattaaa tgagtattca gttttatttt tagtaaagat   5160
taaatccaaa actttacttt taatgtagca cagaatagtt ttaatgagaa atgcagcttt   5220
atgtataaaa ttaactatag caagctctag gtactccaat ggtgtacaat gtcttttgca   5280
caaactttgt aacttttgtt actgtgaatt caaacattac tctttggaca gtttggacag   5340
tatctgtatt cagattttac aacatggagt aaagaaacct gttatgaatt agattacaag   5400
cagccttcaa aagaattggc actgggataa gatttttcag aaaaagaaaa acatcggcaa   5460
actgtgtgtg attttttccaa agctatataa agaaccaaag gtttagtcaa gaaacaaaaa   5520
tcttaaagat tattataacc cagactaagg ttgaacaacc tgcatgccca gagaaaacta   5580
tggcgacaaa ggggaaaagg ccaccactcg ttttctcact gattcatgcc aattaagcct   5640
acagttaaag accagtttgg ttcttttcac ccatttttaa gctggttttc tcctgataag   5700
aagaaaggaa gaaagcccca gacgcttggt ttttctcaga acccccaaaa gatgtgcaat   5760
agctgttgtt acaaaccacc aaataataca gttgtgagcc tgaatacagg actgaactcc   5820
tatacacgtg tactgtagaa tgagtatttt ttaatacctt aaggtaggcg tcaaattcta   5880
ctccccaaag cagagatgga ttgatttatc aaaattatta tctggccaac agtgtgacta   5940
tcagacagca tcaaatattt gcccaatcca agattagact acacaaaagc ttccttccag   6000
tattaaacaa aaagaattaa acataactat gaaaaaactt tgctaatatc tgtgtttttc   6060
agatttcatt ttttgtaaaa tcagaaatta atctaaacat attcagtgat aagttcatgt   6120
gtaacgactt aatgttaaag gttaaaaaaa agatttcaca aaatatacaa ctttcaccat   6180
atatataagc ctgcaaaatt agagtagtga aagtcatgct agtccatcac ccaaatatgt   6240
tatagacgcc atagacaggt gatgtttggt cacctatggt aactgctacc tgatgaagag   6300
cataatttct gcatatccat cctcaatacc atggtaaatt ctggggcaat agagaagcaa   6360
cagaactgcc acaaagtata cctcaatata attcctctag ttctgcttct aaaatctgag   6420
gacagtgcta gtgggaaaat aattttcaaa ctacctggtt aaccaaaata caaaagcagc   6480
tgactatgtg tgatttcata atagcacatt tcttgacact tagtgctaga aatgaagatt   6540
tggattttcc taacaactta catcaagaat gtagtgtagc tcattattga gaatttagga   6600
aagcctgaat ccattaatta aggaaataaa tgtgactcac atttctttta ctgtgacaca   6660
```

ataatgtgat cctaaaactg gcttatcctt gagtgtttac aactcaaaca actttttgaa 6720
tgcagtagtt tttttttttt aaaaacaaac ttttatgtca aatttttttt cttagaagta 6780
gtcttcatta ttataaattt gtacaccaaa aggccatggg gaactttgtg caagtacctc 6840
atcgctgagc aaatggagct tgctatgttt taatttcaga aaatttcctc atatacgtag 6900
tgtgtagaat caagtctttt aataattcat tttttcttca taatatttac tcaaagttaa 6960
gcttaaaaat aagttttatc ttaaaatcat atttgaagac agtaagacag taaactattt 7020
taggaagtca acccccattg cactctgtgg cagttattct ggtaaaaata ggcaaaagtg 7080
acctgaatct acaatgatgt cccaaagtaa ccaagtaaga gagattgtaa atgataaacc 7140
gagctttaaa ggataaagtg ttaataaaga aaggaagctg ggcacatgtc aaaaagggag 7200
atcgaaatgt taggtaatca tttagaaagg acagaaaata tttaaagtgg ctcataggta 7260
atgaatattt ctgacttaga tgtaaatcca tctggaatct ttacatcctt tgccagctga 7320
aacaagaaag tgaagggaca atgatatttc atggtcagtt tattttgtaa gagacagaag 7380
aaattatatc tatacattac cttgtagcag cagtacctgg aagccccagc ccgtcacaga 7440
agtgtggagg ggggctcctg actagacaat ttccctagcc cttgtgattt gaagcatgaa 7500
agttctggca ggttatgagc agcactaggg ataaagtatg gttttatttt ggtgtaattt 7560
aggtttttca acaaagccct tgtctaaaat aaaaggcatt attggaaata tttgaaaact 7620
agaaaatgat ggataaaagg gctgataaga aaatttctgg ctgtcagtag aagtgagata 7680
agatcctcag aggaaacagt aagaagggat aatcattaag atagtaaaac aggcaaagca 7740
gaatcacatg tgcacacaca catacacatg taaacattgg aatgcataag ttttaatatt 7800
ttagcgctat cagtttctaa atgcattaat tactaactgc cctctcccaa gattcattta 7860
gttcaaacag tatccgtaaa ctaggaataa tgccacatgc attcaatggg accttttaag 7920
tactcttcag tttgttccaa gaaatgtgcc tactgaaatc aaattaattt gtattcaatg 7980
tgtacttcaa gactgctaat tgtttcatct gaaagcctac aatgaatcat tgttcaacct 8040
tgaaaaataa aattttgtaa atcaaaaaaa aaaaaaaaaa aa 8082

<210> SEQ ID NO 32
<211> LENGTH: 4880
<212> TYPE: DNA
<213> ORGANISM: Homo sapiens

<400> SEQUENCE: 32
tcactatagg gcgaattggg ccctctagat gcatgctcga gcggccgcca gtgtgatgga 60
tatctgcaga attcgccctt agactctgcg cgcacccaat tcagtcgccc gctcccgttc 120
ggctcctcga agccatggcg ggacctgggg gctggaggga cagggaggtc acggatctgg 180
gccacctgcc ggatccaact ggaatattct cactagataa aaccattggc cttggtactt 240
atggcagaat ctatttggga cttcatgaga agactggtgc atttacagct gttaaagtga 300
tgaacgctcg taagacccct ttacctgaaa taggaaggcg agtgagagtg aataaatatc 360
aaaaatctgt tgggtggaga tacagtgatg aggaagagga tctcaggact gaactcaacc 420
ttctgaggaa gtactctttc cacaaaaaca ttgtgtcctt ctatggagca tttttcaagc 480
tgagtccccc tggtcagcgg caccaacttt ggatggtgat ggagttatgt gcagcaggtt 540
cggtcactga tgtagtgaga atgaccagta atcagagttt aaaagaagat tggattgctt 600
atatctgccg agaaatcctt cagggcttag ctcaccttca cgcacaccga gtaattcacc 660
gggacatcaa aggtcagaat gtgctgctga ctcataatgc tgaagtaaaa ctggttgatt 720

-continued

```
ttggagtgag tgcccaggtg agcagaacta atggaagaag gaatagtttc attgggacac    780
catactggat ggcacctgag gtgattgact gtgatgagga cccaagacgc tcctatgatt    840
acagaagtga tgtgtggtct gtgggaatta ctgccattga aatggctgaa ggagcccctc    900
ctctgtgtaa ccttcaaccc ttggaagctc tcttcgttat tttgcgggaa tctgctccca    960
cagtcaaatc cagcggatgg tcccgtaagt tccacaattt catggaaaag tgtacgataa   1020
aaaatttcct gtttcgtcct acttctgcaa acatgcttca acacccattt gttcgggata   1080
taaaaaatga acgacatgtt gttgagtcat taacaaggca tcttactgga atcattaaaa   1140
aaagacagaa aaaaggaata cctttgatct ttgaaagaga agaagctatt aaggaacagt   1200
acaccgtgag aagattcaga ggaccctctt gcactcacga gcttctgaga ttgccaacca   1260
gcagcagatg cagaccactt agagtcctgc atggggaacc ctctcagcca aggtggctac   1320
ctgatcgaga agagccacag gtccaggcac ttcagcagct acagggagca gccagggtat   1380
tcatgccact gcaggctctg gacagtgcac ctaagcctct aaaggggcag gctcaggcac   1440
ctcaacgact acaaggggca gctcgggtgt tcatgccact acaggctcag gtgaaggcta   1500
aggcctctaa acctctacaa atgcagatta aggcacctcc acgactacgg agggcagcca   1560
gggtgctcat gccactacag gcacaggtta gggcacctag gcttctgcag gtacagtccc   1620
aggtatccaa aaagcagcag gcccagaccc agacatcaga accacaagat ttggaccagg   1680
taccagagga atttcagggt caagatcagg tacccgaaca acaaaggcag ggccaggccc   1740
ctgaacaaca gcagaggcac aaccaggtgc ctgaacaaga gctggagcag aaccaggcac   1800
ctgaacagcc agaggtacag gaacaggctg ccgagcctgc acaggcagag actgaggcag   1860
aggaacctga gtcattacga gtaaatgccc aggtatttct gcccctgcta tcacaagatc   1920
accatgtgct gttgccacta catttggata ctcaggtgct cattccagta gaggggcaaa   1980
ctgaaggatc acctcaggca caggcttgga cactagaacc cccacaggca attggctcag   2040
ttcaagcact gatagaggga ctatcaagag acttgcttcg ggcaccaaac tcaaataact   2100
caaagccact tggtccgttg caaaccctga tggaaaatct gtcatcaaat aggttttact   2160
cacaaccaga acaggcacgg gagaaaaaat caaaagtttc tactctgagg caagcactgg   2220
caaaaagact atcaccaaag aggttcaggg caaagtcatc atggagacct gaaaagcttg   2280
aactctcgga tttagaagcc cgcaggcaaa ggcgccaacg cagatgggaa gatatcttta   2340
atcagcatga ggaagaattg agacaagttg ataaagacaa agaagatgaa tcatcagaca   2400
atgatgaagt atttcattcg attcaggctg aagtccagat agagccattg aagccataca   2460
tttcaaatcc taaaaaaatt gaggttcaag agagatctcc ttctgtgcct aacaaccagg   2520
atcatgcaca tcatgtcaag ttctcttcaa gcgttcctca gcggtctcag tcatcaccac   2580
cttattctac tattgatcag aagttgctgg ttgacatcca tgttccagat ggatttaaag   2640
taggaaaaat atcacccccct gtatacttga caaacgaatg ggtaggctat aatgcactct   2700
ctgaaatctt ccggaatgat tggttaactc cggcacctgt cattcagcca cctgaagagg   2760
atggtgatta tgttgaactc tatgatgcca gtgctgatac tgatggtgat gatgatgatg   2820
agtctaatga tacttttgaa gatacctatg atcatgccaa tggcaatgat gacttggata   2880
accaggttga tcaggctaat gatgtttgta aagaccatga tgatgacaac aataagtttg   2940
ttgatgatgt aaataataat tattatgagg cgcctagttg tccaagggca agctatggca   3000
gagatggaag ctgcaagcaa gatggttatg atggaagtcg tggaaaagag gaagcctaca   3060
gaggctatgg aagccataca gccaatagaa gccatggagg aagtgcagcc agtgaggaca   3120
```

atgcagccat tggagatcag gaagaacatg cagccaatat aggcagtgaa agaagaggca 3180
gtgagggtga tggaggtaag ggagtcgttc gaaccagtga agagagtgga gcccttggac 3240
tcaatggaga agaaaattgc tcagagacag atggtccagg attgaagaga cctgcgtctc 3300
aggactttga atatctacag gaggagccag gtggtggaaa tgaggcctca aatgccattg 3360
actcaggtgc tgcaccgtca gcacctgatc atgagagtga caataaggac atatcagaat 3420
catcaacaca atcagatttt tctgccaatc actcatctcc ttccaaaggt tctgggatgt 3480
ctgctgatgc taactttgcc agtgccatct tatacgctgg attcgtagaa gtacctgagg 3540
aatcacctaa gcaaccctct gaagtcaatg ttaacccact ctatgtctct cctgcatgta 3600
aaaaaccact aatccacatg tatgaaaagg agttcacttc tgagatctgc tgtggttctt 3660
tgtggggagt caatttgctg ttgggaaccc gatctaatct atatctgatg gacagaagtg 3720
gaaaggctga cattactaaa cttataaggc gaagaccatt ccgccagatt caagtcttag 3780
agccactcaa tttgctgatt accatctcag gtcataagaa cagacttcgg gtgtatcatc 3840
tgacctggtt gaggaacaag attttgaata atgatccaga aagtaaaaga aggcaagaag 3900
aaatgctgaa gacagaggaa gcctgcaaag ctattgataa gttaacaggc tgtgaacact 3960
tcagtgttct ccaacatgaa gaaacaacat atattgcaat tgctttgaaa tcatcaattc 4020
acctttatgc atgggcacca aagtcctttg atgaaagcac tgctattaaa gtatttccaa 4080
cacttgatca taagccagtg acagttgacc tggctattgg ttctgaaaaa agactaaaga 4140
ttttcttcag ctcagcagat ggatatcacc tcatcgatgc agaatctgag gttatgtctg 4200
atgtgaccct gccaaagaat cccctggaaa tcattatacc acagaatatc atcattttac 4260
ctgattgctt gggaattggc atgatgctca ccttcaatgc tgaagccctc tctgtggaag 4320
caaatgaaca actcttcaag aagatccttg aaatgtggaa agacatacca tcttctatag 4380
cttttgaatg tacacagcga accacaggat ggggccaaaa ggccattgaa gtgcgctctt 4440
tgcaatccag ggttctggaa agtgagctga agcgcaggtc aattaagaag ctgagattcc 4500
tgtgcacccg gggtgacaag ctgttcttta cctctaccct gcgcaatcac cacagccggg 4560
tttacttcat gacacttgga aaacttgaag agctccaaag caattatgat gtctaaaagt 4620
ttccagtgat ttattaccac attataaaca tcatgtatag gcagtctgca tcttcagatt 4680
tcagagatta aatgagtatt cagttttatt tttagtaaag attaaatcca aaactttact 4740
tttaatgtag cacagaatag ttttaatgag aaatgcagct ttatgtataa aattaactat 4800
agcaagctct aggtactcca atggaagggc gaattccagc acactggcgg ccgttactag 4860
tggatccgag ctcggtacca 4880

<210> SEQ ID NO 33
<211> LENGTH: 4853
<212> TYPE: DNA
<213> ORGANISM: Homo sapiens

<400> SEQUENCE: 33
ggaattgtga gcggataaca atttcacaca ggaaacagct atgaccatga ttacgccaag 60
ctatttaggt gacactatag aatactcaag ctatgcatca agcttggtac cgagctcgga 120
tccactagta acggccgcca gtgtgctgga attcgccctt agactctgcg cgcacccaat 180
tcagtcgccc gctcccgttc ggctcctcga agccatggcg ggacctgggg gctggaggga 240
cagggaggtc acggatctgg gccacctgcc ggatccaact ggaatattct cactagataa 300
aaccattggc cttggtactt atggcagaat ctatttggga cttcatgaga agactggtgc 360

```
atttacagct gttaaagtga tgaacgctcg taagacccct ttacctgaaa taggaaggcg    420
agtgagagtg aataaatatc aaaaatctgt tgggtggaga tacagtgatg aggaagagga    480
tctcaggact gaactcaacc ttctgaggaa gtactctttc cacaaaaaca ttgtgtcctt    540
ctatggagca tttttcaagc tgagtccccc tggtcagcgg caccaacttt ggatggtgat    600
ggagttatgt gcagcaggtt cggtcactga tgtagtgaga atgaccagta atcagagttt    660
aaaagaagat tggattgctt atatctgccg agaaatcctt cagggcttag ctcaccttca    720
cgcacaccga gtaattcacc gggacatcaa aggtcagaat gtgctgctga ctcataatgc    780
tgaagtaaaa ctggttgatt ttggagtgag tgcccaggtg agcagaacta atggaagaag    840
gaatagtttc attgggacac catactggat ggcacctgag gtgattgact gtgatgagga    900
cccaagacgc tcctatgatt acagaagtga tgtgtggtct gtgggaatta ctgccattga    960
aatggctgaa ggagcccctc ctctgtgtaa ccttcaaccc ttggaagctc tcttcgttat   1020
tttgcgggaa tctgctccca cagtcaaatc cagcggatgg tcccgtaagt tccacaattt   1080
catggaaaag tgtacgataa aaaatttcct gtttcgtcct acttctgcaa acatgcttca   1140
acacccattt gttcgggata taaaaaatga acgacatgtt gttgagtcat taacaaggca   1200
tcttactgga atcattaaaa aaagacagaa aaaaggaata cctttgatct ttgaaagaga   1260
agaagctatt aaggaacagt acaccgtgag aagattcaga ggaccctctt gcactcacga   1320
gcttctgaga ttgccaacca gcagcagatg cagaccactt agagtcctgc atggggaacc   1380
ctctcagcca aggtggctac ctgatcgaga agagccacag gtccaggcac ttcagcagct   1440
acagggagca gccagggtat tcatgccact gcaggctctg gacagtgcac ctaagcctct   1500
aaaggggcag gctcaggcac ctcaacgact acaaggggca gctcgggtgt tcatgccact   1560
acaggctcag gtgaaggcta aggcctctaa acctctacaa atgcagatta aggcacctcc   1620
acgactacgg agggcagcca gggtgctcat gccactacag gcacaggtta gggcacctag   1680
gcttctgcag gtacagtccc aggtatccaa aaagcagcag gcccagaccc agacatcaga   1740
accacaagat ttggaccagg taccagagga atttcagggt caagatcagg tacccgaaca   1800
acaaaggcag ggccaggccc ctgaacaaca gcagaggcac aaccaggtgc ctgaacaaga   1860
gctggagcag aaccaggcac ctgaacagcc agaggtacag gaacaggctg ccgagcctgc   1920
acaggcagag actgaggcag aggaacctga gtcattacga gtaaatgccc aggtatttct   1980
gcccctgcta tcacaagatc accatgtgct gttgccacta catttggata ctcaggtgct   2040
cattccagta gaggggcaaa ctgaaggatc acctcaggca caggcttgga cactagaacc   2100
cccacaggca attggctcag ttcaagcact gatagaggga ctatcaagag acttgcttcg   2160
ggcaccaaac tcaaataact caaagccact tggtccgttg caaaccctga tggaaaatct   2220
gtcatcaaat aggttttact cacaaccaga acaggcacgg gagaaaaaat caaaagtttc   2280
tactctgagg caagcactgg caaaaagact atcaccaaag aggttcaggg caaagtcatc   2340
atggagacct gaaaagcttg aactctcgga tttagaagcc cgcaggcaaa ggcgccaacg   2400
cagatgggaa gatatcttta atcagcatga ggaagaattg agacaagttg ataaagacaa   2460
agaagatgaa tcatcagaca atgatgaagt atttcattcg attcaggctg aagtccagat   2520
agagccattg aagccataca tttcaaatcc taaaaaaatt gaggttcaag agagatctcc   2580
ttctgtgcct aacaaccagg atcatgcaca tcatgtcaag ttctcttcaa gcgttcctca   2640
gcggtctctt ttggaacaag ctcagaagcc cattgacatc agacaaagga gttcgcaaaa   2700
tcgtcaaaat tggctggcag catcagaatc ttcttctgag gaagaaagtc ctgtgactgg   2760
```

aaggaggtct cagtcatcac caccttattc tactattgat cagaagttgc tggttgacat 2820
ccatgttcca gatggattta aagtaggaaa aatatcaccc cctgtatact tgacaaacga 2880
atgggtaggc tataatgcac tctctgaaat cttccggaat gattggttaa ctccggcacc 2940
tgtcattcag ccacctgaag aggatggtga ttatgttgaa ctctatgatg ccagtgctga 3000
tactgatggt gatgatgatg atgagtctaa tgatactttt gaagatacct atgatcatgc 3060
caatggcaat gatgacttgg ataaccaggt tgatcaggct aatgatgttt gtaaagacca 3120
tgatgatgac aacaataagt ttgttgatga tgtaaataat aattattatg aggcgcctag 3180
ttgtccaagg gcaagctatg gcagagatgg aagctgcaag caagatggtt atgatggaag 3240
tcgtggaaaa gaggaagcct acagaggcta tggaagccat acagccaata gaagccatgg 3300
aggaagtgca gccagtgagg acaatgcagc cattggagat caggaagaac atgcagccaa 3360
tataggcagt gaaagaagag gcagtgaggg tgatggaggt aagggagtcg ttcgaaccag 3420
tgaagagagt ggagcccttg gactcaatgg agaagaaaat tgctcagaga cagatggtcc 3480
aggattgaag agacctgcgt ctcaggactt tgaatatcta caggaggagc caggtggtgg 3540
aaatgaggcc tcaaatgcca ttgactcagg tgctgcaccg tcagcacctg atcatgagag 3600
tgacaataag gacatatcag aatcatcaac acaatcagat tttctgcca atcactcatc 3660 tccttccaaa ggttctggga tgtctgctga tgctaacttt gccagtgcca tcttatacgc 3720
tggattcgta gaagtacctg aggaatcacc taagcaaccc tctgaagtca atgttaaccc 3780
actctatgtc tctcctgcat gtaaaaaacc actaatccac atgtatgaaa aggagttcac 3840
ttctgagatc tgctgtggtt ctttgtgggg agtcaatttg ctgttgggaa cccgatctaa 3900
tctatatctg atggacagaa gtggaaaggc tgacattact aaacttataa ggcgaagacc 3960
attccgccag attcaagtct tagagccact caatttgctg attaccatct caggtcataa 4020
gaacagactt cgggtgtatc atctgacctg gttgaggaac aagattttga ataatgatcc 4080
agaaagtaaa agaaggcaag aagaaatgct gaagacagag gaagcctgca aagctattga 4140
taagttaaca ggctgtgaac acttcagtgt cctccaacat gaagaaacaa catatattgc 4200
aattgctttg aaatcatcaa ttcaccttta tgcatgggca ccaaagtcct ttgatgaaag 4260
cactgctatt aaagtatttc caacacttga tcataagcca gtgacagttg acctggctat 4320
tggttctgaa aaaagactaa agattttctt cagctcagca gatggatatc acctcatcga 4380
tgcagaatct gaggttatgt ctgatgtgac cctgccaaag aataatatca tcattttacc 4440
tgattgcttg ggaattggca tgatgctcac cttcaatgct gaagccctct ctgtggaagc 4500
aaatgaacaa ctcttcaaga agatccttga aatgtggaaa gacataccat cttctatagc 4560
ttttgaatgt acacagcgaa ccacaggatg ggccaaaag gccattgaag tgcgctcttt 4620
gcaatccagg gttctggaaa gtgagctgaa gcgcaggtca attaagaagc tgagattcct 4680
gtgcacccgg ggtgacaagc tgttctttac ctctaccctg cgcaatcacc acagccgggt 4740
ttacttcatg acacttggaa aacttgaaga gctccaaagc aattatgatg tctaaaagtt 4800
tccagtgatt tattaccaca ttataaacat catgtatagg cagtctgcat ctt 4853

<210> SEQ ID NO 34
<211> LENGTH: 4845
<212> TYPE: DNA
<213> ORGANISM: Homo sapiens

<400> SEQUENCE: 34
acggtgggag gtctatataa gcagagctgg tttagtgaac cgtcagatcc gctagcgcta 60

-continued

```
ccggactcag atctatttag gtgacactat agaagagcca agctgctcga gccgccacca    120
tgggatccgc gggacctggg ggctggaggg acagggaggt cacggatctg ggccacctgc    180
cggatccaac tggaatattc tcactagata aaaccattgg ccttggtact tatggcagaa    240
tctatttggg acttcatgag aagactggtg catttacagc tgttaaagtg atgaacgctc    300
gtaagacccc tttacctgaa ataggaaggc gagtgagagt gaataaatat caaaaatctg    360
ttgggtggag atacagtgat gaggaagagg atctcaggac tgaactcaac cttctgagga    420
agtactcttt ccacaaaaac attgtgtcct tctatggagc atttttcaag ctgagtcccc    480
ctggtcagcg gcaccaactt tggatggtga tggagttatg tgcagcaggt tcggtcactg    540
atgtagtgag aatgaccagt aatcagagtt taaaagaaga ttggattgct tatatctgcc    600
gagaaatcct tcagggctta gctcaccttc acgcacaccg agtaattcac cgggacatca    660
aaggtcagaa tgtgctgctg actcataatg ctgaagtaaa actggttgat tttggagtga    720
gtgcccaggt gagcagaact aatggaagaa ggaatagttt cattgggaca ccatactgga    780
tggcacctga ggtgattgac tgtgatgagg acccaagacg ctcctatgat tacagaagtg    840
atgtgtggtc tgtgggaatt actgccattg aaatggctga aggagcccct cctctgtgta    900
accttcaacc cttggaagct ctcttcgtta ttttgcggga atctgctccc acagtcaaat    960
ccagcggatg gtcccgtaag ttccacaatt tcatggaaaa gtgtacgata aaaaatttcc   1020
tgtttcgtcc tacttctgca aacatgcttc aacacccatt tgttcgggat ataaaaaatg   1080
aacgacatgt tgttgagtca ttaacaaggc atcttactgg aatcattaaa aaaagacaga   1140
aaaaaggaat acctttgatc tttgaaagag aagaagctat taaggaacag tacaccgtga   1200
gaagattcag aggaccctct tgcactcacg agcttctgag attgccaacc agcagcagat   1260
gcagaccact tagagtcctg catggggaac cctctcagcc aaggtggcta cctgatcgag   1320
aagagccaca ggtccaggca cttcagcagc tacagggagc agccagggta ttcatgccac   1380
tgcaggctct ggacagtgca cctaagcctc taaaggggca ggctcaggca cctcaacgac   1440
tacaaggggc agctcgggtg ttcatgccac tacaggctca ggtgaaggct aaggcctcta   1500
aacctctaca aatgcagatt aaggcacctc cacgactacg gagggcagcc agggtgctca   1560
tgccactaca ggcacaggtt agggcaccta ggcttctgca ggtacagtcc caggtatcca   1620
aaaagcagca ggcccagacc cagacatcag aaccacaaga tttggaccag gtaccagagg   1680
aatttcaggg tcaagatcag gtacccgaac aacaaaggca gggccaggcc cctgaacaac   1740
agcagaggca caaccaggtg cctgaacaag agctggagca gaaccaggca cctgaacagc   1800
cagaggtaca ggaacaggct gccgagcctg cacaggcaga gactgaggca gaggaacctg   1860
agtcattacg agtaaatgcc caggtatttc tgcccctgct atcacaagat caccatgtgc   1920
tgttgccact acatttggat actcaggtgc tcattccagt agaggggcaa actgaaggat   1980
cacctcaggc acaggcttgg acactagaac ccccacaggc aattggctca gttcaagcac   2040
tgatagaggg actatcaaga gacttgcttc gggcaccaaa ctcaaataac tcaaagccac   2100
ttggtccgtt gcaaaccctg atggaaaatc tgtcatcaaa taggttttac tcacaaccag   2160
aacaggcacg ggagaaaaaa tcaaaagttt ctactctgag gcaagcactg gcaaaaagac   2220
tatcaccaaa gaggttcagg gcaaagtcat catggagacc tgaaaagctt gaactctcgg   2280
atttagaagc ccgcaggcaa aggcgccaac gcagatggga agatatcttt aatcagcatg   2340
aggaagaatt gagacaagtt gataaagaca aagaagatga atcatcagac aatgatgaag   2400
tatttcattc gattcaggct gaagtccaga tagagccatt gaagccatac atttcaaatc   2460
```

-continued

```
ctaaaaaaat tgaggttcaa gagagatctc cttctgtgcc taacaaccag gatcatgcac   2520
atcatgtcaa gttctcttca agcgttcctc agcggtctct tttggaacaa gctcagaagc   2580
ccattgacat cagacaaagg agttcgcaaa atcgtcaaaa ttggctggca gcatcagaat   2640
cttcttctga ggaagaaagt cctgtgactg gaaggaggtc tcagtcatca ccaccttatt   2700
ctactattga tcagaagttg ctggttgaca tccatgttcc agatggattt aaagtaggaa   2760
aaatatcacc ccctgtatac ttgacaaacg aatgggtagg ctataatgca ctctctgaaa   2820
tcttccggaa tgattggtta actccggcac ctgtcattca gccacctgaa gaggatggtg   2880
attatgttga actctatgat gccagtgctg atactgatgg tgatgatgat gatgagtcta   2940
atgatacttt tgaagatacc tatgatcatg ccaatggcaa tgatgacttg gataaccagg   3000
ttgatcaggc taatgatgtt tgtaaagacc atgatgatga caacaataag tttgttgatg   3060
atgtaaataa taattattat gaggcgccta gttgtccaag ggcaagctat ggcagagatg   3120
gaagctgcaa gcaagatggt tatgatggaa gtcgtggaaa agaggaagcc tacagaggct   3180
atggaagcca tacagccaat agaagccatg gaggaagtgc agccagtgag gacaatgcag   3240
ccattggaga tcaggaagaa catgcagcca atataggcag tgaaagaaga ggcagtgagg   3300
gtgatggagg taagggagtc gttcgaacca gtgaagagag tggagccctt ggactcaatg   3360
gagaagaaaa ttgctcagag acagatggtc caggattgaa gagacctgcg tctcaggact   3420
ttgaatatct acaggaggag ccaggtggtg gaaatgaggc ctcaaatgcc attgactcag   3480
gtgctgcacc gtcagcacct gatcatgaga gtgacaataa ggacatatca gaatcatcaa   3540
cacaatcaga tttttctgcc aatcactcat ctccttccaa aggttctggg atgtctgctg   3600
atgctaactt tgccagtgcc atcttatacg ctggattcgt agaagtacct gaggaatcac   3660
ctaagcaacc ctctgaagtc aatgttaacc cactctatgt ctctcctgca tgtaaaaaac   3720
cactaatcca catgtatgaa aaggagttca cttctgagat ctgctgtggt tctttgtggg   3780
gagtcaattt gctgttggga acccgatcta atctatatct gatggacaga agtggaaagg   3840
ctgacattac taaacttata aggcgaagac cattccgcca gattcaagtc ttagagccac   3900
tcaatttgct gattaccatc tcaggtcata agaacagact tcgggtgtat catctgacct   3960
ggttgaggaa caagattttg aataatgatc cagaaagtaa aagaaggcaa gaagaaatgc   4020
tgaagacaga ggaagcctgc aaagctattg ataagttaac aggctgtgaa cacttcagtg   4080
tcctccaaca tgaagaaaca acatatattg caattgcttt gaaatcatca attcaccttt   4140
atgcatgggc accaaagtcc tttgatgaaa gcactgctat taaagtattt ccaacacttg   4200
atcataagcc agtgacagtt gacctggcta ttggttctga aaaaagacta aagattttct   4260
tcagctcagc agatggatat cacctcatcg atgcagaatc tgaggttatg tctgatgtga   4320
ccctgccaaa gaataatatc atcattttac ctgattgctt gggaattggc atgatgctca   4380
ccttcaatgc tgaagccctc tctgtggaag caaatgaaca actcttcaag aagatccttg   4440
aaatgtggaa agacatacca tcttctatag cttttgaatg tacacagcga accacaggat   4500
ggggccaaaa ggccattgaa gtgcgctctt tgcaatccag ggttctggaa agtgagctga   4560
agcgcaggtc aattaagaag ctgagattcc tgtgcacccg ggtgacaag ctgttcttta   4620
cctctaccct gcgcaatcac cacagccggg tttacttcat gacacttgga aaacttgaag   4680
agctccaaag caattatgat gtcgaattcg gtagcggcga ctacaaggac gatgacgata   4740
agtgagcggc cgcctcggcc aaacatcgat aaaataaaag attttattta gtctccagaa   4800
aaagggggga atgaaagacc ccacctgtag gtttggcaag ctagc                   4845
```

<210> SEQ ID NO 35
<211> LENGTH: 5445
<212> TYPE: DNA
<213> ORGANISM: Homo sapiens
<220> FEATURE:
<221> NAME/KEY: misc_feature
<222> LOCATION: (376)..(376)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t

<400> SEQUENCE: 35
ccttctagct tcttcgtctc caggactgac gctcaggctc ctctctcgcc ttagcccaac 60
ttgctttccc gcctcgcaaa ctccggtttc cctccactcc caactctttt cactacacgt 120
ttcccctcct ctatctccca cgccacgaac cccgatcccc agactcctct ctcccgccct 180
cctccttcct ctctcctccc ttcaactctt catccgcttc cacctcagac tctgcgcgca 240
cccaattcag tcgcccgctc ccgttcggct cctcgaagcc atggcgggac ctgggggctg 300
gagggacagg gaggtcacgg atctgggcca cctgccggat ccaactggaa tattctcact 360
agataaaacc attggncntg gtacttatgg cagaatctat ttgggacttc atgagaagac 420
tggtgcattt acagctgtta aagtgatgaa cgctcgtaag accccttttac ctgaaatagg 480
aaggcgagtg agagtgaata aatatcaaaa atctgttggg tggagataca gtgatgagga 540
agaggatctc aggactgaac tcaaccttct gaggaagtac tctttccaca aaaacattgt 600
gtccttctat ggagcatttt tcaagctgag tccccctggt cagcggcacc aactttggat 660
ggtgatggag ttatgtgcag caggttcggt cactgatgta gtgagaatga ccagtaatca 720
gagtttaaaa gaagattgga ttgcttatat ctgccgagaa atccttcagg gcttagctca 780
ccttcacgca caccgagtaa ttcaccggga catcaaaggt cagaatgtgc tgctgactca 840
taatgctgaa gtaaaactgg ttgattttgg agtgagtgcc caggtgagca gaactaatgg 900
aagaaggaat agtttcattg ggacaccata ctggatggca cctgaggtga ttgactgtga 960
tgaggaccca agacgctcct atgattacag aagtgatgtg tggtctgtgg gaattactgc 1020
cattgaaatg gctgaaggag cccctcctct gtgtaacctt caacccttgg aagctctctt 1080
cgttattttg cgggaatctg ctcccacagt caaatccagc ggatggtccc gtaagttcca 1140
caatttcatg gaaaagtgta cgataaaaaa tttcctgttt cgtcctactt ctgcaaacat 1200
gcttcaacac ccatttgttc gggatataaa aaatgaacga catgttgttg agtcattaac 1260
aaggcatctt actggaatca ttaaaaaaag acagaaaaaa ggaatacctt tgatctttga 1320
aagagaagaa gctattaagg aacagtacac cgtgagaaga ttcagaggac cctcttgcac 1380
tcacgagctt ctgagattgc caaccagcag cagatgcaga ccacttagag tcctgcatgg 1440
ggaaccctct cagccaaggt ggctacctga tcgagaagag ccacaggtcc aggcacttca 1500
gcagctacag ggagcagcca gggtattcat gccactgcag gctctggaca gtgcacctaa 1560
gcctctaaag ggcaggctc aggcacctca acgactacaa ggggcagctc gggtgttcat 1620
gccactacag gctcaggtga aggctaaggc ctctaaacct ctacaaatgc agattaaggc 1680
acctccacga ctacggaggg cagccagggt gctcatgcca ctacaggcac aggttagggc 1740
acctaggctt ctgcaggtac agtcccaggt atccaaaaag cagcaggccc agacccagac 1800
atcagaacca caagatttgg accaggtacc agaggaattt cagggtcaag atcaggtacc 1860
cgaacaacaa aggcagggcc aggcccctga acaacagcag aggcacaacc aggtgcctga 1920
acaagagctg gagcagaacc aggcacctga acagccagag gtacaggaac aggctgccga 1980
gcctgcacag gcagagactg aggcagagga acctgagtca ttacgagtaa atgcccaggt 2040
atttctgccc ctgctatcac aagatcacca tgtgctgttg ccactacatt tggatactca 2100
ggtgctcatt ccagtagagg ggcaaactga aggatcacct caggcacagg cttggacact 2160 agaacccccca caggcaattg gctcagttca agcactgata gagggactat caagagactt 2220
gcttcgggca ccaaactcaa ataactcaaa gccacttggt ccgttgcaaa ccctgatgga 2280
aaatctgtca tcaaataggt tttactcaca accagaacag gcacgggaga aaaaatcaaa 2340
agtttctact ctgaggcaag cactggcaaa aagactatca ccaaagaggt tcagggcaaa 2400
gtcatcatgg agacctgaaa agcttgaact ctcggattta gaagcccgca ggcaaaggcg 2460
ccaacgcaga tgggaagata tctttaatca gcatgaggaa gaattgagac aagttgataa 2520
agacaaagaa gatgaatcat cagacaatga tgaagtattt cattcgattc aggctgaagt 2580
ccagatagag ccattgaagc catacatttc aaatcctaaa aaaattgagg ttcaagagag 2640
atctccttct gtgcctaaca accaggatca tgcacatcat gtcaagttct cttcaaggta 2700
tgtcgttcct cagcggtctc ttttggaaca agctcagaag cccattgaca tcagacaaag 2760
gagttcgcaa aatcgtcaaa attggctggc agcatcagaa tcttcttctg aggaagaaag 2820
tcctgtgact ggaaggaggt ctcagtcatc accaccttat tctactattg atcagaagtt 2880
gctggttgac atccatgttc cagatggatt taaagtagga aaaatatcac cccctgtata 2940
cttgacaaac gaatgggtag gctataatgc actctctgaa atcttccgga atgattggtt 3000
aactccggca cctgtcattc agccacctga agaggatggt gattatgttg aactctatga 3060
tgccagtgct gatactgatg gtgatgatga tgatgagtct aatgatactt ttgaagatac 3120
ctatgatcat gccaatggca atgatgactt ggataaccag gttgatcagg ctaatgatgt 3180
ttgtaaagac catgatgatg acaacaataa gtttgttgat gatgtaaata ataattatta 3240
tgaggcgcct agttgtccaa gggcaagcta tggcagagat ggaagctgca agcaagatgg 3300
ttatgatgga agtcgtggaa aagaggaagc ctacagaggc tatggaagcc atacagccaa 3360
tagaagccat ggaggaagtg cagccagtga ggacaatgca gccattggag atcaggaaga 3420
acatgcagcc aatataggca gtgaaagaag aggcagtgag ggtgatggag gtaagggagt 3480
cgttcgaacc agtgaagaga gtggagccct tggactcaat ggagaagaaa attgctcaga 3540
gacagatggt ccaggattga agagacctgc gtctcaggac tttgaatatc tacaggagga 3600
gccaggtggt ggaaatgagg cctcaaatgc cattgactca ggtgctgcac cgtcagcacc 3660
tgatcatgag agtgacaata aggacatatc agaatcatca acacaatcag atttttctgc 3720
caatcactca tctccttcca aaggttctgg gatgtctgct gatgctaact ttgccagtgc 3780
catcttatac gctggattcg tagaagtacc tgaggaatca cctaagcaac cctctgaagt 3840
caatgttaac ccactctatg tctctcctgc atgtaaaaaa ccactaatcc acatgtatga 3900
aaaggagttc acttctgaga tctgctgtgg ttctttgtgg ggagtcaatt tgctgttggg 3960
aacccgatct aatctatatc tgatggacag aagtggaaag gctgacatta ctaaacttat 4020
aaggcgaaga ccattccgcc agattcaagt cttagagcca ctcaatttgc tgattaccat 4080
ctcaggtcat aagaacagac ttcgggtgta tcatctgacc tggttgagga acaagatttt 4140
gaataatgat ccagaaagta aaagaaggca agaagaaatg ctgaagacag aggaagcctg 4200
caaagctatt gataagttaa caggctgtga acacttcagt gtcctccaac atgaagaaac 4260
aacatatatt gcaattgctt tgaaatcatc aattcacctt tatgcatggg caccaaagtc 4320

```
ctttgatgaa agcactgcta ttaaagtatg cattgatcaa tcagcagact ctgaaggaga   4380

ctacatgtcc tatcaagcct atatacgaat actggcaaaa atacaggcag ctgatccagt   4440

gaaccggttt aagagaccag atgagctcct tcatttgctg aagctcaagg tatttccaac   4500

acttgatcat aagccagtga cagttgacct ggctattggt tctgaaaaaa gactaaagat   4560

tttcttcagc tcagcagatg gatatcacct catcgatgca gaatctgagg ttatgtctga   4620

tgtgaccctg ccaaagaatc ccctggaaat cattatacca cagaatatca tcattttacc   4680

tgattgcttg ggaattggca tgatgctcac cttcaatgct gaagccctct ctgtggaagc   4740

aaatgaacaa ctcttcaaga agatccttga aatgtggaaa gacataccat cttctatagc   4800

ttttgaatgt acacagcgaa ccacaggatg gggccaaaag gccattgaag tgcgctcttt   4860

gcaatccagg gttctggaaa gtgagctgaa gcgcaggtca attaagaagc tgagattcct   4920

gtgcacccgg ggtgacaagc tgttctttac ctctaccctg cgcaatcacc acagccgggt   4980

ttacttcatg acacttggaa aacttgaaga gctccaaagc aattatgatg tctaaaagtt   5040

tccagtgatt tattaccaca ttataaacat catgtatagg cagtctgcat cttcagattt   5100

cagagattaa atgagtattc agttttattt ttagtaaaga ttaaatccaa aactttactt   5160

ttaatgtagc acagaatagt tttaatgaga aatgcagctt tatgtataaa attaactata   5220

gcaagctcta ggtactccaa tggtgtacaa tgtcttttgc acaaactttg taacttttgt   5280

tactgtgaat tcaaacatta ctctttggac agtttggaca gtatctgtat tcagatttta   5340

caacatggag taaagaaacc tgttatgaat tagattacaa gcagccttca aaagaattgg   5400

cactgggata agatttttca ggaaaagaaa aacatcggca aacta                     5445
```

```
<210> SEQ ID NO 36
<211> LENGTH: 1331
<212> TYPE: PRT
<213> ORGANISM: Homo sapiens

<400> SEQUENCE: 36

Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Gly Asp Glu Glu Glu
    50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
        115                 120                 125

Trp Ile Ala Tyr Ile Cys Arg Glu Ile Leu Arg Gly Leu Ser His Leu
    130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175
```

-continued

```
Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Phe Lys Ser Asp Leu Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Lys Lys Lys Arg Gly Glu Lys Asp Glu Thr Glu
305                 310                 315                 320

Tyr Glu Tyr Ser Gly Ser Glu Glu Glu Glu Glu Glu Asn Asp Ser Gly
                325                 330                 335

Glu Pro Ser Ser Ile Leu Asn Leu Pro Gly Glu Ser Thr Leu Arg Arg
            340                 345                 350

Asp Phe Leu Arg Leu Gln Leu Ala Asn Lys Glu Arg Ser Glu Ala Leu
        355                 360                 365

Arg Arg Gln Gln Leu Glu Gln Gln Gln Arg Glu Asn Glu Glu His Lys
    370                 375                 380

Arg Gln Leu Leu Ala Glu Arg Gln Lys Arg Ile Glu Glu Gln Lys Glu
385                 390                 395                 400

Gln Arg Arg Arg Leu Glu Glu Gln Gln Arg Arg Glu Lys Glu Leu Arg
                405                 410                 415

Lys Gln Gln Glu Arg Glu Gln Arg Arg His Tyr Glu Glu Gln Met Arg
            420                 425                 430

Arg Glu Glu Glu Arg Arg Arg Ala Glu His Glu Gln Glu Tyr Lys Arg
        435                 440                 445

Lys Gln Leu Glu Glu Gln Arg Gln Ala Glu Arg Leu Gln Arg Gln Leu
    450                 455                 460

Lys Gln Glu Arg Asp Tyr Leu Val Ser Leu Gln His Gln Arg Gln Glu
465                 470                 475                 480

Gln Arg Pro Val Glu Lys Lys Pro Leu Tyr His Tyr Lys Glu Gly Met
                485                 490                 495

Ser Pro Ser Glu Lys Pro Ala Trp Ala Lys Glu Val Glu Glu Arg Ser
            500                 505                 510

Arg Leu Asn Arg Gln Ser Ser Pro Ala Met Pro His Lys Val Ala Asn
        515                 520                 525

Arg Ile Ser Asp Pro Asn Leu Pro Pro Arg Ser Glu Ser Phe Ser Ile
    530                 535                 540

Ser Gly Val Gln Pro Ala Arg Thr Pro Pro Met Leu Arg Pro Val Asp
545                 550                 555                 560

Pro Gln Ile Pro His Leu Val Ala Val Lys Ser Gln Gly Pro Ala Leu
                565                 570                 575

Thr Ala Ser Gln Ser Val His Glu Gln Pro Thr Lys Gly Leu Ser Gly
            580                 585                 590

Phe Gln Glu Ala Leu Asn Val Thr Ser His Arg Val Glu Met Pro Arg
        595                 600                 605
```

```
Gln Asn Ser Asp Pro Thr Ser Glu Asn Pro Pro Leu Pro Thr Arg Ile
    610                 615                 620

Glu Lys Phe Asp Arg Ser Ser Trp Leu Arg Gln Glu Glu Asp Ile Pro
625                 630                 635                 640

Pro Lys Val Pro Gln Arg Thr Thr Ser Ile Ser Pro Ala Leu Ala Arg
                645                 650                 655

Lys Asn Ser Pro Gly Asn Gly Ser Ala Leu Gly Pro Arg Leu Gly Ser
            660                 665                 670

Gln Pro Ile Arg Ala Ser Asn Pro Asp Leu Arg Arg Thr Glu Pro Ile
        675                 680                 685

Leu Glu Ser Pro Leu Gln Arg Thr Ser Ser Gly Ser Ser Ser Ser Ser
    690                 695                 700

Ser Thr Pro Ser Ser Gln Pro Ser Ser Gln Gly Gly Ser Gln Pro Gly
705                 710                 715                 720

Ser Gln Ala Gly Ser Ser Glu Arg Thr Arg Val Arg Ala Asn Ser Lys
                725                 730                 735

Ser Glu Gly Ser Pro Val Leu Pro His Glu Pro Ala Lys Val Lys Pro
            740                 745                 750

Glu Glu Ser Arg Asp Ile Thr Arg Pro Ser Arg Pro Ala Ser Tyr Lys
        755                 760                 765

Lys Ala Ile Asp Glu Asp Leu Thr Ala Leu Ala Lys Glu Leu Arg Glu
    770                 775                 780

Leu Arg Ile Glu Glu Thr Asn Arg Pro Met Lys Lys Val Thr Asp Tyr
785                 790                 795                 800

Ser Ser Ser Ser Glu Glu Ser Glu Ser Ser Glu Glu Glu Glu Glu Asp
                805                 810                 815

Gly Glu Ser Glu Thr His Asp Gly Thr Val Ala Val Ser Asp Ile Pro
            820                 825                 830

Arg Leu Ile Pro Thr Gly Ala Pro Gly Ser Asn Glu Gln Tyr Asn Val
        835                 840                 845

Gly Met Val Gly Thr His Gly Leu Glu Thr Ser His Ala Asp Ser Phe
    850                 855                 860

Ser Gly Ser Ile Ser Arg Glu Gly Thr Leu Met Ile Arg Glu Thr Ser
865                 870                 875                 880

Gly Glu Lys Lys Arg Ser Gly His Ser Asp Ser Asn Gly Phe Ala Gly
                885                 890                 895

His Ile Asn Leu Pro Asp Leu Val Gln Gln Ser His Ser Pro Ala Gly
            900                 905                 910

Thr Pro Thr Glu Gly Leu Gly Arg Val Ser Thr His Ser Gln Glu Met
        915                 920                 925

Asp Ser Gly Thr Glu Tyr Gly Met Gly Ser Ser Thr Lys Ala Ser Phe
    930                 935                 940

Thr Pro Phe Val Asp Pro Arg Val Tyr Gln Thr Ser Pro Thr Asp Glu
945                 950                 955                 960

Asp Glu Glu Asp Glu Glu Ser Ser Ala Ala Ala Leu Phe Thr Ser Glu
                965                 970                 975

Leu Leu Arg Gln Glu Gln Ala Lys Leu Asn Glu Ala Arg Lys Ile Ser
            980                 985                 990

Val Val Asn Val Asn Pro Thr Asn  Ile Arg Pro His Ser  Asp Thr Pro
        995                 1000                1005

Glu Ile  Arg Lys Tyr Lys Lys  Arg Phe Asn Ser Glu  Ile Leu Cys
    1010                1015                1020

Ala Ala  Leu Trp Gly Val Asn  Leu Leu Val Gly Thr  Glu Asn Gly
```

-continued 1025 1030 1035

Leu Met Leu Leu Asp Arg Ser Gly Gln Gly Lys Val Tyr Asn Leu
1040 1045 1050

Ile Asn Arg Arg Arg Phe Gln Gln Met Asp Val Leu Glu Gly Leu
1055 1060 1065

Asn Val Leu Val Thr Ile Ser Gly Lys Lys Asn Lys Leu Arg Val
1070 1075 1080

Tyr Tyr Leu Ser Trp Leu Arg Asn Arg Ile Leu His Asn Asp Pro
1085 1090 1095

Glu Val Glu Lys Lys Gln Gly Trp Ile Thr Val Gly Asp Leu Glu
1100 1105 1110

Gly Cys Ile His Tyr Lys Val Val Lys Tyr Glu Arg Ile Lys Phe
1115 1120 1125

Leu Val Ile Ala Leu Lys Asn Ala Val Glu Ile Tyr Ala Trp Ala
1130 1135 1140

Pro Lys Pro Tyr His Lys Phe Met Ala Phe Lys Ser Phe Ala Asp
1145 1150 1155

Leu Gln His Lys Pro Leu Leu Val Asp Leu Thr Val Glu Glu Gly
1160 1165 1170

Gln Arg Leu Lys Val Ile Phe Gly Ser His Thr Gly Phe His Val
1175 1180 1185

Ile Asp Val Asp Ser Gly Asn Ser Tyr Asp Ile Tyr Ile Pro Ser
1190 1195 1200

His Ile Gln Gly Asn Ile Thr Pro His Ala Ile Val Ile Leu Pro
1205 1210 1215

Lys Thr Asp Gly Met Glu Met Leu Val Cys Tyr Glu Asp Glu Gly
1220 1225 1230

Val Tyr Val Asn Thr Tyr Gly Arg Ile Thr Lys Asp Val Val Leu
1235 1240 1245

Gln Trp Gly Glu Met Pro Thr Ser Val Ala Tyr Ile His Ser Asn
1250 1255 1260

Gln Ile Met Gly Trp Gly Glu Lys Ala Ile Glu Ile Arg Ser Val
1265 1270 1275

Glu Thr Gly His Leu Asp Gly Val Phe Met His Lys Arg Ala Gln
1280 1285 1290

Arg Leu Lys Phe Leu Cys Glu Arg Asn Asp Lys Val Phe Phe Ala
1295 1300 1305

Ser Val Arg Ser Gly Gly Ser Ser Gln Val Phe Phe Met Thr Leu
1310 1315 1320

Asn Arg Asn Ser Met Met Asn Trp
1325 1330

<210> SEQ ID NO 37
<211> LENGTH: 1166
<212> TYPE: PRT
<213> ORGANISM: Homo sapiens

<400> SEQUENCE: 37

Met Ala Asn Asp Ser Pro Ala Lys Ser Leu Val Asp Ile Asp Leu Ser
1 5 10 15

Ser Leu Arg Asp Pro Ala Gly Ile Phe Glu Leu Val Glu Val Val Gly
20 25 30

Asn Gly Thr Tyr Gly Gln Val Tyr Lys Gly Arg His Val Lys Thr Gly
35 40 45

Gln Leu Ala Ala Ile Lys Val Met Asp Val Thr Glu Asp Glu Glu Glu

```
    50                  55                  60

Glu Ile Lys Leu Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

His Asp Asp Gln Leu Trp Leu Val Met Glu Phe Cys Gly Ala Gly Ser
            100                 105                 110

Ile Thr Asp Leu Val Lys Asn Thr Lys Gly Asn Thr Leu Lys Glu Asp
        115                 120                 125

Trp Ile Ala Tyr Ile Ser Arg Glu Ile Leu Arg Gly Leu Ala His Leu
    130                 135                 140

His Ile His His Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Tyr Arg Ser Asp Leu Trp Ser Cys Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Pro Arg Leu Lys Ser Lys
                245                 250                 255

Lys Trp Ser Lys Lys Phe Phe Ser Phe Ile Glu Gly Cys Leu Val Lys
            260                 265                 270

Asn Tyr Met Gln Arg Pro Ser Thr Glu Gln Leu Leu Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Arg Lys Lys Arg Gly Glu Lys Asp Glu Thr Glu
305                 310                 315                 320

Tyr Glu Tyr Ser Gly Ser Glu Glu Glu Glu Glu Glu Val Pro Glu Gln
                325                 330                 335

Glu Gly Glu Pro Ser Ser Ile Val Asn Val Pro Gly Glu Ser Thr Leu
            340                 345                 350

Arg Arg Asp Phe Leu Arg Leu Gln Gln Glu Asn Lys Glu Arg Ser Glu
        355                 360                 365

Ala Leu Arg Arg Gln Gln Leu Leu Gln Glu Gln Gln Leu Arg Glu Gln
    370                 375                 380

Glu Glu Tyr Lys Arg Gln Leu Leu Ala Glu Arg Gln Lys Arg Ile Glu
385                 390                 395                 400

Gln Gln Lys Glu Gln Arg Arg Arg Leu Glu Glu Gln Gln Arg Arg Glu
                405                 410                 415

Arg Glu Ala Arg Arg Gln Gln Glu Arg Glu Gln Arg Arg Arg Glu Gln
            420                 425                 430

Glu Glu Lys Arg Arg Leu Glu Glu Leu Glu Arg Arg Arg Lys Glu Glu
        435                 440                 445

Glu Glu Arg Arg Arg Ala Glu Glu Glu Lys Arg Arg Val Glu Arg Glu
    450                 455                 460

Gln Glu Tyr Ile Arg Arg Gln Leu Glu Glu Glu Gln Arg His Leu Glu
465                 470                 475                 480
```

```
Val Leu Gln Gln Gln Leu Leu Gln Glu Gln Ala Met Leu Leu His Asp
                485                 490                 495

His Arg Arg Pro His Pro Gln His Ser Gln Gln Pro Pro Pro Pro Gln
            500                 505                 510

Gln Glu Arg Ser Lys Pro Ser Phe His Ala Pro Glu Pro Lys Ala His
        515                 520                 525

Tyr Glu Pro Ala Asp Arg Ala Arg Glu Val Pro Val Arg Thr Thr Ser
    530                 535                 540

Arg Ser Pro Val Leu Ser Arg Arg Asp Ser Pro Leu Gln Gly Ser Gly
545                 550                 555                 560

Gln Gln Asn Ser Gln Ala Gly Gln Arg Asn Ser Thr Ser Ser Ile Glu
                565                 570                 575

Pro Arg Leu Leu Trp Glu Arg Val Glu Lys Leu Val Pro Arg Pro Gly
            580                 585                 590

Ser Gly Ser Ser Ser Gly Ser Ser Asn Ser Gly Ser Gln Pro Gly Ser
        595                 600                 605

His Pro Gly Ser Gln Ser Gly Ser Gly Glu Arg Phe Arg Val Arg Ser
    610                 615                 620

Ser Ser Lys Ser Glu Gly Ser Pro Ser Gln Arg Leu Glu Asn Ala Val
625                 630                 635                 640

Lys Lys Pro Glu Asp Lys Lys Glu Val Phe Arg Pro Leu Lys Pro Ala
                645                 650                 655

Gly Glu Val Asp Leu Thr Ala Leu Ala Lys Glu Leu Arg Ala Val Glu
            660                 665                 670

Asp Val Arg Pro Pro His Lys Val Thr Asp Tyr Ser Ser Ser Ser Glu
        675                 680                 685

Glu Ser Gly Thr Thr Asp Glu Glu Asp Asp Asp Val Glu Gln Glu Gly
    690                 695                 700

Ala Asp Glu Ser Thr Ser Gly Pro Glu Asp Thr Arg Ala Ala Ser Ser
705                 710                 715                 720

Leu Asn Leu Ser Asn Gly Glu Thr Glu Ser Val Lys Thr Met Ile Val
                725                 730                 735

His Asp Asp Val Glu Ser Glu Pro Ala Met Thr Pro Ser Lys Glu Gly
            740                 745                 750

Thr Leu Ile Val Arg Gln Thr Gln Ser Ala Ser Ser Thr Leu Gln Lys
        755                 760                 765

His Lys Ser Ser Ser Ser Phe Thr Pro Phe Ile Asp Pro Arg Leu Leu
    770                 775                 780

Gln Ile Ser Pro Ser Ser Gly Thr Thr Val Thr Ser Val Val Gly Phe
785                 790                 795                 800

Ser Cys Asp Gly Met Arg Pro Glu Ala Ile Arg Gln Asp Pro Thr Arg
                805                 810                 815

Lys Gly Ser Val Val Asn Val Asn Pro Thr Asn Thr Arg Pro Gln Ser
            820                 825                 830

Asp Thr Pro Glu Ile Arg Lys Tyr Lys Lys Arg Phe Asn Ser Glu Ile
        835                 840                 845

Leu Cys Ala Ala Leu Trp Gly Val Asn Leu Leu Val Gly Thr Glu Ser
    850                 855                 860

Gly Leu Met Leu Leu Asp Arg Ser Gly Gln Gly Lys Val Tyr Pro Leu
865                 870                 875                 880

Ile Asn Arg Arg Arg Phe Gln Gln Met Asp Val Leu Glu Gly Leu Asn
                885                 890                 895

Val Leu Val Thr Ile Ser Gly Lys Lys Asp Lys Leu Arg Val Tyr Tyr
            900                 905                 910
```

```
Leu Ser Trp Leu Arg Asn Lys Ile Leu His Asn Asp Pro Glu Val Glu
        915                 920                 925

Lys Lys Gln Gly Trp Thr Thr Val Gly Asp Leu Glu Gly Cys Val His
    930                 935                 940

Tyr Lys Val Val Lys Tyr Glu Arg Ile Lys Phe Leu Val Ile Ala Leu
945                 950                 955                 960

Lys Ser Ser Val Glu Val Tyr Ala Trp Ala Pro Lys Pro Tyr His Lys
                965                 970                 975

Phe Met Ala Phe Lys Ser Phe Gly Glu Leu Val His Lys Pro Leu Leu
            980                 985                 990

Val Asp Leu Thr Val Glu Glu Gly  Gln Arg Leu Lys Val  Ile Tyr Gly
        995                 1000                1005

Ser Cys  Ala Gly Phe His Ala  Val Asp Val Asp Ser  Gly Ser Val
    1010                 1015                 1020

Tyr Asp  Ile Tyr Leu Pro Thr  His Val Arg Lys Asn  Pro His Ser
    1025                 1030                 1035

Met Ile  Gln Cys Ser Ile Lys  Pro His Ala Ile Ile  Ile Leu Pro
    1040                 1045                 1050

Asn Thr  Asp Gly Met Glu Leu  Leu Val Cys Tyr Glu  Asp Glu Gly
    1055                 1060                 1065

Val Tyr  Val Asn Thr Tyr Gly  Arg Ile Thr Lys Asp  Val Val Leu
    1070                 1075                 1080

Gln Trp  Gly Glu Met Pro Thr  Ser Val Ala Tyr Ile  Arg Ser Asn
    1085                 1090                 1095

Gln Thr  Met Gly Trp Gly Glu  Lys Ala Ile Glu Ile  Arg Ser Val
    1100                 1105                 1110

Glu Thr  Gly His Leu Asp Gly  Val Phe Met His Lys  Arg Ala Gln
    1115                 1120                 1125

Arg Leu  Lys Phe Leu Cys Glu  Arg Asn Asp Lys Val  Phe Phe Ala
    1130                 1135                 1140

Ser Val  Arg Ser Gly Gly Ser  Ser Gln Val Tyr Phe  Met Thr Leu
    1145                 1150                 1155

Gly Arg  Thr Ser Leu Leu Ser  Trp
    1160                 1165


<210> SEQ ID NO 38
<211> LENGTH: 1295
<212> TYPE: PRT
<213> ORGANISM: Homo sapiens

<400> SEQUENCE: 38

Met Gly Asp Pro Ala Pro Ala Arg Ser Leu Asp Asp Ile Asp Leu Ser
1               5                   10                  15

Ala Leu Arg Asp Pro Ala Gly Ile Phe Glu Leu Val Glu Val Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Glu Asp Glu Glu Glu
    50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

Asn Asp Asp Gln Leu Trp Leu Val Met Glu Phe Cys Gly Ala Gly Ser
            100                 105                 110
```

```
Val Thr Asp Leu Val Lys Asn Thr Lys Gly Asn Ala Leu Lys Glu Asp
        115                 120                 125

Cys Ile Ala Tyr Ile Cys Arg Glu Ile Leu Arg Gly Leu Ala His Leu
    130                 135                 140

His Ala His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Tyr Arg Ser Asp Ile Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Pro Arg Leu Lys Ser Lys
                245                 250                 255

Lys Trp Ser Lys Lys Phe Ile Asp Phe Ile Asp Thr Cys Leu Ile Lys
            260                 265                 270

Thr Tyr Leu Ser Arg Pro Pro Thr Glu Gln Leu Leu Lys Phe Pro Phe
        275                 280                 285

Ile Arg Asp Gln Pro Thr Glu Arg Gln Val Arg Ile Gln Leu Lys Asp
    290                 295                 300

His Ile Asp Arg Ser Arg Lys Lys Arg Gly Glu Lys Glu Glu Thr Glu
305                 310                 315                 320

Tyr Glu Tyr Ser Gly Ser Glu Glu Glu Asp Asp Ser His Gly Glu Glu
                325                 330                 335

Gly Glu Pro Ser Ser Ile Met Asn Val Pro Gly Glu Ser Thr Leu Arg
            340                 345                 350

Arg Glu Phe Leu Arg Leu Gln Gln Glu Asn Lys Ser Asn Ser Glu Ala
        355                 360                 365

Leu Lys Gln Gln Gln Gln Leu Gln Gln Gln Gln Gln Arg Asp Pro Glu
    370                 375                 380

Ala His Ile Lys His Leu Leu His Gln Arg Gln Arg Arg Ile Glu Glu
385                 390                 395                 400

Gln Lys Glu Glu Arg Arg Arg Val Glu Glu Gln Gln Arg Arg Glu Arg
                405                 410                 415

Glu Gln Arg Lys Leu Gln Glu Lys Glu Gln Gln Arg Arg Leu Glu Asp
            420                 425                 430

Met Gln Ala Leu Arg Arg Glu Glu Glu Arg Arg Gln Ala Glu Arg Glu
        435                 440                 445

Gln Glu Tyr Lys Arg Lys Gln Leu Glu Glu Gln Arg Gln Ser Glu Arg
    450                 455                 460

Leu Gln Arg Gln Leu Gln Gln Glu His Ala Tyr Leu Lys Ser Leu Gln
465                 470                 475                 480

Gln Gln Gln Gln Gln Gln Gln Leu Gln Lys Gln Gln Gln Gln Gln Leu
                485                 490                 495

Leu Pro Gly Asp Arg Lys Pro Leu Tyr His Tyr Gly Arg Gly Met Asn
            500                 505                 510

Pro Ala Asp Lys Pro Ala Trp Ala Arg Glu Val Glu Glu Arg Thr Arg
        515                 520                 525

Met Asn Lys Gln Gln Asn Ser Pro Leu Ala Lys Ser Lys Pro Gly Ser
```

-continued

```
    530                 535                 540

Thr Gly Pro Glu Pro Pro Ile Pro Gln Ala Ser Pro Gly Pro Pro Gly
545                 550                 555                 560

Pro Leu Ser Gln Thr Pro Pro Met Gln Arg Pro Val Glu Pro Gln Glu
                565                 570                 575

Gly Pro His Lys Ser Leu Val Ala His Arg Val Pro Leu Lys Pro Tyr
            580                 585                 590

Ala Ala Pro Val Pro Arg Ser Gln Ser Leu Gln Asp Gln Pro Thr Arg
        595                 600                 605

Asn Leu Ala Ala Phe Pro Ala Ser His Asp Pro Asp Pro Ala Ile Pro
    610                 615                 620

Ala Pro Thr Ala Thr Pro Ser Ala Arg Gly Ala Val Ile Arg Gln Asn
625                 630                 635                 640

Ser Asp Pro Thr Ser Glu Gly Pro Gly Pro Ser Pro Asn Pro Pro Ala
                645                 650                 655

Trp Val Arg Pro Asp Asn Glu Ala Pro Pro Lys Val Pro Gln Arg Thr
            660                 665                 670

Ser Ser Ile Ala Thr Ala Leu Asn Thr Ser Gly Ala Gly Gly Ser Arg
        675                 680                 685

Pro Ala Gln Ala Val Arg Ala Ser Asn Pro Asp Leu Arg Arg Ser Asp
    690                 695                 700

Pro Gly Trp Glu Arg Ser Asp Ser Val Leu Pro Ala Ser His Gly His
705                 710                 715                 720

Leu Pro Gln Ala Gly Ser Leu Glu Arg Asn Arg Val Gly Val Ser Ser
                725                 730                 735

Lys Pro Asp Ser Ser Pro Val Leu Ser Pro Gly Asn Lys Ala Lys Pro
            740                 745                 750

Asp Asp His Arg Ser Arg Pro Gly Arg Pro Ala Asp Phe Val Leu Leu
        755                 760                 765

Lys Glu Arg Thr Leu Asp Glu Ala Pro Arg Pro Pro Lys Lys Ala Met
    770                 775                 780

Asp Tyr Ser Ser Ser Ser Glu Glu Val Glu Ser Ser Glu Asp Asp Glu
785                 790                 795                 800

Glu Glu Gly Glu Gly Gly Pro Ala Glu Gly Ser Arg Asp Thr Pro Gly
                805                 810                 815

Gly Arg Ser Asp Gly Asp Thr Asp Ser Val Ser Thr Met Val Val His
            820                 825                 830

Asp Val Glu Glu Ile Thr Gly Thr Gln Pro Pro Tyr Gly Gly Gly Thr
        835                 840                 845

Met Val Val Gln Arg Thr Pro Glu Glu Glu Arg Asn Leu Leu His Ala
    850                 855                 860

Asp Ser Asn Gly Tyr Thr Asn Leu Pro Asp Val Val Gln Pro Ser His
865                 870                 875                 880

Ser Pro Thr Glu Asn Ser Lys Gly Gln Ser Pro Pro Ser Lys Asp Gly
                885                 890                 895

Ser Gly Asp Tyr Gln Ser Arg Gly Leu Val Lys Ala Pro Gly Lys Ser
            900                 905                 910

Ser Phe Thr Met Phe Val Asp Leu Gly Ile Tyr Gln Pro Gly Gly Ser
        915                 920                 925

Gly Asp Ser Ile Pro Ile Thr Ala Leu Val Gly Gly Glu Gly Thr Arg
    930                 935                 940

Leu Asp Gln Leu Gln Tyr Asp Val Arg Lys Gly Ser Val Val Asn Val
945                 950                 955                 960
```

```
Asn Pro Thr Asn Thr Arg Ala His Ser Glu Thr Pro Glu Ile Arg Lys
                965                 970                 975

Tyr Lys Lys Arg Phe Asn Ser Glu Ile Leu Cys Ala Ala Leu Trp Gly
            980                 985                 990

Val Asn Leu Leu Val Gly Thr Glu  Asn Gly Leu Met Leu  Leu Asp Arg
        995                 1000                1005

Ser Gly  Gln Gly Lys Val Tyr  Gly Leu Ile Gly Arg  Arg Arg Phe
    1010                 1015                 1020

Gln Gln  Met Asp Val Leu Glu  Gly Leu Asn Leu Leu  Ile Thr Ile
    1025                 1030                 1035

Ser Gly  Lys Arg Asn Lys Leu  Arg Val Tyr Tyr Leu  Ser Trp Leu
    1040                 1045                 1050

Arg Asn  Lys Ile Leu His Asn  Asp Pro Glu Val Glu  Lys Lys Gln
    1055                 1060                 1065

Gly Trp  Thr Thr Val Gly Asp  Met Glu Gly Cys Gly  His Tyr Arg
    1070                 1075                 1080

Val Val  Lys Tyr Glu Arg Ile  Lys Phe Leu Val Ile  Ala Leu Lys
    1085                 1090                 1095

Ser Ser  Val Glu Val Tyr Ala  Trp Ala Pro Lys Pro  Tyr His Lys
    1100                 1105                 1110

Phe Met  Ala Phe Lys Ser Phe  Ala Asp Leu Pro His  Arg Pro Leu
    1115                 1120                 1125

Leu Val  Asp Leu Thr Val Glu  Glu Gly Gln Arg Leu  Lys Val Ile
    1130                 1135                 1140

Tyr Gly  Ser Ser Ala Gly Phe  His Ala Val Asp Val  Asp Ser Gly
    1145                 1150                 1155

Asn Ser  Tyr Asp Ile Tyr Ile  Pro Val His Ile Gln  Ser Gln Ile
    1160                 1165                 1170

Thr Pro  His Ala Ile Ile Phe  Leu Pro Asn Thr Asp  Gly Met Glu
    1175                 1180                 1185

Met Leu  Leu Cys Tyr Glu Asp  Glu Gly Val Tyr Val  Asn Thr Tyr
    1190                 1195                 1200

Gly Arg  Ile Ile Lys Asp Val  Val Leu Gln Trp Gly  Glu Met Pro
    1205                 1210                 1215

Thr Ser  Val Ala Tyr Ile Cys  Ser Asn Gln Ile Met  Gly Trp Gly
    1220                 1225                 1230

Glu Lys  Ala Ile Glu Ile Arg  Ser Val Glu Thr Gly  His Leu Asp
    1235                 1240                 1245

Gly Val  Phe Met His Lys Arg  Ala Gln Arg Leu Lys  Phe Leu Cys
    1250                 1255                 1260

Glu Arg  Asn Asp Lys Val Phe  Phe Ala Ser Val Arg  Ser Gly Gly
    1265                 1270                 1275

Ser Ser  Gln Val Tyr Phe Met  Thr Leu Asn Arg Asn  Cys Ile Met
    1280                 1285                 1290

Asn Trp
    1295


<210> SEQ ID NO 39
<211> LENGTH: 1582
<212> TYPE: PRT
<213> ORGANISM: Homo sapiens

<400> SEQUENCE: 39

Met Ala Gly Pro Gly Gly Trp Arg Asp Arg Glu Val Thr Asp Leu Gly
1               5                   10                  15
```

-continued

```
His Leu Pro Asp Pro Thr Gly Ile Phe Ser Leu Asp Lys Thr Ile Gly
            20                  25                  30

Leu Gly Thr Tyr Gly Arg Ile Tyr Leu Gly Leu His Glu Lys Thr Gly
        35                  40                  45

Ala Phe Thr Ala Val Lys Val Met Asn Ala Arg Lys Thr Pro Leu Pro
    50                  55                  60

Glu Ile Gly Arg Arg Val Arg Val Asn Lys Tyr Gln Lys Ser Val Gly
65                  70                  75                  80

Trp Arg Tyr Ser Asp Glu Glu Glu Asp Leu Arg Thr Glu Leu Asn Leu
                85                  90                  95

Leu Arg Lys Tyr Ser Phe His Lys Asn Ile Val Ser Phe Tyr Gly Ala
            100                 105                 110

Phe Phe Lys Leu Ser Pro Pro Gly Gln Arg His Gln Leu Trp Met Val
        115                 120                 125

Met Glu Leu Cys Ala Ala Gly Ser Val Thr Asp Val Val Arg Met Thr
    130                 135                 140

Ser Asn Gln Ser Leu Lys Glu Asp Trp Ile Ala Tyr Ile Cys Arg Glu
145                 150                 155                 160

Ile Leu Gln Gly Leu Ala His Leu His Ala His Arg Val Ile His Arg
                165                 170                 175

Asp Ile Lys Gly Gln Asn Val Leu Leu Thr His Asn Ala Glu Val Lys
            180                 185                 190

Leu Val Asp Phe Gly Val Ser Ala Gln Val Ser Arg Thr Asn Gly Arg
        195                 200                 205

Arg Asn Ser Phe Ile Gly Thr Pro Tyr Trp Met Ala Pro Glu Val Ile
    210                 215                 220

Asp Cys Asp Glu Asp Pro Arg Arg Ser Tyr Asp Tyr Arg Ser Asp Val
225                 230                 235                 240

Trp Ser Val Gly Ile Thr Ala Ile Glu Met Ala Glu Gly Ala Pro Pro
                245                 250                 255

Leu Cys Asn Leu Gln Pro Leu Glu Ala Leu Phe Val Ile Leu Arg Glu
            260                 265                 270

Ser Ala Pro Thr Val Lys Ser Ser Gly Trp Ser Arg Lys Phe His Asn
        275                 280                 285

Phe Met Glu Lys Cys Thr Ile Lys Asn Phe Leu Phe Arg Pro Thr Ser
    290                 295                 300

Ala Asn Met Leu Gln His Pro Phe Val Arg Asp Ile Lys Asn Glu Arg
305                 310                 315                 320

His Val Val Glu Ser Leu Thr Arg His Leu Thr Gly Ile Ile Lys Lys
                325                 330                 335

Arg Gln Lys Lys Gly Ile Pro Leu Ile Phe Glu Arg Glu Glu Ala Ile
            340                 345                 350

Lys Glu Gln Tyr Thr Val Arg Arg Phe Arg Gly Pro Ser Cys Thr His
        355                 360                 365

Glu Leu Leu Arg Leu Pro Thr Ser Ser Arg Cys Arg Pro Leu Arg Val
    370                 375                 380

Leu His Gly Glu Pro Ser Gln Pro Arg Trp Leu Pro Asp Arg Glu Glu
385                 390                 395                 400

Pro Gln Val Gln Ala Leu Gln Gln Leu Gln Gly Ala Ala Arg Val Phe
                405                 410                 415

Met Pro Leu Gln Ala Leu Asp Ser Ala Pro Lys Pro Leu Lys Gly Gln
            420                 425                 430

Ala Gln Ala Pro Gln Arg Leu Gln Gly Ala Ala Arg Val Phe Met Pro
        435                 440                 445
```

Leu Gln Ala Gln Val Lys Ala Lys Ala Ser Lys Pro Leu Gln Met Gln
    450                 455                 460

Ile Lys Ala Pro Pro Arg Leu Arg Arg Ala Ala Arg Val Leu Met Pro
465                 470                 475                 480

Leu Gln Ala Gln Val Arg Ala Pro Arg Leu Leu Gln Val Gln Ser Gln
                485                 490                 495

Val Ser Lys Lys Gln Gln Ala Gln Thr Gln Thr Ser Glu Pro Gln Asp
            500                 505                 510

Leu Asp Gln Val Pro Glu Glu Phe Gln Gly Gln Asp Gln Val Pro Glu
        515                 520                 525

Gln Gln Arg Gln Gly Gln Ala Pro Glu Gln Gln Gln Arg His Asn Gln
    530                 535                 540

Val Pro Glu Gln Glu Leu Glu Gln Asn Gln Ala Pro Glu Gln Pro Glu
545                 550                 555                 560

Val Gln Glu Gln Ala Ala Glu Pro Ala Gln Ala Glu Thr Glu Ala Glu
                565                 570                 575

Glu Pro Glu Ser Leu Arg Val Asn Ala Gln Val Phe Leu Pro Leu Leu
            580                 585                 590

Ser Gln Asp His His Val Leu Leu Pro Leu His Leu Asp Thr Gln Val
        595                 600                 605

Leu Ile Pro Val Glu Gly Gln Thr Glu Gly Ser Pro Gln Ala Gln Ala
    610                 615                 620

Trp Thr Leu Glu Pro Pro Gln Ala Ile Gly Ser Val Gln Ala Leu Ile
625                 630                 635                 640

Glu Gly Leu Ser Arg Asp Leu Leu Arg Ala Pro Asn Ser Asn Asn Ser
                645                 650                 655

Lys Pro Leu Gly Pro Leu Gln Thr Leu Met Glu Asn Leu Ser Ser Asn
            660                 665                 670

Arg Phe Tyr Ser Gln Pro Glu Gln Ala Arg Glu Lys Lys Ser Lys Val
        675                 680                 685

Ser Thr Leu Arg Gln Ala Leu Ala Lys Arg Leu Ser Pro Lys Arg Phe
    690                 695                 700

Arg Ala Lys Ser Ser Trp Arg Pro Glu Lys Leu Glu Leu Ser Asp Leu
705                 710                 715                 720

Glu Ala Arg Arg Gln Arg Arg Gln Arg Arg Trp Glu Asp Ile Phe Asn
                725                 730                 735

Gln His Glu Glu Glu Leu Arg Gln Val Asp Lys Asp Lys Glu Asp Glu
            740                 745                 750

Ser Ser Asp Asn Asp Glu Val Phe His Ser Ile Gln Ala Glu Val Gln
        755                 760                 765

Ile Glu Pro Leu Lys Pro Tyr Ile Ser Asn Pro Lys Lys Ile Glu Val
    770                 775                 780

Gln Glu Arg Ser Pro Ser Val Pro Asn Asn Gln Asp His Ala His His
785                 790                 795                 800

Val Lys Phe Ser Ser Ser Val Pro Gln Arg Ser Leu Leu Glu Gln Ala
                805                 810                 815

Gln Lys Pro Ile Asp Ile Arg Gln Arg Ser Ser Gln Asn Arg Gln Asn
            820                 825                 830

Trp Leu Ala Ala Ser Glu Ser Ser Ser Glu Glu Glu Ser Pro Val Thr
        835                 840                 845

Gly Arg Arg Ser Gln Ser Ser Pro Pro Tyr Ser Thr Ile Asp Gln Lys
    850                 855                 860

Leu Leu Val Asp Ile His Val Pro Asp Gly Phe Lys Val Gly Lys Ile

-continued

```
865                 870                 875                 880

Ser Pro Pro Val Tyr Leu Thr Asn Glu Trp Val Gly Tyr Asn Ala Leu
                885                 890                 895

Ser Glu Ile Phe Arg Asn Asp Trp Leu Thr Pro Ala Pro Val Ile Gln
            900                 905                 910

Pro Pro Glu Glu Asp Gly Asp Tyr Val Glu Leu Tyr Asp Ala Ser Ala
        915                 920                 925

Asp Thr Asp Gly Asp Asp Asp Asp Glu Ser Asn Asp Thr Phe Glu Asp
    930                 935                 940

Thr Tyr Asp His Ala Asn Gly Asn Asp Asp Leu Asp Asn Gln Val Asp
945                 950                 955                 960

Gln Ala Asn Asp Val Cys Lys Asp His Asp Asp Asp Asn Asn Lys Phe
                965                 970                 975

Val Asp Asp Val Asn Asn Asn Tyr Tyr Glu Ala Pro Ser Cys Pro Arg
            980                 985                 990

Ala Ser Tyr Gly Arg Asp Gly Ser  Cys Lys Gln Asp Gly  Tyr Asp Gly
        995                 1000                1005

Ser Arg  Gly Lys Glu Glu Ala  Tyr Arg Gly Tyr Gly  Ser His Thr
    1010                1015                1020

Ala Asn  Arg Ser His Gly Gly  Ser Ala Ala Ser Glu  Asp Asn Ala
    1025                1030                1035

Ala Ile  Gly Asp Gln Glu Glu  His Ala Ala Asn Ile  Gly Ser Glu
    1040                1045                1050

Arg Arg  Gly Ser Glu Gly Asp  Gly Gly Lys Gly Val  Val Arg Thr
    1055                1060                1065

Ser Glu  Glu Ser Gly Ala Leu  Gly Leu Asn Gly Glu  Glu Asn Cys
    1070                1075                1080

Ser Glu  Thr Asp Gly Pro Gly  Leu Lys Arg Pro Ala  Ser Gln Asp
    1085                1090                1095

Phe Glu  Tyr Leu Gln Glu Glu  Pro Gly Gly Gly Asn  Glu Ala Ser
    1100                1105                1110

Asn Ala  Ile Asp Ser Gly Ala  Ala Pro Ser Ala Pro  Asp His Glu
    1115                1120                1125

Ser Asp  Asn Lys Asp Ile Ser  Glu Ser Ser Thr Gln  Ser Asp Phe
    1130                1135                1140

Ser Ala  Asn His Ser Ser Pro  Ser Lys Gly Ser Gly  Met Ser Ala
    1145                1150                1155

Asp Ala  Asn Phe Ala Ser Ala  Ile Leu Tyr Ala Gly  Phe Val Glu
    1160                1165                1170

Val Pro  Glu Glu Ser Pro Lys  Gln Pro Ser Glu Val  Asn Val Asn
    1175                1180                1185

Pro Leu  Tyr Val Ser Pro Ala  Cys Lys Lys Pro Leu  Ile His Met
    1190                1195                1200

Tyr Glu  Lys Glu Phe Thr Ser  Glu Ile Cys Cys Gly  Ser Leu Trp
    1205                1210                1215

Gly Val  Asn Leu Leu Leu Gly  Thr Arg Ser Asn Leu  Tyr Leu Met
    1220                1225                1230

Asp Arg  Ser Gly Lys Ala Asp  Ile Thr Lys Leu Ile  Arg Arg Arg
    1235                1240                1245

Pro Phe  Arg Gln Ile Gln Val  Leu Glu Pro Leu Asn  Leu Leu Ile
    1250                1255                1260

Thr Ile  Ser Gly His Lys Asn  Arg Leu Arg Val Tyr  His Leu Thr
    1265                1270                1275
```

-continued

```
Trp Leu  Arg Asn Lys Ile Leu  Asn Asn Asp Pro Glu  Ser Lys Arg
    1280                 1285                 1290

Arg Gln  Glu Glu Met Leu Lys  Thr Glu Glu Ala Cys  Lys Ala Ile
    1295                 1300                 1305

Asp Lys  Leu Thr Gly Cys Glu  His Phe Ser Val Leu  Gln His Glu
    1310                 1315                 1320

Glu Thr  Thr Tyr Ile Ala Ile  Ala Leu Lys Ser Ser  Ile His Leu
    1325                 1330                 1335

Tyr Ala  Trp Ala Pro Lys Ser  Phe Asp Glu Ser Thr  Ala Ile Lys
    1340                 1345                 1350

Val Cys  Ile Asp Gln Ser Ala  Asp Ser Glu Gly Asp  Tyr Met Ser
    1355                 1360                 1365

Tyr Gln  Ala Tyr Ile Arg Ile  Leu Ala Lys Ile Gln  Ala Ala Asp
    1370                 1375                 1380

Pro Val  Asn Arg Phe Lys Arg  Pro Asp Glu Leu Leu  His Leu Leu
    1385                 1390                 1395

Lys Leu  Lys Val Phe Pro Thr  Leu Asp His Lys Pro  Val Thr Val
    1400                 1405                 1410

Asp Leu  Ala Ile Gly Ser Glu  Lys Arg Leu Lys Ile  Phe Phe Ser
    1415                 1420                 1425

Ser Ala  Asp Gly Tyr His Leu  Ile Asp Ala Glu Ser  Glu Val Met
    1430                 1435                 1440

Ser Asp  Val Thr Leu Pro Lys  Asn Pro Leu Glu Ile  Ile Ile Pro
    1445                 1450                 1455

Gln Asn  Ile Ile Ile Leu Pro  Asp Cys Leu Gly Ile  Gly Met Met
    1460                 1465                 1470

Leu Thr  Phe Asn Ala Glu Ala  Leu Ser Val Glu Ala  Asn Glu Gln
    1475                 1480                 1485

Leu Phe  Lys Lys Ile Leu Glu  Met Trp Lys Asp Ile  Pro Ser Ser
    1490                 1495                 1500

Ile Ala  Phe Glu Cys Thr Gln  Arg Thr Thr Gly Trp  Gly Gln Lys
    1505                 1510                 1515

Ala Ile  Glu Val Arg Ser Leu  Gln Ser Arg Val Leu  Glu Ser Glu
    1520                 1525                 1530

Leu Lys  Arg Arg Ser Ile Lys  Lys Leu Arg Phe Leu  Cys Thr Arg
    1535                 1540                 1545

Gly Asp  Lys Leu Phe Phe Thr  Ser Thr Leu Arg Asn  His His Ser
    1550                 1555                 1560

Arg Val  Tyr Phe Met Thr Leu  Gly Lys Leu Glu Glu  Leu Gln Ser
    1565                 1570                 1575

Asn Tyr  Asp Val
    1580


<210> SEQ ID NO 40
<211> LENGTH: 140
<212> TYPE: PRT
<213> ORGANISM: Homo sapiens

<400> SEQUENCE: 40

Met Ser Asp Val Thr Leu Pro Lys Asn Pro Leu Glu Ile Ile Ile Pro
1               5                   10                  15

Gln Asn Ile Ile Ile Leu Pro Asp Cys Leu Gly Ile Gly Met Met Leu
            20                  25                  30

Thr Phe Asn Ala Glu Ala Leu Ser Val Glu Ala Asn Glu Gln Leu Phe
        35                  40                  45
```

-continued

```
Lys Lys Ile Leu Glu Met Trp Lys Asp Ile Pro Ser Ser Ile Ala Phe
    50                  55                  60

Glu Cys Thr Gln Arg Thr Thr Gly Trp Gly Gln Lys Ala Ile Glu Val
65                  70                  75                  80

Arg Ser Leu Gln Ser Arg Val Leu Glu Ser Glu Leu Lys Arg Arg Ser
                85                  90                  95

Ile Lys Lys Leu Arg Phe Leu Cys Thr Arg Gly Asp Lys Leu Phe Phe
            100                 105                 110

Thr Ser Thr Leu Arg Asn His His Ser Arg Val Tyr Phe Met Thr Leu
        115                 120                 125

Gly Lys Leu Glu Glu Leu Gln Ser Asn Tyr Asp Val
    130                 135                 140
```

MAPKS AS MODIFIERS OF THE RAC, AXIN, AND BETA-CATENIN PATHWAYS AND METHODS OF USE

REFERENCE TO RELATED APPLICATIONS

This application is a U.S. National Stage Application of PCT/US03/37730, filed Nov. 24, 2003, which claims priority to U.S. provisional patent applications 60/429,061 filed Nov. 25, 2002 and 60/437,163 filed Dec. 30, 2002. The contents of the prior applications are hereby incorporated by reference in their entireties.

BACKGROUND OF THE INVENTION

Cell movement is an important part of normal developmental and physiological processes (e.g. epiboly, gastrulation and wound healing), and is also important in pathologies such as tumor progression and metastasis, angiogenesis, inflammation and atherosclerosis. The process of cell movement involves alterations of cell-cell and cell-matrix interactions in response to signals, as well as rearrangement of the actin and microtubule cytoskeletons. The small GTPases of the Rho/Rac family interact with a variety of molecules to regulate the processes of cell motility, cell-cell adhesion and cell-matrix adhesion. Cdc42 and Rac are implicated in the formation of filopodia and lamellipodia required for initiating cell movement, and Rho regulates stress fiber and focal adhesion formation. Rho/Rac proteins are effectors of cadherin/catenin-mediated cell-cell adhesion, and function downstream of integrins and growth factor receptors to regulate cytoskeletal changes important for cell adhesion and motility.

There are five members of the Rho/Rac family in the *C. elegans* genome. rho-1 encodes a protein most similar to human RhoA and RhoC, cdc-42 encodes an ortholog of human Cdc42, and ced-10, mig-2 and rac-2 encode Rac-related proteins. ced-10, mig-2 and rac-2 have partially redundant functions in the control of a number of cell and axonal migrations in the worm, as inactivation of two or all three of these genes causes enhanced migration defects when compared to the single mutants. Furthermore, ced-10; mig-2 double mutants have gross morphological and movement defects not seen in either single mutant, possibly as a secondary effect of defects in cell migration or movements during morphogenesis. These defects include a completely penetrant uncoordinated phenotype, as well as variably penetrant slow-growth, vulval, withered tail, and sterility defects, none of which are seen in either single mutant.

Beta-catenin is an adherens junction protein. Adherens junctions (AJs; also called the zonula adherens) are critical for the establishment and maintenance of epithelial layers, such as those lining organ surfaces. AJs mediate adhesion between cells, communicate a signal that neighboring cells are present, and anchor the actin cytoskeleton. In serving these roles, AJs regulate normal cell growth and behavior. At several stages of embryogenesis, wound healing, and tumor cell metastasis, cells form and leave epithelia. This process, which involves the disruption and reestablishment of epithelial cell-cell contacts, may be regulated by the disassembly and assembly of AJs. AJs may also function in the transmission of the 'contact inhibition' signal, which instructs cells to stop dividing once an epithelial sheet is complete.

The AJ is a multiprotein complex assembled around calcium-regulated cell adhesion molecules called cadherins (Peifer, M. (1993) Science 262: 1667-1668). Cadherins are transmembrane proteins: the extracellular domain mediates homotypic adhesion with cadherins on neighboring cells, and the intracellular domain interacts with cytoplasmic proteins that transmit the adhesion signal and anchor the AJ to the actin cytoskeleton. These cytoplasmic proteins include the alpha-, beta-, and gamma-catenins. The beta-catenin protein shares 70% amino acid identity with both plakoglobin, which is found in desmosomes (another type of intracellular junction), and the product of the *Drosophila* segment polarity gene 'armadillo'. Armadillo is part of a multiprotein AJ complex in Drosophila that also includes some homologs of alpha-catenin and cadherin, and genetic studies indicate that it is required for cell adhesion and cytoskeletal integrity.

Beta-catenin, in addition to its role as a cell adhesion component, also functions as a transcriptional co-activator in the Wnt signaling pathway through its interactions with the family of Tcf and Lef transcription factors (for a review see Polakis, (1999) Current Opinion in Genetics & Development, 9:15-21 and Gat U., et al., (1998) Cell 95:605-614).

Deregulation of beta-catenin signaling is a frequent and early event in the development of a variety of human tumors, including colon cancer, melanoma, ovarian cancer, and prostate cancer. Activation of beta-catenin signaling can occur in tumor cells by loss-of-function mutations in the tumor suppressor genes Axin or APC, as well as by gain-of-function mutations in the oncogene beta-catenin itself. Axin normally functions as a scaffolding protein that binds beta-catenin, APC, and the serine/threonine kinase GSK3-beta. Assembly of this degradation complex allows GSK3-beta to phosphorylate beta-catenin, which leads to beta-catenin ubiquitination and degradation by the proteasome. In the absence of Axin activity, beta-catenin protein becomes stabilized and accumulates in the nucleus where it acts as a transcriptional co-activator with TCF for the induction of target genes, including the cell cycle regulators cyclin D1 and c-Myc.

The APC gene, which is mutant in adenomatous polyposis of the colon, is a negative regulator of beta-catenin signaling (Korinek, V. et al., (1997) Science 275: 1784-1787; Morin, P. J., et al., (1997) Science 275: 1787-1790). The APC protein normally binds to beta-catenin and, in combination with other proteins (including glycogen synthase kinase-3b and axin, is required for the efficient degradation of b-catenin. The regulation of beta-catenin is critical to the tumor suppressive effect of APC and that this regulation can be circumvented by mutations in either APC or beta-catenin.

While mammals contain only a single beta-catenin gene, *C. elegans* contains three (Korswagen H C, et al., (2000) Nature 406:527-32). Each worm beta-catenin appears to, carry out unique functions (Korswagen H C, et al., (2000) Nature 406:527-32, Nartarajan L et al. (2001) Genetics 159: 159-72). Because of the divergence of function in *C. elegans*, it is possible to specifically study beta-catenin role in cell adhesion, which is mediated by the *C. elegans* beta-catenin HMP-2.

The *C. elegans* gene pry-1 is the structural and functional ortholog of vertebrate Axin (Korswagen H C et al. (2002) Genes Dev. 16:1291-302). PRY-1 is predicted to contain conserved RGS and DIX domains that, in Axin, bind APC and Dishevelled, respectively. Overexpression of the *C. elegans* pry-1 gene in zebrafish can fully rescue the mutant phenotype of masterblind, the zebrafish Axin 1 mutation. pry-1 loss-of-function mutations produce several phenotypes that appear to result from increased beta-catenin signaling (Gleason J E et al. (2002) Genes Dev. 16:1281-90; Korswagen et al., supra).

Mitogen-activated protein kinase kinase kinase kinase 4 (MAP4K4) is a serine-threonine kinase that activates the c-Jun N-terminal kinase signaling pathway, and may be involved in TNF alpha signaling (Yao, Z., et al (1999) J Biol Chem 274:2118-25; Huang, T. T., et al (2000) Proc Natl Acad Sci USA 97:1014-9).

KIAA0551 is a protein with high similarity to mitogen-activated protein kinase kinase kinase kinase 6 (MAP4K6) which activates the JUN N terminal kinase (JNK) and p38 MAP kinase pathways.

Misshapen/NIKs-related kinase (MNK) is a member of the germinal center kinase (GCK) family of kinases. MINK activates the cJun N-terminal kinase and the p38 pathways (Dan, I., et al (2000) FEBS Lett 469:19-23).

The ability to manipulate the genomes of model organisms such as *C. elegans* provides a powerful means to analyze biochemical processes that, due to significant evolutionary conservation, have direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example Dulubova I, et al, J Neurochem 2001 April; 77(1):229-38; Cai T, et al., Diabetologia 2001 January; 44(1):81-8; Pasquinelli A E, et al., Nature. 2000 Nov. 2; 408(6808):37-8; Ivanov I P, et al., EMBO J 2000 Apr. 17; 19(8):1907-17; Vajo Z et al., Mamm Genome 1999 October; 10(10):10004). For example, a genetic screen can be carried out in an invertebrate model organism having underexpression (e.g. knockout) or overexpression of a gene (referred to as a “genetic entry point”) that yields a visible phenotype. Additional genes are mutated in a random or targeted manner. When a gene mutation changes the original phenotype caused by the mutation in the genetic entry point, the gene is identified as a “modifier” involved in the same or overlapping pathway as the genetic entry point. When the genetic entry point is an ortholog of a human gene implicated in a disease pathway, such as Rac, axin, and beta-catenin, modifier genes can be identified that may be attractive candidate targets for novel therapeutics.

All references cited herein, including patents, patent applications, publications, and sequence information in referenced Genbank identifier numbers, are incorporated herein in their entireties.

SUMMARY OF THE INVENTION

We have discovered genes that modify the Rac, axin, and beta-catenin pathways in *C. elegans*, and identified their human orthologs, hereinafter referred to as Mitogen activated protein kinases (MAPK). The invention provides methods for utilizing these Rac, axin, and beta-catenin modifier genes and polypeptides to identify MAPK-modulating agents that are candidate therapeutic agents that can be used in the treatment of disorders associated with defective or impaired Rac, axin, or beta-catenin function and/or MAPK function. Preferred MAPK-modulating agents specifically bind to MAPK polypeptides and restore Rac, axin, or beta-catenin function. Other preferred MAPK-modulating agents are nucleic acid modulators such as antisense oligomers and RNAi that repress MAPK gene expression or product activity by, for example, binding to and inhibiting the respective nucleic acid (i.e. DNA or mRNA).

MAPK modulating agents may be evaluated by any convenient in vitro or in vivo assay for molecular interaction with a MAPK polypeptide or nucleic acid. In one embodiment, candidate MAPK modulating agents are tested with an assay system comprising a MAPK polypeptide or nucleic acid. Agents that produce a change in the activity of the assay system relative to controls are identified as candidate Rac, axin, and beta-catenin modulating agents. The assay system may be cell-based or cell-free. MAPK-modulating agents include MAPK related proteins (e.g. dominant negative mutants, and biotherapeutics); MAPK-specific antibodies; MAPK-specific antisense oligomers and other nucleic acid modulators; and chemical agents that specifically bind to or interact with MAPK or compete with MAPK binding partner (e.g. by binding to a MAPK binding partner). In one specific embodiment, a small molecule modulator is identified using kianse assay. In specific embodiments, the screening assay system is selected from a binding assay, an apoptosis assay, a cell proliferation assay, an angiogenesis assay, and a hypoxic induction assay.

In another embodiment, candidate Rac, axin, and beta-catenin pathways modulating agents are further tested using a second assay system that detects changes in the Rac, axin, and beta-catenin pathways, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the Rac, axin, and beta-catenin pathways, such as an angiogenic, apoptotic, or cell proliferation disorder (e.g. cancer).

The invention further provides methods for modulating the MAPK function and/or the Rac, axin, and beta-catenin pathways in a mammalian cell by contacting the mammalian cell with an agent that specifically binds a MAPK polypeptide or nucleic acid. The agent may be a small molecule modulator, a nucleic acid modulator, or an antibody and may be administered to a mammalian animal predetermined to have a pathology associated with the Rac, axin, and beta-catenin pathways.

DETAILED DESCRIPTION OF THE INVENTION

Genetic screens were designed to identify modifiers of the Rac, axin, and beta-catenin pathways in *C. elegans*. For Rac modifiers, the screen was designed to identify modifiers of the Rac signaling pathway that also affect cell migrations in *C. elegans*, where various specific genes were silenced by RNA inhibition (RNAi) in a ced-10; mig-2 double mutant background. For axin modifiers, a reduction of function pry-1 (axin) mutant was used. Various specific genes were silenced by RNA inhibition (RNAi). For beta-catenin modifiers, a weak allele of beta-catenin was used (a homozygous viable mutant of beta-catenin, allele qm39). The hmp-2 (qm-39) strain produces larval worms with a highly penetrant lumpy body phenotype in first stage larval worms (L1s). Various specific genes were silenced by RNA inhibition (RNAi). Methods for using RNAi to silence genes in *C. elegans* are known in the art (Fire A, et al., 1998 Nature 391:806-811; Fire, A. Trends Genet. 15, 358-363 (1999); WO9932619). The ZC504.4 gene was identified as a modifier causing altered phenotypes in the worms in all the above screens, and was identified as modifier of the Rac, axin, and beta-catenin pathways. Accordingly, vertebrate orthologs of this modifier, and preferably the human orthologs, MAPK genes (i.e., nucleic acids and polypeptides), are attractive drug targets for the treatment of pathologies associated with a defective Rac, axin, and beta-catenin signaling pathway, such as cancer.

In vitro and in vivo methods of assessing MAPK function are provided herein. Modulation of the MAPK or their respective binding partners is useful for understanding the association of the Rac, axin, and beta-catenin pathways and its members in normal and disease conditions and for developing diagnostics and therapeutic modalities for Rac, axin, and beta-catenin related pathologies. MAPK-modulating agents that act by inhibiting or enhancing MAPK expression, directly or indirectly, for example, by affecting a MAPK function such as enzymatic (e.g., catalytic) or binding activity, can be identified using methods provided herein. MAPK modulating agents are useful in diagnosis, therapy and pharmaceutical development.

Nucleic Acids and Polypeptides of the Invention

Sequences related to MAPK nucleic acids and polypeptides that can be used in the invention are disclosed in Genbank (referenced by Genbank identifier (GI) number) as GI#s 22041067 (SEQ ID NO: 1), 20521082 (SEQ ID NO:2), 10439341 (SEQ ID NO:3), 6110351 (SEQ ID NO:4), 6110356 (SEQ ID NO:5), 6110359 (SEQ ID NO:6), 6110361 (SEQ ID NO:7), 6110364 (SEQ ID NO:8), 17512195 (SEQ ID NO:9), 6110349 (SEQ ID NO:10), 33416309 (SEQ ID NO:11), 22035601 (SEQ ID NO:12), 4758523 (SEQ ID NO:13), 18553055 (SEQ ID NO:14), 3327187 (SEQ ID NO:15), 6808458 (SEQ ID NO:16), 10438179 (SEQ ID NO:17), 7022424 (SEQ ID NO:18), 22035603 (SEQ ID NO:19), 22035605 (SEQ ID NO:20), 7657334 (SEQ ID NO:21), 21961594 (SEQ ID NO:22), 21321027 (SEQ ID NO:23), 21756143 (SEQ ID NO:24), 27436915 (SEQ ID NO:25), 27436916 (SEQ ID NO:26), 27436918 (SEQ ID NO:27), 20549227 (SEQ ID NO:29), 5340679 (SEQ ID NO:30), and 31874847 (SEQ ID NO:31) for nucleic acid, and GI#s 6110350 (SEQ ID NO:36), 22035602 (SEQ ID NO:37), 7657335 (SEQ ID NO:38), and 20549228 (SEQ ID NO:40) for polypeptides. Additionally, nucleotide sequences of SEQ ID NOs: 28, 32, 33, 34, and 35, and amino acid sequence of SEQ ID NO:39 can also be used in the invention.

The term "MAPK polypeptide" refers to a full-length MAPK protein or a functionally active fragment or derivative thereof. A "functionally active" MAPK fragment or derivative exhibits one or more functional activities associated with a full-length, wild-type MAPK protein, such as antigenic or immunogenic activity, enzymatic activity, ability to bind natural cellular substrates, etc. The functional activity of MAPK proteins, derivatives and fragments can be assayed by various methods known to one skilled in the art (Current Protocols in Protein Science (1998) Coligan et al., eds., John Wiley & Sons, Inc., Somerset, N.J.) and as further discussed below. In one embodiment, a functionally active MAPK polypeptide is a MAPK derivative capable of rescuing defective endogenous MAPK activity, such as in cell based or animal assays; the rescuing derivative may be from the same or a different species. For purposes herein, functionally active fragments also include those fragments that comprise one or more structural domains of a MAPK, such as a kinase domain or a binding domain. Protein domains can be identified using the PFAM program (Bateman A., et al., Nucleic Acids Res, 1999, 27:260-2). For example, the CNH domain (PFAM 00780) of MAPK from SEQ ID NOs:36, 37, 38, and 39, are respectively located at approximately amino acid residues 1018 to 1309, 845 to 1144, 982 to 1273, and 1209 to 1556. Further, protein kinase domains (PFAM 00069) of SEQ ID NOs: 36, 37, 38, and 39, are located respectively at approximately amino acid residues 25 to 289, 25 to 289, 25 to 289, and 25 to 313. Methods for obtaining MAPK polypeptides are also further described below. In some embodiments, preferred fragments are functionally active, domain-containing fragments comprising at least 25 contiguous amino acids, preferably at least 50, more preferably 75, and most preferably at least 100 contiguous amino acids of a MAPK. In further preferred embodiments, the fragment comprises the entire kinase (functionally active) domain.

The term "MAPK nucleic acid" refers to a DNA or RNA molecule that encodes a MAPK polypeptide. Preferably, the MAPK polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with human MAPK. Methods of identifying orthlogs are known in the art. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as *C. elegans*, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195-197; Nicholas et al., 1998, "A Tutorial on Searching Sequence Databases and Sequence Scoring Methods" and references cited therein; W. R. Pearson, 1991, Genomics 11:635-650). This algorithm can be applied to amino acid sequences by using the scoring matrix developed by Dayhoff (Dayhoff: Atlas of Protein Sequences and Structure, M. O. Dayhoff ed., 5 suppl. 3:353-358, National Biomedical Research Foundation, Washington, D.C., USA), and normalized by Gribskov (Gribskov 1986 Nucl. Acids Res. 14(6): 6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of a MAPK. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of a MAPK under high stringency hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 μg/ml herring sperm DNA; hybridization for 18-20 hours at 65° C. in a solution containing 6×SSC, 1× Denhardt's solution, 100 μg/ml yeast tRNA and 0.05% sodium pyrophosphate; and washing of filters at 65° C. for 1 h in a solution containing 0.1× SSC and 0.1% SDS (sodium dodecyl sulfate).

In other embodiments, moderately stringent hybridization conditions are used that are: pretreatment of filters containing nucleic acid for 6 h at 40° C. in a solution containing 35% formamide, 5× SSC, 50 mM Tris-HCl (pH7.5), 5 mM EDTA, 0.1% PVP, 0.1% FICOLL®, 1% BSA, and 500 μg/ml denatured salmon sperm DNA; hybridization for 18-20 h at 40° C. in a solution containing 35% formamide, 5×SSC, 50 mM Tris-HCl (pH7.5), 5 mM EDTA, 0.02% PVP, 0.02% FICOLL®, 0.2% BSA, 100 μg/ml salmon sperm DNA, and 10% (wt/vol) dextran sulfate; followed by washing twice for 1 hour at 55° C. in a solution containing 2× SSC and 0.1% SDS.

Alternatively, low stringency conditions can be used that are: incubation for 8 hours to overnight at 37° C. in a solution comprising 20% formamide, 5×SSC, 50 mM sodium phosphate (pH 7.6), 5× Denhardt's solution, 10% dextran sulfate, and 20 μg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of MAPK Nucleic Acids and Polypeptides MAPK nucleic acids and polypeptides are useful for identifying and testing agents that modulate MAPK function and for other applications related to the involvement of MAPK in the Rac, axin, and beta-catenin pathways. MAPK nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of a MAPK protein for assays used to assess MAPK function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, 2$^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant MAPK is expressed in a cell line known to have defective Rac, axin, and beta-catenin function. The recombinant cells are used in cell-based screening assay systems of the invention, as described further below.

The nucleotide sequence encoding a MAPK polypeptide can be inserted into any appropriate expression vector. The necessary transcriptional and translational signals, including promoter/enhancer element, can derive from the native MAPK gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. An isolated host cell strain that modulates the expression of, modifies, and/or specifically processes the gene product may be used.

To detect expression of the MAPK gene product, the expression vector can comprise a promoter operably linked to a MAPK gene nucleic acid, one or more origins of replication, and, one or more selectable markers (e.g. thymidine kinase activity, resistance to antibiotics, etc.). Alternatively, recombinant expression vectors can be identified by assaying for the expression of the MAPK gene product based on the physical or functional properties of the MAPK protein in in vitro assay systems (e.g. immunoassays).

The MAPK protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the MAPK gene sequence is identified, the gene product can be isolated and purified using standard methods (e.g. ion exchange, affinity, and gel exclusion chromatography; centrifugation; differential solubility; electrophoresis). Alternatively, native MAPK proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of MAPK or other genes associated with the Rac, axin, and beta-catenin pathways. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter MAPK expression may be used in in vivo assays to test for activity of a candidate Rac, axin, and beta-catenin modulating agent, or to further assess the role of MAPK in a Rac, axin, and beta-catenin pathways process such as apoptosis or cell proliferation. Preferably, the altered MAPK expression results in a detectable phenotype, such as decreased or increased levels of cell proliferation, angiogenesis, or apoptosis compared to control animals having normal MAPK expression. The genetically modified animal may additionally have altered Rac, axin, and beta-catenin expression (e.g. Rac, axin, or beta-catenin knockout). Preferred genetically modified animals are mammals such as primates, rodents (preferably mice or rats), among others. Preferred non-mammalian species include zebrafish, *C. elegans*, and *Drosophila*. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic *Drosophila* see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish; amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous MAPK gene that results in a decrease of MAPK function, preferably such that MAPK expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse MAPK gene is used to construct a homologous recombination vector suitable for altering an endogenous MAPK gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270: 8397-400).

In another embodiment, the transgenic animal is a "knock-in" animal having an alteration in its genome that results in altered expression (e.g., increased (including ectopic) or decreased expression) of the MAPK gene, e.g., by introduction of additional copies of MAPK, or by operatively inserting a regulatory sequence that provides for altered expression of an endogenous copy of the MAPK gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of *Saccharomyces cerevisiae* (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the Rac, axin, and beta-catenin pathways, as animal models of disease and disorders implicating defective Rac, axin, and beta-catenin function, and for in vivo testing of candidate therapeutic agents, such as those identified in screens described below. The candidate therapeutic agents are administered to a genetically modified animal having altered MAPK function and phenotypic changes are compared with appropriate control animals such as genetically modified animals that receive placebo treatment, and/or animals with unaltered MAPK expression that receive candidate therapeutic agent.

In addition to the above-described genetically modified animals having altered MAPK function, animal models having defective Rac, axin, or beta-catenin function (and otherwise normal MAPK function), can be used in the methods of the present invention. For example, a Rac, axin, or beta-catenin knockout mouse can be used to assess, in vivo, the activity of a candidate Rac, axin, and beta-catenin modulating agent identified in one of the in vitro assays described below. Preferably, the candidate Rac, axin, and beta-catenin modulating agent when administered to a model system with cells defective in Rac, axin, and beta-catenin function, produces a detectable phenotypic change in the model system indicating that the Rac, axin, and beta-catenin function is restored, i.e., the cells exhibit normal cell cycle progression.

Modulating Agents

The invention provides methods to identify agents that interact with and/or modulate the function of MAPK and/or the Rac, axin, and beta-catenin pathways. Modulating agents identified by the methods are also part of the invention. Such agents are useful in a variety of diagnostic and therapeutic applications associated with the Rac, axin, and beta-catenin pathways, as well as in further analysis of the MAPK protein and its contribution to the Rac, axin, and beta-catenin pathways. Accordingly, the invention also provides methods for modulating the Rac, axin, and beta-catenin pathways comprising the step of specifically modulating MAPK activity by administering a MAPK-interacting or -modulating agent.

As used herein, a "MAPK-modulating agent" is any agent that modulates MAPK function, for example, an agent that interacts with MAPK to inhibit or enhance MAPK activity or otherwise affect normal MAPK function. MAPK function can be affected at any level, including transcription, protein expression, protein localization, and cellular or extra-cellular activity. In a preferred embodiment, the MAPK-modulating agent specifically modulates the function of the MAPK. The phrases "specific modulating agent", "specifically modulates", etc., are used herein to refer to modulating agents that directly bind to the MAPK polypeptide or nucleic acid, and preferably inhibit, enhance, or otherwise alter, the function of the MAPK. These phrases also encompass modulating agents that alter the interaction of the MAPK with a binding partner, substrate, or cofactor (e.g. by binding to a binding partner of a MAPK, or to a protein/binding partner complex, and altering MAPK function). In a further preferred embodiment, the MAPK-modulating agent is a modulator of the Rac, axin, and beta-catenin pathways (e.g. it restores and/or upregulates Rac, axin, and beta-catenin function) and thus is also a Rac, axin, and beta-catenin-modulating agent.

Preferred MAPK-modulating agents include small molecule compounds; MAPK-inter acting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., $19^{th}$ edition.

Small Molecule Modulators

Small molecules are often preferred to modulate function of proteins with enzymatic function, and/or containing protein interaction domains. Chemical agents, referred to in the art as "small molecule" compounds are typically organic, non-peptide molecules, having a molecular weight up to 10,000, preferably up to 5,000, more preferably up to 1,000, and most preferably up to 500 daltons. This class of modulators includes chemically synthesized molecules, for instance, compounds from combinatorial chemical libraries. Synthetic compounds may be rationally designed or identified based on known or inferred properties of the MAPK protein or may be identified by screening compound libraries. Alternative appropriate modulators of this class are natural products, particularly secondary metabolites from organisms such as plants or fungi, which can also be identified by screening compound libraries for MAPK-modulating activity. Methods for generating and obtaining compounds are well known in the art (Schreiber S L, Science (2000) 151: 1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with the Rac, axin, and beta-catenin pathways. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific MAPK-interacting proteins are useful in a variety of diagnostic and therapeutic applications related to the Rac, axin, and beta-catenin pathways and related disorders, as well as in validation assays for other MAPK-modulating agents. In a preferred embodiment, MAPK-interacting proteins affect normal MAPK function, including transcription, protein expression, protein localization, and cellular or extra-cellular activity. In another embodiment, MAPK-interacting proteins are useful in detecting and providing informnation about the function of MAPK proteins, as is relevant to Rac, axin, and beta-catenin related disorders, such as cancer (e.g., for diagnostic means).

A MAPK-interacting protein may be endogenous, i.e. one that naturally interacts genetically or biochemically with a MAPK, such as a member of the MAPK pathway that modulates MAPK expression, localization, and/or activity. MAPK-modulators include dominant negative forms of MAPK-interacting proteins and of MAPK proteins themselves. Yeast two-hybrid and variant screens offer preferred methods for identifying endogenous MAPK-interacting proteins (Finley, R. L. et al. (1996) in DNA Cloning-Expression Systems: A Practical Approach, eds. Glover D. & Hames B. D (Oxford University Press, Oxford, England), pp. 169-203; Fashema S F et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928,868). Mass spectrometry is an alternative preferred method for the elucidation of protein complexes (reviewed in, e.g., Pandley A and Mann M, Nature (2000) 405:837-846; Yates JR 3rd, Trends Genet (2000) 16:5-8).

An MAPK-interacting protein may be an exogenous protein, such as a MAPK-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). MAPK antibodies are further discussed below.

In preferred embodiments, a MAPK-interacting protein specifically binds a MAPK protein. In alternative preferred embodiments, a MAPK-modulating agent binds a MAPK substrate, binding partner, or cofactor.

Antibodies

In another embodiment, the protein modulator is a MAPK specific antibody agonist or antagonist. The antibodies have therapeutic and diagnostic utilities, and can be used in screening assays to identify MAPK modulators. The antibodies can also be used in dissecting the portions of the MAPK pathway responsible for various cellular responses and in the general processing and maturation of the MAPK.

Antibodies that specifically bind MAPK polypeptides can be generated using known methods. Preferably the antibody is specific to a mammalian ortholog of MAPK polypeptide, and more preferably, to human MAPK. Antibodies may be polyclonal, monoclonal (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above. Epitopes of MAPK which are particularly antigenic can be selected, for example, by routine screening of MAPK polypeptides for antigenicity or by applying a theoretical method for selecting antigenic regions of a protein (Hopp and Wood (1981), Proc. Natl. Acad. Sci. U.S.A. 78:3824-28; Hopp and Wood, (1983) Mol. Immunol. 20:483-89; Sutcliffe et al., (1983) Science 219:660-66) to the amino acid sequence of a MAPK. Monoclonal antibodies with affinities of $10^8$ $M^{-1}$ preferably $10^9$ $M^{-1}$ to $10^{10}$ $M^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of MAPK or substantially purified fragments thereof. If MAPK fragments are used, they preferably comprise at least 10, and more preferably, at least 20 contiguous amino acids of a MAPK protein. In a particular embodiment, MAPK-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of MAPK-specific antibodies is assayed by an appropriate assay such as a solid phase enzyme-linked immunosorbant assay (ELISA®) using immobilized corresponding MAPK polypeptides. Other assays, such as radioimmunoassays or fluorescent assays might also be used.

Chimeric antibodies specific to MAPK polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann L M, et al., 1988 Nature 323: 323-327). Humanized antibodies contain ~10% murine sequences and ~90% human sequences, and thus further reduce or eliminate immunogenicity, while retaining the antibody specificities (Co M S, and Queen C. 1991 Nature 351: 501-501; Morrison S L. 1992 Ann. Rev. Immun. 10:239-265). Humanized antibodies and methods of their production are well-known in the art (U.S. Pat. Nos. 5,530,101, 5,585,089, 5,693,762, and 6,180,370).

MAPK-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246: 1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816, 567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg-to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859,206; WO0073469).

Nucleic Acid Modulators

Other preferred MAPK-modulating agents comprise nucleic acid molecules, such as antisense oligomers or double stranded RNA (dsRNA), which generally inhibit MAPK activity. Preferred nucleic acid modulators interfere with the function of the MAPK nucleic acid such as DNA replication, transcription, translocation of the MAPK RNA to the site of protein translation, translation of protein from the MAPK RNA, splicing of the MAPK RNA to yield one or more MRNA species, or catalytic activity which may be engaged in or facilitated by the MAPK RNA.

In one embodiment, the antisense oligomer is an oligonucleotide that is sufficiently complementary to a MAPK mRNA to bind to and prevent translation, preferably by binding to the 5' untranslated region. MAPK-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22(3):271-281; Summerton J, and Weller D. 1997 Antisense Nucleic Acid Drug Dev.:7:187-95; U.S. Pat. No. 5,235,033; and U.S. Pat. No. 5,378,841).

Alternative preferred MAPK nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in *C. elegans, Drosophila*, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411:494-498).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, a MAPK-specific nucleic acid modulator is used in an assay to further elucidate the role of the MAPK in the Rac, axin, and beta-catenin pathways, and/or its relationship to other members of the pathway. In another aspect of the invention, a MAPK-specific antisense oligomer is used as a therapeutic agent for treatment of Rac, axin, and beta-catenin-related disease states.

Assay Systems

The invention provides assay systems and screening methods for identifying specific modulators of MAPK activity. As used herein, an "assay system" encompasses all the components required for performing and analyzing results of an assay that detects and/or measures a particular event. In general, primary assays are used to identify or confirm a modulator's specific biochemical or molecular effect with respect to the MAPK nucleic acid or protein. In general, secondary assays further assess the activity of a MAPK modulating agent identified by a primary assay and may confirm that the modulating agent affects MAPK in a manner relevant to the Rac, axin, and beta-catenin pathways. In some cases, MAPK modulators will be directly tested in a secondary assay.

In a preferred embodiment, the screening method comprises contacting a suitable assay system comprising a MAPK polypeptide or nucleic acid with a candidate agent under conditions whereby, but for the presence of the agent, the system provides a reference activity (e.g. kinase activity), which is based on the particular molecular event the screening method detects. A statistically significant difference between the agent-biased activity and the reference activity indicates that the candidate agent modulates MAPK activity, and hence the Rac, axin, and beta-catenin pathways. The MAPK polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicty and changes in cellular morphology or other cellular characteristics. Appropriate screening assays may use a wide range of detection methods including fluorescent, radioactive, calorimetric, spectrophotometric, and amperometric methods, to provide a read-out for the particular molecular event detected.

Cell-based screening assays usually require systems for recombinant expression of MAPK and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when MAPK-interacting proteins are used in screens to identify small molecule modulators, the binding specificity of the interacting protein to the MAPK protein may be assayed by various known methods such as substrate processing (e.g. ability of the candidate MAPK-specific binding agents to function as negative effectors in MAPK-expressing cells), binding equilibrium constants (usually at least about $10^7$ $M^{-1}$, preferably at least about $10^8$ $M^{-1}$, more preferably at least about $10^9$ $M^{-1}$), and immunogenicity (e.g. ability to elicit MAPK specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a MAPK polypeptide, a fusion protein thereof, or to cells or membranes bearing the polypeptide or fusion protein. The MAPK polypeptide can be full length or a fragment thereof that retains functional MAPK activity. The MAPK polypeptide may be fused to another polypeptide, such as a peptide tag for detection or anchoring, or to another tag. The MAPK polypeptide is preferably human MAPK, or is an ortholog or derivative thereof as described above. In a preferred embodiment, the screening assay detects candidate agent-based modulation of MAPK interaction with a binding target, such as an endogenous or exogenous protein or other substrate that has MAPK-specific binding activity, and can be used to assess normal MAPK gene function.

Suitable assay formats that may be adapted to screen for MAPK modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes P B, supra; Hertzberg R P and Pope A J, Curr Opin Chem Biol (2000) 4:445-451).

A variety of suitable assay systems may be used to identify candidate MAPK and Rac, axin, and beta-catenin pathways modulators (e.g. U.S. Pat. No. 6,165,992 (kinase assays); U.S. Pat. Nos. 5,550,019 and 6,133,437 (apoptosis assays); and U.S. Pat. Nos. 5,976,782, 6,225,118 and 6,444,434 (angiogenesis assays), among others). Specific preferred assays are described in more detail below.

Protein kinases, key signal transduction proteins that may be either membrane-associated or intracellular, catalyze the transfer of gamma phosphate from adenosine triphosphate (ATP) to a serine, threonine or tyrosine residue in a protein substrate. Radioassays, which monitor the transfer from [gamma-$^{32}$P or -$^{33}$P]ATP, are frequently used to assay kinase activity. For instance, a scintillation assay for p56 (lck) kinase activity monitors the transfer of the gamma phosphate from [gamma-$^{33}$P] ATP to a biotinylated peptide substrate. The substrate is captured on a streptavidin coated bead that transmits the signal (Beveridge M et al., J Biomol Screen (2000) 5:205-212). This assay uses the scintillation proximity assay (SPA), in which only radio-ligand bound to receptors tethered to the surface of an SPA bead are detected by the scintillant immobilized within it, allowing binding to be measured without separation of bound from free ligand. Other assays for protein kinase activity may use antibodies that specifically recognize phosphorylated substrates. For instance, the kinase receptor activation (KIRA) assay measures receptor tyrosine kinase activity by ligand stimulating the intact receptor in cultured cells, then capturing solubilized receptor with specific antibodies and quantifying phosphorylation via phosphotyrosine ELISA (Sadick M D, Dev Biol Stand (1999) 97:121-133). Another example of antibody based assays for protein kinase activity is TRF (time-resolved fluorometry). This method utilizes europium chelate-labeled anti-phosphotyrosine antibodies to detect phosphate transfer to a polymeric substrate coated onto microtiter plate wells. The amount of phosphorylation is then detected using time-resolved, dissociation-enhanced fluorescence (Braunwalder A F, et al., Anal Biochem 1996 Jul. 1; 238(2):159-64).

Apoptosis assays. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730-41). Other cell-based apoptosis assays include the caspase-3/7 assay and the cell death nucleosome ELISA® assay. The caspase 3/7 assay is based on the activation of the caspase cleavage activity as part of a cascade of events that occur during programmed cell death in many apoptotic pathways. In the caspase 3/7 assay (commercially available APO-ONE™ Homogeneous Caspase-3/7 assay from Promega, cat# 67790), lysis buffer and caspase substrate are mixed and added to cells. The caspase substrate becomes fluorescent when cleaved by active caspase 3/7. The nucleosome ELISA™ assay is a general cell death assay known to those skilled in the art, and available commercially (Roche, Cat# 1774425). This assay is a quantitative sandwich-enzyme-immunoassay which uses monoclonal antibodies directed against DNA and histones respectively, thus specifically determining the amount of mono- and oligonucleosomes in the cytoplasmic fraction of cell lysates. Mono and oligonucleosomes are enriched in the cytoplasm during apoptosis due to the fact that DNA fragmentation occurs several hours before the plasma membrane breaks down, allowing for accumulation in the cytoplasm. Nucleosomes are not present in the cytoplasmic fraction of cells that are not undergoing apoptosis. An apoptosis assay system may comprise a cell that expresses a MAPK, and that optionally has defective Rac, axin, or beta-catenin function (e.g. Rac, axin, or beta-catenin is over-expressed or under-expressed relative to wild-type cells). A test agent can be added to the apoptosis assay system and changes in induction of apoptosis relative to controls where no test agent is added identify candidate Rac, axin, and beta-catenin modulating agents. In some embodiments of the invention, an apoptosis assay may be used as a secondary assay to test a candidate Rac, axin, and beta-catenin modulating agents that is initially identified using a cell-free assay system. An apoptosis assay may also be used to test whether MAPK function plays a direct role in apoptosis. For example, an apoptosis assay may be performed on cells that over- or under-express MAPK relative to wild type cells. Differences in apoptotic response compared to wild type cells suggests that the MAPK plays a direct role in the apoptotic response. Apoptosis assays are described further in U.S. Pat. No. 6,133,437.

Cell proliferation and cell cycle assays. Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et aL, 1986, Int. J. Cancer 38, 369; Campana et al., 1988, J. Immunol. Meth. 107, 79), or by other means.

Cell proliferation is also assayed via phospho-histone H3 staining, which identifies a cell population undergoing mitosis by phosphorylation of histone H3. Phosphorylation of histone H3 at serine 10 is detected using an antibody specific to the phosphorylated form of the serine 10 residue of histone H3. (Chadlee, D. N. 1995, J. Biol. Chem 270:20098-105). Cell proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman L S 3800 Liquid Scintillation Counter). Another proliferation assay uses the dye Alamar Blue (available from Biosource International), which fluoresces when reduced in living cells and provides an indirect measurement of cell number (Voytik-Harbin S L et al., 1998, In Vitro Cell Dev Biol Anim 34:239-46). Yet another proliferation assay, the MTS assay, is based on in vitro cytotoxicity assessment of industrial chemicals, and uses the soluble tetrazolium salt, MTS. MTS assays are commercially available, for example, the Promega CELLTITER 96® Aqueous Non-Radioactive Cell Proliferation Assay (Cat.# G5421).

Cell proliferation may also be assayed by colony formation in soft agar (Sambrook et al., Molecular Cloning, Cold Spring Harbor (1989)). For example, cells transformed with MAPK are seeded in soft agar plates, and colonies are measured and counted after two weeks incubation.

Cell proliferation may also be assayed by measuring ATP levels as indicator of metabolically active cells. Such assays are commercially available, for example CELL TITER-GLO™, which is a luminescent homogeneous assay available from Promega.

Involvement of a gene in the cell cycle may be assayed by flow cytometry (Gray J W et al. (1986) Int J Radiat Biol Relat Stud Phys Chem Med 49:237-55). Cells transfected with a MAPK may be stained with propidium iodide and evaluated in a flow cytometer (available from Becton Dickinson), which indicates accumulation of cells in different stages of the cell cycle.

Accordingly, a cell proliferation or cell cycle assay system may comprise a cell that expresses a MAPK, and that optionally has defective Rac, axin, or beta-catenin function (e.g. Rac, axin, or beta-catenin is over-expressed or under-expressed relative to wild-type cells). A test agent can be added to the assay system and changes in cell proliferation or cell cycle relative to controls where no test agent is added, identify candidate Rac, axin, and beta-catenin modulating agents. In some embodiments of the invention, the cell proliferation or cell cycle assay may be used as a secondary assay to test a candidate Rac, axin, and beta-catenin modulating agents that is initially identified using another assay system such as a cell-free assay system. A cell proliferation assay may also be used to test whether MAPK function plays a direct role in cell proliferation or cell cycle. For example, a cell proliferation or cell cycle assay may be performed on cells that over- or under-express MAPK relative to wild type cells. Differences in proliferation or cell cycle compared to wild type cells suggests that the MAPK plays a direct role in cell proliferation or cell cycle.

Angiogenesis. Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in the presence or absence of angiogenesis enhancer or suppressors; and tubule formation assays based on the formation of tubular structures by endothelial cells on MATRIGEL® (Becton Dickinson). Accordingly, an angiogenesis assay system may comprise a cell that expresses a MAPK, and that optionally has defective Rac, axin, or beta-catenin function (e.g. Rac, axin, or beta-catenin is over-expressed or under-expressed relative to wild-type cells). A test agent can be added to the angiogenesis assay system and changes in angiogenesis relative to controls where no test agent is added identify candidate Rac, axin, and beta-catenin modulating agents. In some embodiments of the invention, the angiogenesis assay may be used as a secondary assay to test a candidate Rac, axin, and beta-catenin modulating agent that is initially identified using another assay system. An angiogenesis assay may also be used to test whether MAPK function plays a direct role in cell proliferation. For example, an angiogenesis assay may be performed on cells that over- or under-express MAPK relative to wild type cells. Differences in angiogenesis compared to wild type cells suggest that the MAPK plays a direct role in angiogenesis. U.S. Pat. Nos. 5,976,782, 6,225,118 and 6,444,434, among others, describe various angiogenesis assays.

Hypoxic induction. The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glycolytic enzymes and VEGF. Induction of such genes by hypoxic conditions may be assayed by growing cells transfected with MAPK in hypoxic conditions (such as with 0.1% O2, 5% CO2, and balance N2, generated in a NAPCO® 7001 incubator (Precision Scientific)) and normoxic conditions, followed by assessment of gene activity or expression by TAQMAN®. For example, a hypoxic induction assay system may comprise a cell that expresses a MAPK, and that optionally has defective Rac, axin, or beta-catenin function (e.g. Rac, axin, or beta-catenin is over-expressed or under-expressed relative to wild-type cells). A test agent can be added to the hypoxic induction assay system and changes in hypoxic response relative to controls where no test agent is added, identify candidate Rac, axin, and beta-catenin modulating agent. In some embodiments of the invention, the hypoxic induction assay may be used as a secondary assay to test a candidate Rac, axin, and beta-catenin modulating agent that is initially identified using another assay system. A hypoxic induction assay may also be used to test whether MAPK function plays a direct role in the hypoxic response. For example, a hypoxic induction assay may be performed on cells that over- or under-express MAPK relative to wild type cells. Differences in hypoxic response compared to wild type cells suggest that the MAPK plays a direct role in hypoxic induction.

Cell adhesion. Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346-53).

Tubulogenesis. Tubulogenesis assays monitor the ability of cultured cells, generally endothelial cells, to form tubular structures on a matrix substrate, which generally simulates the environment of the extracellular matrix, Exemplary substrates include MATRIGEL™ (Becton Dickinson), an extract of basement membrane proteins containing laminin, collagen IV, and heparin sulfate proteoglycan, which is liquid at 4° C. and forms a solid gel at 37° C. Other suitable matrices comprise extracellular components such as collagen, fibronectin, and/or fibrin. Cells are stimulated with a pro-angiogenic stimulant, and their ability to form tubules is detected by imaging. Tubules can generally be detected after an overnight incubation with stimuli, but longer or shorter time frames may also be used. Tube formation assays are well known in the art (e.g., Jones M K et al., 1999, Nature Medicine 5:1418-1423). These assays have traditionally involved stimulation with serum or with the growth factors FGF or VEGF. Serum represents an undefined source of growth factors. In a preferred embodiment, the assay is performed with cells cultured in serum free medium, in order to control which process or pathway a candidate agent modulates. Moreover, we have found that different target genes respond differently to stimulation with different pro-angiogenic agents, including inflammatory angiogenic factors such as TNF-alpha. Thus, in a further preferred embodiment, a tubulogenesis assay system comprises testing a MAPK's response to a variety of factors, such as FGF, VEGF, phorbol myristate acetate (PMA), TNF-alpha, ephrin, etc.

Cell Migration. An invasion/migration assay (also called a migration assay) tests the ability of cells to overcome a physical barrier and to migrate towards pro-angiogenic signals. Migration assays are known in the art (e.g., Paik J H et al., 2001, J Biol Chem 276:11830-11837). In a typical experimental set-up, cultured endothelial cells are seeded onto a matrix-coated porous lamina, with pore sizes generally smaller than typical cell size. The matrix generally simulates the environment of the extracellular matrix, as described above. The lamina is typically a membrane, such as the transwell polycarbonate membrane (Corning Costar Corporation, Cambridge, Mass.), and is generally part of an upper chamber that is in fluid contact with a lower chamber containing pro-angiogenic stimuli. Migration is generally assayed after an overnight incubation with stimuli, but longer or shorter time frames may also be used. Migration is assessed as the number of cells that crossed the lamina, and may be detected by staining cells with hemotoxylin solution (VWR Scientific, South San Francisco, Calif.), or by any other method for determining cell number. In another exemplary set up, cells are fluorescently labeled and migration is detected using fluorescent readings, for instance using the Falcon HTS FluoroBlok (Becton Dickinson). While some migration is observed in the absence of stimulus, migration is greatly increased in response to pro-angiogenic factors. As described above, a preferred assay system for migration/invasion assays comprises testing a MAPK's response to a variety of pro-angiogenic factors, including tumor angiogenic and inflammatory angiogenic agents, and culturing the cells in serum free medium.

Sprouting assay. A sprouting assay is a three-dimensional in vitro angiogenesis assay that uses a cell-number defined spheroid aggregation of endothelial cells ("spheroid"), embedded in a collagen gel-based matrix. The spheroid can serve as a starting point for the sprouting of capillary-like structures by invasion into the extracellular matrix (termed "cell sprouting") and the subsequent formation of complex anastomosing networks (Korff and Augustin, 1999, J Cell Sci 112:3249-58). In an exemplary experimental set-up, spheroids are prepared by pipetting 400 human umbilical vein endothelial cells into individual wells of a nonadhesive 96-well plates to allow overnight spheroidal aggregation (Korff and Augustin: J Cell Biol 143: 1341-52, 1998). Spheroids are harvested and seeded in 900 µl of methocel-collagen solution and pipetted into individual wells of a 24 well plate to allow collagen gel polymerization. Test agents are added after 30 min by pipetting 100 µl of 10-fold concentrated working dilution of the test substances on top of the gel. Plates are incubated at 37° C. for 24 h. Dishes are fixed at the end of the experimental incubation period by addition of paraformaldehyde. Sprouting intensity of endothelial cells can be quantitated by an automated image analysis system to determine the cumulative sprout length per spheroid.

Primary Assays for Antibody Modulators

For antibody modulators, appropriate primary assays test is a binding assay that tests the antibody's affinity to and specificity for the MAPK protein. Methods for testing antibody affinity and specificity are well known in the art (Harlow and Lane, 1988, 1999, supra). The enzyme-linked immunosorbant assay (ELISA®) is a preferred method for detecting MAPK-specific antibodies; others include FACS assays, radioimmunoassays, and fluorescent assays.

In some cases, screening assays described for small molecule modulators may also be used to test antibody modulators.

Primary Assays for Nucleic Acid Modulators

For nucleic acid modulators, primary assays may test the ability of the nucleic acid modulator to inhibit or enhance MAPK gene expression, preferably mRNA expression. In general, expression analysis comprises comparing MAPK expression in like populations of cells (e.g., two pools of cells that endogenously or recombinantly express MAPK) in the presence and absence of the nucleic acid modulator. Methods for analyzing mRNA and protein expression are well known in the art. For instance, Northern blotting, slot blotting, ribonuclease protection, quantitative RT-PCR (e.g., using the TAQMAN®, PE APPLIED BIOSYSTEMS®), or microarray analysis may be used to confirm that MAPK mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the MAPK protein or specific peptides. A variety of means including Western blotting, ELISA®, or in situ detection, are available (Harlow E and Lane D, 1988 and 1999, supra).

In some cases, screening assays described for small molecule modulators, particularly in assay systems that involve MAPK mRNA expression, may also be used to test nucleic acid modulators.

Secondary Assays

Secondary assays may be used to further assess the activity of MAPK-modulating agent identified by any of the above methods to confirm that the modulating agent affects MAPK in a manner relevant to the Rac, axin, and beta-catenin pathways. As used herein, MAPK-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with MAPK.

Secondary assays generally compare like populations of cells or animals (e.g., two pools of cells or animals that endogenously or recombinantly express MAPK) in the presence and absence of the candidate modulator. In general, such assays test whether treatment of cells or animals with a candidate MAPK-modulating agent results in changes in the Rac, axin, and beta-catenin pathways in comparison to untreated (or mock- or placebo-treated) cells or animals. Certain assays use "sensitized genetic backgrounds", which, as used herein, describe cells or animals engineered for altered expression of genes in the Rac, axin, and beta-catenin or interacting pathways.

Cell-Based Assays

Cell based assays may detect endogenous Rac, axin, and beta-catenin pathways activity or may rely on recombinant expression of Rac, axin, and beta-catenin pathways components. Any of the aforementioned assays may be used in this cell-based format. Candidate modulators are typically added to the cell media but may also be injected into cells or delivered by any other efficacious means.

Animal Assays

A variety of non-human animal models of normal or defective Rac, axin, or beta-catenin pathways may be used to test candidate MAPK modulators. Models for defective Rac, axin, or beta-catenin pathways typically use genetically modified animals that have been engineered to mis-express (e.g., over-express or lack expression in) genes involved in the Rac, axin, and beta-catenin pathways. Assays generally require systemic delivery of the candidate modulators, such as by oral administration, injection, etc.

In a preferred embodiment, Rac, axin, and beta-catenin pathways activity is assessed by monitoring neovascularization and angiogenesis. Animal models with defective and normal Rac, axin, and beta-catenin are used to test the candidate modulator's effect on MAPK in MATRIGEL® assays. MATRIGEL® is an extract of basement mnembrane proteins, and is composed primarily of laminin, collagen IV, and heparin sulfate proteoglycan. It is provided as a sterile liquid at 4° C., but rapidly forms a solid gel at 37° C. Liquid MATRIGEL® is mixed with various angiogenic agents, such as bFGF and VEGF, or with human tumor cells which over-express the MAPK. The mixture is then injected subcutaneously(SC) into female athymic nude mice (Taconic, Germantown, N.Y.) to support an intense vascular response. Mice with MATRIGEL® pellets may be dosed via oral (PO), intraperitoneal (IP), or intravenous (IV) routes with the candidate modulator. Mice are euthanized 5-12 days post-injection, and the MATRIGEL® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on MAPK is assessed via tumorigenicity assays. Tumor xenograft assays are known in the art (see, e.g., Ogawa K et al., 2000, Oncogene 19:6043-6052). Xenografts are typically implanted SC into female athymic mice, 6-7 week old, as single cell suspensions either from a pre-existing tumor or from in vitro culture. The tumors which express the MAPK endogenously are injected in the flank, $1\times10^5$ to $1\times10^7$ cells per mouse in a volume of 100 μL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration, Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

In another preferred embodiment, tumorogenicity is monitored using a hollow fiber assay, which is described in U.S. Pat. No. 5,698,413. Briefly, the method comprises implanting into a laboratory animal a biocompatible, semi-permeable encapsulation device containing target cells, treating the laboratory animal with a candidate modulating agent, and evaluating the target cells for reaction to the candidate modulator. Implanted cells are generally human cells from a pre-existing tumor or a tumor cell line. After an appropriate period of time, generally around six days, the implanted samples are harvested for evaluation of the candidate modulator. Tumorogenicity and modulator efficacy may be evaluated by assaying the quantity of viable cells present in the macrocapsule, which can be determined by tests known in the art, for example, MTT dye conversion assay, neutral red dye uptake, trypan blue staining, viable cell counts, the number of colonies formed in soft agar, the capacity of the cells to recover and replicate in vitro, etc.

In another preferred embodiment, a tumorogenicity assay use a transgenic animal, usually a mouse, carrying a dominant oncogene or tumor suppressor gene knockout under the control of tissue specific regulatory sequences; these assays are generally referred to as transgenic tumor assays. In a preferred application, tumor development in the transgenic model is well characterized or is controlled. In an exemplary model, the "RIP1-Tag2" transgene, comprising the SV40 large T-antigen oncogene under control of the insulin gene regulatory regions is expressed in pancreatic beta cells and results in islet cell carcinomas (Hanahan D, 1985, Nature 315:115-122; Parangi S et al, 1996, Proc Natl Acad Sci USA 93: 2002-2007; Bergers G et al, 1999, Science 284:808-812). An "angiogenic switch," occurs at approximately five weeks, as normally quiescent capillaries in a subset of hyperproliferative islets become angiogenic. The RIP1-TAG2 mice die by age 14 weeks. Candidate modulators may be administered at a variety of stages, including just prior to the angiogenic switch (e.g., for a model of tumor prevention), during the growth of small tumors (e.g., for a model of intervention), or during the growth of large and/or invasive tumors (e.g., for a model of regression). Tumorogenicity and modulator efficacy can be evaluating life-span extension and/or tumor characteristics, including number of tumors, tumor size, tumor morphology, vessel density, apoptotic index, etc.

Diagnostic and Therapeutic Uses

Specific MAPK-modulating agents are useful in a variety of diagnostic and therapeutic applications where disease or disease prognosis is related to defects in the Rac, axin, or beta-catenin pathways, such as angiogenic, apoptotic, or cell proliferation disorders. Accordingly, the invention also provides methods for modulating the Rac, axin, and beta-catenin pathways in a cell, preferably a cell pre-determined to have defective or impaired Rac, axin, or beta-catenin function (e.g. due to overexpression, underexpression, or misexpression of Rac, axin, or beta-catenin, or due to gene mutations), comprising the step of administering an agent to the cell that specifically modulates MAPK activity. Preferably, the modulating agent produces a detectable phenotypic change in the cell indicating that the Rac, axin, or beta-catenin function is restored. The phrase "function is restored", and equivalents, as used herein, means that the desired phenotype is achieved, or is brought closer to normal compared to untreated cells. For example, with restored Rac, axin, or beta-catenin function, cell proliferation and/or progression through cell cycle may normalize, or be brought closer to normal relative to untreated cells. The invention also provides methods for treating disorders or disease associated with impaired Rac, axin, or beta-catenin function by administering a therapeutically effective amount of a MAPK-modulating agent that modulates the Rac, axin, and beta-catenin pathways. The invention further provides methods for modulating MAPK function in a cell, preferably a cell pre-determined to have defective or impaired MAPK function, by administering a MAPK-modulating agent. Additionally, the invention provides a method for treating disorders or disease associated with impaired MAPK function by administering a therapeutically effective amount of a MAPK-modulating agent.

The discovery that MAPK is implicated in Rac, axin, and beta-catenin pathways provides for a variety of methods that can be employed for the diagnostic and prognostic evaluation of diseases and disorders involving defects in the Rac, axin, and beta-catenin pathways and for the identification of subjects having a predisposition to such diseases and disorders.

Various expression analysis methods can be used to diagnose whether MAPK expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). Tissues having a disease or disorder implicating defective Rac, axin, or beta-catenin signaling that express a MAPK, are identified as amenable to treatment with a MAPK modulating agent. In a preferred application, the Rac, axin, and beta-catenin defective tissue overexpresses a MAPK relative to normal tissue. For example, a Northern blot analysis of mRNA from tumor and normal cell lines, or from tumor and matching normal tissue samples from the same patient, using full or partial MAPK cDNA sequences as probes, can determine whether particular tumors express or overexpress MAPK. Alternatively, the TAQMAN® is used for quantitative RT-PCR analysis of MAPK expression in cell lines, normal tissues and tumor samples (PE APPLIED BIOSYSTEMS®).

Various other diagnostic methods may be performed, for example, utilizing reagents such as the MAPK oligonucleotides, and antibodies directed against a MAPK, as described above for: (1) the detection of the presence of MAPK gene mutations, or the detection of either over- or under-expression of MAPK mRNA relative to the non-disorder state; (2) the detection of either an over- or an under-abundance of MAPK gene product relative to the non-disorder state; and (3) the detection of perturbations or abnormalities in the signal transduction pathway mediated by MAPK.

Thus, in a specific embodiment, the invention is drawn to a method for diagnosing a disease or disorder in a patient that is associated with alterations in MAPK expression, the method comprising: a) obtaining a biological sample from the patient; b) contacting the sample with a probe for MAPK expression; c) comparing results from step (b) with a control; and d) determining whether step (c) indicates a likelihood of the disease or disorder. Preferably, the disease is cancer, most preferably a cancer as shown in TABLE 1. The probe may be either DNA or protein, including an antibody.

EXAMPLES

The following experimental section and examples are offered by way of illustration and not by way of limitation.

I. *C. elegans* Rac Enhancer Screen

A genetic screen was designed to identify modifiers of the Rac signaling pathway that also affect cell migrations in *C. elegans*. The basis of this screen is the observation that ced-10 and mig-2 single mutants resemble wildtype worms in morphology and movement, whereas double mutants have strong morphological and movement defects. In the primary screen, the function of individual genes is inactivated by RNA interference (RNAi) in wildtype, ced-10 and mig-2 worms at the L4 stage. The progeny of the RNA treated animals are then examined for morphological and movement defects resembling those of the ced-10; mig-2 double mutant. All genes that give such a phenotype in a ced-10 or mig-2 mutant background but not in a wildtype background are then tested in a direct cell migration assay. In the cell migration assay, a subset of mechanosensory neurons known as AVM and ALM are scored for their final positions in the animal using a GFP marker expressed in these cells. This migration assay is done in both wildtype and a ced-10 or mig-2 mutant background.

Since the AVM and ALM cells normally migrate and reach their final position during the first larval stage, scoring of position is done in later larval or adult stages. Those genes that cause short or misguided migrations of these neurons when inactivated in a wildtype or rac mutant background are potentially relevant for treatment of diseases that involve cell migrations. ZC504.4 was an enhancer in the screen.

II. *C. elegans* Axin Screen

We have found that the temperature-sensitive, reduction-of-function pry-1 mutant mu38 grown at 15° C. produces a ruptured vulva (Rvl) phenotype by which about 95% of animals become eviscerated and die at the L4 molt. The pry-1 Rvl mutant phenotype is suppressed by loss-of-function mutations in the beta-catenin ortholog bar-1 and the TCF ortholog pop-1. The Rvl phenotype can also be generated by gain-of-function mutations in bar-1/beta-catenin that eliminate the consensus GSK3-beta phosphorylation sites and are predicted to prevent Axin-mediated degradation of BAR-1.

We designed a genetic screen to identify genes in addition to bar-1/beta-catenin and pop-1/TCF that act positively in beta-catenin signaling and, when inactivated, suppress the Rvl mutant phenotype of pry-1/Axin. The function of individual genes was inactivated by RNAi in pry-1(mu38) L1 larvae, and suppression of the Rvl phenotype was scored as a statistically significant increase in the proportion of larvae that survived to adulthood without rupturing. Suppressor genes were subsequently counterscreened to eliminate those that appeared to suppress the pry-1 mutant non-specifically, rather than those that specifically functioned in beta-catenin signaling. Suppressor genes that did not block vulva formation in a wildtype background, and that did not suppress the Rvl phenotype of two mutations in genes unrelated to beta-catenin signaling (lin-1/Ets and daf-18/PTEN) were considered to be specific pry-1/Axin suppressors. These suppressor genes, when inactivated, likely suppress beta-catenin's inappropriate transcriptional activation of target genes and, therefore, may be relevant for cancer therapy. ZC504.4 was identified as a suppressor in the screen.

III. *C. elegans* Beta-Catenin Screen

The identification of mutants that suppress the cell adhesion defect of beta-catenin may lead to unique therapeutic targets that inhibit cell migration or metastasis. hmp-2 was initially identified in an EMS screen for defects in body elongation during embryonic morphogenesis (see Costa et al., (1998) The Journal of Cell Biology 1998, 141: 297-308). The loss of function allele hmp-2 (zu364) exhibits 99% embryonic lethality, with mutant embryos arresting during elongation and abnormal bulges forming on the dorsal side. About 1% of these embryos hatch to form viable lumpy larvae. The reduction of function allele hmp-2 (qm39) yields viable larvae with a characteristic lumpy appearance. When grown at 15° C., approximately 92% (SD 3.9) of the L1 larvae show this lumpy phenotype, with the penetrance of the phenotype decreasing as the animals molt and move through successive larval stages. For this screen, hmp-2 (qm39) worms were soaked at 15° C. in double stranded RNA (dsRNA) at the L4 larval stage and the progeny were scored as L1 larvae for modification of the adhesion defect. The screen protocol is described below.

1) hmp-2 (qm39) animals were bleached and hatched on peptone free agarose plates to produce a synchronous population. Starved L1s were transferred to 10× peptone plates seeded with 750 μl OP50 (25% w/v in TB) and allowed to develop to the L4 larval stage.

2) dsRNA was dispensed in 6 μl aliquots into 96 well round bottom plates (Nunc #262162). L4 animals were collected by suspension in M9 buffer, washed 2× with M9 to remove any excess OP50, and dispensed in 2 μl aliquots into the RNA to a total worm density of 75-100 worms per well. As a control, multiple wells contained only RNA resuspension buffer (1× IM buffer).

3) Animals were soaked in dsRNA at 15° C. for 24 hours.

4) Following dsRNA soaking, the animals were fed in the wells by addition of 25 μl liquid NGM+3% OP50. The animals were kept at 15° C. and allowed to become gravid and lay progeny in the wells, which took approximately 72 hours. Food levels were monitored visually during maturation and more was added as needed.

5) Following maturation, animals from each well were plated onto individual 6 cm peptone free agarose plates and placed at 15° C. overnight.

6) Animals on each plate were scored visually under the dissecting microscope for modification of the lumpy phenotype. Scoring was performed qualitatively, with an increase in dead embryos scored as enhancement and an increase in wild type appearing animals scored as suppression of the defect.

7) Retests of interesting suppressor candidates followed the same protocol as the primary screen with certain modifications: several retests were performed for each suppressor, retested candidates were encoded so that they could be scored blindly, and retested candidates were scored quantitatively. Each plate was scored by counting 100 total objects. An object was defined as either an embryo or an L1 stage larva. Each object was scored as one of the following: a wildtype appearing animal, a lumpy appearing animal, or an unhatched embryo. Scores were represented as the percentage of wildtype appearing animals relative to all objects scored. Wildtype animals were defined as L1 larvae with smooth cuticles that did not have any sort of lumpy body morphology.

A confirmed suppressor was one that was ≧2 standard deviations away from the mean of the controls for at least 3 of the four retest experiments. ZC504.4 was identified as a suppressor in the screen.

IV. Sequence Analysis

BLAST analysis (Altschul et al., supra) was employed to identify orthologs of *C. elegans* ZC504.4. For example, representative sequences from MAPK, SEQ ID NOs:36, 37, and 38 share 45%, 48%, and 45% amino acid identity, respectively, with the *C. elegans* ZC504.4.

Various domains, signals, and functional subunits in proteins were analyzed using the PSORT (Nakai K., and Horton P., Trends Biochem Sci, 1999, 24:34-6; Kenta Nakai, Protein sorting signals and prediction of subcellular localization, Adv. Protein Chem. 54, 277-344 (2000)), PFAM (Bateman A., et al., Nucleic Acids Res, 1999, 27:260-2), SMART (Ponting C P, et al., SMART:identification and annotation of domains from signaling and extracellular protein sequences. Nucleic Acids Res. 1999 Jan. 1; 27(1):229-32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998), and clust (Remm M, and Sonnhammer E. Classification of transmembrane protein families in the *Caenorhabditis elegans* genome and identification of human orthologs. Genome Res. 2000 Nov; 10(11):1679-89) programs. For example, the CNH domain (PFAM 00780) of MAPK from SEQ ID NOs:36, 37, 38, and 39, are respectively located at approximately amino acid residues 1018 to 1309, 845 to 1144, 982 to 1273, and 1209 to 1556. Further, protein kinase domains (PFAM 00069)

of SEQ ID NOs:36, 37, 38, and 39, are located respectively at approximately amino acid residues 25 to 289, 25 to 289, 25 to 289, and 25 to 313.

V. High-Throughput In Vitro Fluorescence Polarization Assay

Fluorescently-labeled MAPK peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of MAPK activity.

VI. High-Throughput In Vitro Binding Assay.

$^{33}$P-labeled MAPK peptide is added in an assay buffer (100 mM KCl, 20 mM HEPES pH 7.6, 1 mM $MgCl_2$, 1% glycerol, 0.5% NP40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate Rac, axin, and beta-catenin modulating agents.

VII. Immunoprecipitations and Immunoblotting

For coprecipitation of transfected proteins, $3\times10^6$ appropriate recombinant cells containing the MAPK proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 μl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

VIII. Kinase Assay

A purified or partially purified MAPK is diluted in a suitable reaction buffer, e.g., 50 mM Hepes, pH 7.5, containing magnesium chloride or manganese chloride (1-20 mM) and a peptide or polypeptide substrate, such as myelin basic protein or casein (1-10 μg/ml). The final concentration of the kinase is 1-20 nM. The enzyme reaction is conducted in microtiter plates to facilitate optimization of reaction conditions by increasing assay throughput. A 96-well microtiter plate is employed using a final volume 30-100 μl. The reaction is initiated by the addition of $^{33}$P-gamma-ATP (0.5 μCi/ml) and incubated for 0.5 to 3 hours at room temperature. Negative controls are provided by the addition of EDTA, which chelates the divalent cation ($Mg2^+$ or $Mn^{2+}$) required for enzymatic activity. Following the incubation, the enzyme reaction is quenched using EDTA. Samples of the reaction are transferred to a 96-well glass fiber filter plate (MultiScreen, Millipore). The filters are subsequently washed with phosphate-buffered saline, dilute phosphoric acid (0.5%) or other suitable medium to remove excess radiolabeled ATP. Scintillation cocktail is added to the filter plate and the incorporated radioactivity is quantitated by scintillation counting (Wallac/Perkin Elmer). Activity is defined by the amount of radioactivity detected following subtraction of the negative control reaction value (EDTA quench).

IX. Expression Analysis

All cell lines used in the following experiments are NCI (National Cancer Institute) lines, and are available from ATCC$^{SM}$ (American Type Culture Collection, Manassas, Va. 20110-2209). Normal and tumor tissues were obtained from Impath, UC Davis, CLONTECH™, STRATAGENE®, Ardais, Genome Collaborative, and AMBION®.

TAQMAN® analysis was used to assess expression levels of the disclosed genes in various samples.

RNA was extracted from each tissue sample using QIAGEN™ (Valencia, Calif.) RNEASY® kits, following manufacturer's protocols, to a final concentration of 50 ng/μl. Single stranded cDNA was then synthesized by reverse transcribing the RNA samples using random hexamers and 500 ng of total RNA per reaction, following protocol 4304965 of APPLIED BIOSYSTEMS® (Foster City, Calif.).

Primers for expression analysis using TAQMAN® assay (APPLIED BIOSYSTEMS®, Foster City, Calif.) were prepared according to the TAQMAN® protocols, and the following criteria: a) primer pairs were designed to span introns to eliminate genomic contamination, and b) each primer pair produced only one product. Expression analysis was performed using a 7900HT instrument.

TAQMAN® reactions were carried out following manufacturer's protocols, in 25 μl total volume for 96-well plates and 10 μl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor−average(all normal samples)>2× STDEV(all normal samples)).

Results are shown in Table 1. Number of pairs of tumor samples and matched normal tissue from the same patient are shown for each tumor type. Percentage of the samples with at least two-fold overexpression for each tumor type is provided. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

TABLE 1

| | GI# | | | |
|---|---|---|---|---|
| | 22041067 | 4758523 | 7657334 | 20549227 |
| | Seq ID NO | | | |
| | 1 | 13 | 21 | 29 |
| Breast | 33% | 6% | 6% | 36% |
| # of Pairs | 36 | 35 | 36 | 36 |
| Colon | 10% | 29% | 3% | 27% |
| # of Pairs | 40 | 38 | 39 | 41 |
| Head And Neck | 31% | 31% | 38% | 31% |
| # of Pairs | 13 | 13 | 13 | 13 |
| Kidney | 36% | 45% | 9% | 9% |
| # of Pairs | 22 | 22 | 22 | 22 |
| Liver | 20% | 40% | 40% | 50% |
| # of Pairs | 5 | 5 | 5 | 8 |
| Lung | 2% | 17% | 2% | 56% |
| # of Pairs | 40 | 41 | 41 | 41 |
| Lymphoma | 0% | 50% | 0% | 0% |
| # of Pairs | 3 | 2 | 3 | 3 |
| Ovary | 39% | 16% | 5% | 16% |
| # of Pairs | 18 | 19 | 19 | 19 |
| Pancreas | 89% | 67% | 67% | 77% |
| # of Pairs | 9 | 9 | 9 | 13 |
| Prostate | 14% | 10% | 9% | 16% |
| # of Pairs | 22 | 20 | 22 | 25 |
| Skin | 57% | 57% | 0% | 14% |
| # of Pairs | 7 | 7 | 7 | 7 |
| Stomach | 9% | 73% | 18% | 64% |
| # of Pairs | 11 | 11 | 11 | 11 |
| Testis | 0% | 0% | 0% | 38% |
| # of Pairs | 8 | 8 | 8 | 8 |
| Thyroid Gland | 43% | 21% | 14% | 36% |
| # of Pairs | 14 | 14 | 14 | 14 |
| Uterus | 15% | 5% | 5% | 4% |
| # of Pairs | 20 | 21 | 21 | 24 |

X. MAPK Functional Assays

RNAi experiments were carried out to knock down expression of MAPK sequences in various cell lines using small interfering RNAs (siRNA, Elbashir et al, supra).

Effect of MAPK RNAi on cell proliferation and growth. BrdU and CELL TITER-GLO™ assays, as described above, were employed to study the effects of decreased MAPK expression on cell proliferation. Results: RNAi of MAPK of SEQ ID NO:1 decreased proliferation in LX1 lung cancer, and 231T breast cancer cells; RNAi of SEQ ID NO:12 decreased proliferation in LX1 lung cancer, 231T breast cancer, and HCT116 colon cancer cells; RNAi of SEQ ID NO:21 decreased proliferation in HCT116 colon cancer and 231T breast cancer cells; RNAi of SEQ ID NO:29 decreased proliferation in LX1 lung cancer cells.

MTS cell proliferation assay, as described above, was also employed to study the effects of decreased MAPK expression on cell proliferation. Results: RNAi of MAPK of SEQ ID NO:1 decreased proliferation in A549 and LX1 lung cancer, and MDA231 breast cancer cells; RNAi of MAPK of SEQ ID NO:21 decreased proliferation in A549 and LX1 lung cancer, and MDA231 breast cancer cells; RNAi of MAPK of SEQ ID NO:12 decreased proliferation in A549 and LX1 lung cancer, and MDA231 breast cancer cells; and RNAi of SEQ ID NO:29 decreased proliferation in LX1 lung cancer cells.

Standard colony growth assays, as described above, were employed to study the effects of decreased MAPK expression on cell growth. Results: RNAi of SEQ ID NOs:1 and 21 decreased cell growth in LX1 and A549 lung cancer, MDA231 breast cancer, and A2780 ovarian cancer line. RNAi of SEQ ID NO:29 decreased proliferation in LX1 lung cancer cells.

Effect of MAPK RNAi on apoptosis. Nucleosome ELISA apoptosis assay, as described above, was employed to study the effects of decreased MAPK expression on apoptosis. Results: RNAi of SEQ ID NO:12 increased apoptosis in LX1 lung cancer cells;

Effect of MAPK RNAi on cell cycle. Propidium iodide (PI) cell cycle assay, as described above, was employed to study the effects of decreased MAPK expression on cell cycle. Results: RNAi of SEQ ID NO:12 increased the sub-G1 peak in LX1 lung cancer cells; RNAi of SEQ ID NO:21 increased the sub-G1 peak in LX1 lung cancer cells. The region of subG1 represents cells undergoing apoptosis-associated DNA degradation.

MAPK overexpression analysis. MAPK sequences were overexpressed and tested in colony growth assays as described above. Overexpressed MAPK of SEQ ID NO:12 caused increased NIH3T3 colony growth. Over expression of SEQ ID NO:21 caused no morphological effects, and had moderate effect on colony growth.

Effects of overexpressed MAPK on expression of various transcription factors was also studied. Overexpressed MAPK of SEQ ID NO:21 caused an increased expression of the following transcription factors: E2F, SRE (Serum response element), AP1 (Activator protein 1), ETS 1 (ETS oncogene; v-ets avian erythroblastosis virus e26 oncogene homolog 1), STAT3 (signal transducer and activator of transcription 3), and EGR (Early growth response).

What is claimed is:

1. A method of identifying a candidate RAC, axin, and beta-catenin pathways modulating agent, said method comprising the steps of:

(a) providing an assay system comprising a Mitogen Activated Protein Kinase (MAPK) polypeptide comprising SEQ ID NO: 36, 37, 38 and 40 or nucleic acid comprising SEQ ID NO: 1, 10, 12, 13, 21, and 29, wherein the assay system is capable of detecting the activity or expression of MAPK;

(b) contacting the assay system with a test agent that modulates the activity or expression of MAPK; and (c) determining the activity or expression of the MAPK polypeptide or nucleic acid in the assay system in the presence or absence of the test agent of step (b), wherein a change in MAPK activity or expression between the presence and absence of the test agent identifies the test agent as a candidate RAC, axin, and beta-catenin pathways modulating agent;

(d) providing a second assay system comprising cultured cells or a non-human animal expressing MAPK and capable of detecting change in the RAC, axin, and beta-catenin pathways;

(e) contacting the second assay system with the test agent of (b); and (f) measuring the Rac, axin, and beta-catenin pathways in the presence or absence of the test agent, wherein the detection of a difference in the presence and absence of the test agent confirms the test agent as a RAC, axin, and beta-catenin pathways modulating agent.

2. The method of claim 1 wherein the first assay system comprises cultured cells that express the MAPK polypeptide.

3. The method of claim 2 wherein the cultured cells additionally have defective RAC, axin, and beta-catenin pathways function.

4. The method of claim 1 wherein the first assay system includes a screening assay comprising a MAPK polypeptide, and the candidate test agent is a small molecule modulator.

5. The method of claim 4 wherein the screening assay is a kinase assay.

6. The method of claim 1 wherein the second assay system is selected from the group consisting of an apoptosis assay system, a cell proliferation assay system, an angiogenesis assay system, and a hypoxic induction assay system.

7. The method of claim 1 wherein the first assay system includes a binding assay comprising a MAPK polypeptide and the candidate test agent is an antibody.

8. The method of claim 1 wherein the first assay system includes an expression assay comprising a MAPK nucleic acid and the candidate test agent is a nucleic acid modulator.

9. The method of claim 8 wherein the nucleic acid modulator is an antisense oligomer.

10. The method of claim 8 wherein the nucleic acid modulator is a phosphothioate morpholino oligomer (PMO).

11. The method of claim 1 wherein the second assay system comprises cells defective in Rac, axin, and beta-catenin pathways function and is capable of detecting a phenotypic change in the model system that indicates that the Rac, axin, and beta-catenin pathways function is restored when compared relative to wild-type cells.

12. The method of claim 11 wherein the model system is a mouse model with defective Rac, axin, and beta-catenin pathways function.

* * * * *